US012810962B2

(12) United States Patent
Davis et al.

(10) Patent No.: US 12,810,962 B2
(45) Date of Patent: Nov. 24, 2026

(54) APPARATUSES, SYSTEMS, AND METHODS FOR EXTRACTING MEANING FROM DNA SEQUENCE DATA USING NATURAL LANGUAGE PROCESSING (NLP)

(71) Applicant: BASF Agricultural Solutions US LLC, Research Triangle Park, NC (US)

(72) Inventors: Erin Marie Davis, Cary, NC (US); Sebastian Hermann Martschat, Heidelberg (DE); Jonathan T. Vogel, Cary, NC (US)

(73) Assignee: BASF Agricultural Solutions US LLC, Research Triangle Park, NC (US)

( * ) Notice: Subject to any disclaimer, the term of this patent is extended or adjusted under 35 U.S.C. 154(b) by 1125 days.

(21) Appl. No.: 17/088,734

(22) Filed: Nov. 4, 2020

(65) Prior Publication Data

US 2022/0139498 A1 May 5, 2022

(51) Int. Cl.

*G06N 3/045* (2023.01)
*G06N 3/08* (2023.01)
*G16B 40/00* (2019.01)
*G06F 40/20* (2020.01)

(52) U.S. Cl.

CPC ............. *G16B 40/00* (2019.02); *G06N 3/045* (2023.01); *G06N 3/08* (2013.01); *G06F 40/20* (2020.01)

(58) Field of Classification Search

CPC ........... G16B 40/00; G06N 3/045; G06N 3/08
See application file for complete search history.

(56) References Cited

U.S. PATENT DOCUMENTS

| | | | | |
|---|---|---|---|---|
| 11,587,645 B2 * | 2/2023 | Amimeur | G06N 3/123 | |
| 2002/0168664 A1 * | 11/2002 | Murray | G16B 50/00 | 435/6.14 |
| 2003/0154078 A1 * | 8/2003 | Rees | G10L 15/10 | 704/240 |

(Continued)

FOREIGN PATENT DOCUMENTS

WO WO-2020/188119 A1 9/2020

OTHER PUBLICATIONS

Shi et al., A vector Representation of DNA Sequence Using locality Sensitive Hashing,bioRxiv preprint doi (Year: 2019).*
Patrick Ng, dna2vec:Consistent Vector representations of variable-length k-mers, arXiv:1701.06279v1[q-bio.QM] Jan. 23, 2017 (Year : 2017).*

(Continued)

*Primary Examiner* — Hien L Duong
(74) *Attorney, Agent, or Firm* — MARSHALL, GERSTEIN & BORUN LLP; William J. Samore

(57) ABSTRACT

Apparatuses, systems, and methods are provided that may analyze deoxyribonucleic add (DNA) sequence data using a natural language processing (NLP) model to, for example, identify genetic elements such as known and/or novel cis-regulatory elements (e.g., known and/or putative novel drought-responsive cis-regulatory elements (DREs)). Apparatuses, systems, and methods are also provided that may identify transcriptional regulators (e.g., upstream transcriptional regulators of a novel putative DRE) based on natural language processing (NLP) model data and expression genome-wide association study (eGWAS) data. Apparatuses, systems, and methods are also provided that may verify putative novel cis-regulatory elements based on a comparison of natural language processing (NLP) model output data and other model output data.

20 Claims, 37 Drawing Sheets

Specification includes a Sequence Listing.

(56) References Cited

U.S. PATENT DOCUMENTS

| | | | | |
|---|---|---|---|---|
| 2015/0100244 | A1* | 4/2015 | Hannum | G16B 30/00 702/19 |
| 2015/0379399 | A1* | 12/2015 | Baughman | G06F 40/253 706/13 |
| 2019/0018019 | A1* | 1/2019 | Shan | G16B 40/10 |
| 2019/0065675 | A1* | 2/2019 | Yelensky | G16H 20/10 |
| 2019/0087726 | A1* | 3/2019 | Greenblatt | G06N 3/08 |
| 2020/0073995 | A1* | 3/2020 | Martin | G16H 70/40 |
| 2020/0118648 | A1* | 4/2020 | Chang | G06N 3/08 |
| 2020/0126126 | A1* | 4/2020 | Briancon | G06N 20/20 |
| 2020/0194098 | A1* | 6/2020 | Hannigan | G06N 3/044 |
| 2020/0302011 | A1* | 9/2020 | Mishra | G06F 40/242 |
| 2020/0357482 | A1* | 11/2020 | Devesa | G16B 50/10 |
| 2021/0057107 | A1* | 2/2021 | Solomon | G06N 3/044 |
| 2021/0065907 | A1* | 3/2021 | Neumann | G16H 20/00 |
| 2021/0141833 | A1* | 5/2021 | Davis | G16B 10/00 |
| 2021/0295180 | A1* | 9/2021 | Neumann | G06N 3/08 |
| 2022/0284983 | A1* | 9/2022 | Lupien | G16B 20/30 |

OTHER PUBLICATIONS

International Application No. PCT/US2021/057491, International Search Report and Written Opinion, mailed Jan. 31, 2022.

Mishra et al., Identification of cis-regulatory elements associated with salinity and drought stress tolerance in rice from co-expressed gene interaction networks, Bioinformation, 14(3): 123-31 (2018).

Mejia-Guerra et al., A k-mer grammar analysis to uncover maize regulatory architecture, BMC Plant Biology, 19:103 (2019).

Ji et al., DNABERT: pre-trained bidirectional encoder representations from transformers model for DNA-language in genome, bioRxiv, Sep. 19, 2020.

Li et al., Computational prediction and interpretation of both general and specific types of promoters in *Escherichia coli* by exploiting a stacked ensemble-learning framework, Briefings in Bioinformatics, 22(2):2126-40 (May 4, 2020).

Liu et al., iEnhancer-EL: identifying enhancers and their strength with ensemble learning approach, Bioinformatics, 34(22):3835-42 (Jun. 2018).

* cited by examiner

700

800a

800b

800c

900

1000

1300

1500b

APPARATUSES, SYSTEMS, AND METHODS FOR EXTRACTING MEANING FROM DNA SEQUENCE DATA USING NATURAL LANGUAGE PROCESSING (NLP)

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "191678_Seqlisting.txt", created on Jan. 11, 2021 and is 4,675 bytes in size. The subject matter of the Sequence Listing is incorporated herein in its entirety by reference.

TECHNICAL FIELD

The present disclosure generally relates to apparatuses, systems and methods to extract meaning from deoxyribonucleic acid (DNA) sequence data. More particularly, the present disclosure relates to identification of genetic elements using natural language processing (NLP).

BACKGROUND

Biological traits of all living organisms are determined by a respective genetic makeup of each organism along with an interaction between the organism and a respective environment. The genetic makeup of any given organism is often referred to as the organism's genome. A genome of each plant and each animal is made of deoxyribonucleic acid (DNA). The genome contains genes (e.g., a region of DNA that may carry instructions for making proteins). It is these proteins that give the plant or animal its biological traits.

For example, color of flowers is determined by genes that carry instructions for making proteins involved in producing the pigments that color petals. Drought is a major threat to, for example, maize yield, especially in subtropical production. Understanding genes and regulatory mechanisms of drought tolerance is important to sustain associated crop yield. Development of plants that, for example, help farmers sustainably increase crop yield and quality is desirable. For example, fungicides, insecticides, herbicides and seed treatments may ensure that crops grow healthier, stronger and more resistant to stress factors, such as heat or drought.

Cis-regulatory elements (CREs) are regions of non-coding DNA which regulate a transcription of neighboring genes. Transcriptional regulators (e.g., upstream transcriptional regulators) define a means by which a cell regulates conversion of DNA to RNA (transcription), thereby, orchestrating gene activity. Ribonucleic acid (RNA) is a nucleic acid present in all living cells. RNA's principal role is to act as a messenger carrying instructions from DNA for controlling synthesis of proteins. An expression Genome-Wide Association Study (eGWAS) is an approach used in genetics research to associate specific genetic variations with particular biological traits.

Analysis of deoxyribonucleic acid (DNA) is often used in plant development. Indeed, correlating biological traits of plants and animals with respective plant or animal DNA and RNA sequences, or portions of respective DNA and RNA sequences, has long been desirable. Conventional computational approaches for gene analysis, using machine learning (ML) methods, typically focus on improving performance of a single model for a given task. Apparatuses, systems, and methods are needed that combine outputs from multiple models that use different pre-processing approaches and different ML methods to infer biological significance.

Natural language processing (NLP) is an area of artificial intelligence focused on using deep learning methods to understand human language. For example, NLP has been applied to a variety of tasks ranging from improvement of search engine queries, sentiment analysis, speech recognition, etc. However, there are only a few instances where NLP has been applied in analysis of DNA sequences. In fact, NLP is an area of artificial intelligence typically focused on using deep learning methods to understand human language.

Apparatuses, systems and methods are needed that may implement a natural language processing (NLP) algorithm to identify Cis-regulatory elements (e.g., novel drought-responsive cis-regulatory elements (DREs)). Apparatuses, systems and methods are also needed that implement a natural language processing (NLP) algorithm and expression GWAS (eGWAS) data to, for example, identify transcriptional regulators (e.g., upstream transcriptional regulators associated with novel drought-responsive cis-regulatory elements (DREs)).

SUMMARY

An apparatus for identifying genetic elements may include a deoxyribonucleic acid (DNA) sequence data receiving module stored on a memory that, when executed by a processor, may cause the processor to receive DNA sequence data. The apparatus may also include a first machine learning model module stored on the memory that, when executed by the processor, may cause the processor to generate first machine learning model output data based on the DNA sequence data. The apparatus may further include a second machine learning model module stored on the memory that, when executed by the processor, may cause the processor to generate second machine learning model output data based on the DNA sequence data. The apparatus may yet further include an optimization model module stored on the memory that, when executed by the processor causes the processor to identify at least one genetic element based on the first machine learning model output data and the second machine learning model output data.

In another embodiment, a computer-implemented method for identifying genetic elements may include receiving, at a processor of a computing device, DNA sequence data in response to the processor executing a deoxyribonucleic acid (DNA) sequence data receiving module. The computer-implemented method may also include generating, using the processor, first machine learning model output data based on the DNA sequence data in response to the processor executing a first machine learning model module. The computer-implemented method may further include generating, using the processor, second machine learning model output data based on the DNA sequence data in response to the processor executing a second machine learning model module. The computer-implemented method may also include identifying, using the processor, at least one genetic element based on the first machine learning model output data and the second machine learning model output data in response to the processor executing an optimization model module.

In a further embodiment, a computer-readable medium storing computer-readable instructions that, when executed by a processor, cause the processor to identify genetic elements. The computer-readable medium may include a deoxyribonucleic acid (DNA) sequence data receiving module that, when executed by a processor, may cause the processor to receive DNA sequence data. The computer-readable medium may also include a first machine learning model module that, when executed by the processor, may cause the processor to generate first machine learning model output data based on the DNA sequence data. The computer-readable medium may further include a second machine learning model module that, when executed by the processor, may cause the processor to generate second machine learning model output data based on the DNA sequence data. The computer-readable medium may yet further include an optimization model module that, when executed by the processor, may cause the processor to identify at least one genetic element based on the first machine learning model output data and the second machine learning model output data.

BRIEF DESCRIPTION OF THE FIGURES

The Figures described below depict various aspects of computer-implemented methods, systems comprising computer-readable media, and electronic devices disclosed therein. It should be understood that each Figure depicts an embodiment of a particular aspect of the disclosed methods, media, and devices, and that each of the figures is intended to accord with a possible embodiment thereof. Further, wherever possible, the following description refers to the reference numerals included in the following Figures, in which features depicted in multiple Figures are designated with consistent reference numerals. The present embodiments are not limited to the precise arrangements and instrumentalities shown in the Figures.

Figure 1:
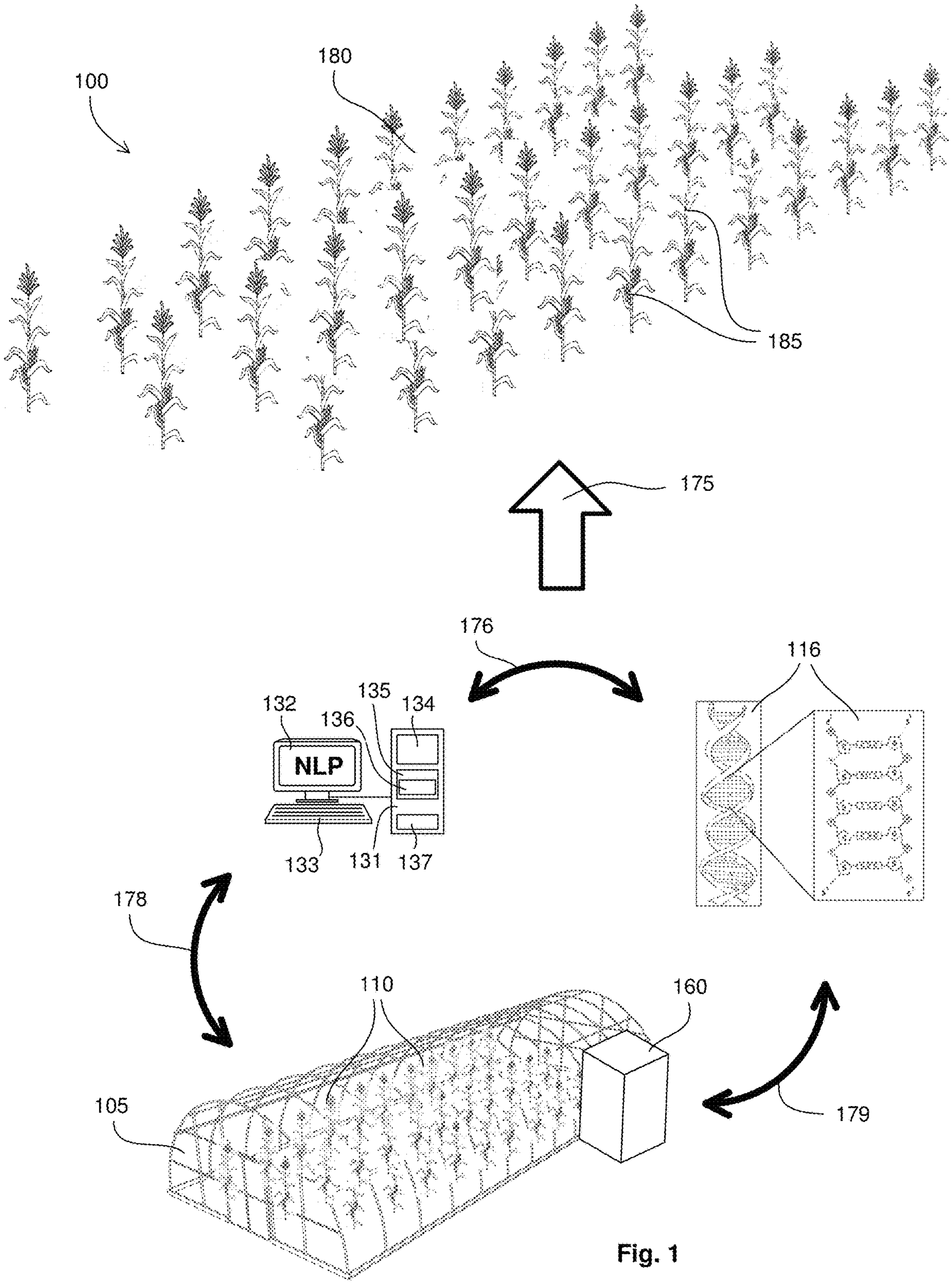
FIG. 1 depicts an example biological management system.

The Figures depict aspects of the present disclosure for purposes of illustration only. One skilled in the art will readily recognize from the following discussion that alternate aspects of the structures and methods illustrated herein may be employed without departing from the principles of the disclosure described herein.

DETAIL DESCRIPTION

Apparatuses, systems, and methods are provided for extracting meaning from deoxyribonucleic acid (DNA) sequence data using natural language processing (NLP). More specifically, the apparatuses, systems, and methods of the present disclosure may implement NLP to identify at least one genetic element within subject DNA sequence data. As used herein, the term "genetic element" may include, for example, a DNA sequence, a DNA subsequence, a gene having a desired function, a Cis-regulatory element, transcriptional regulators, a regulatory element, a promoter, an enhancer, expression of a gene under varying conditions, expression of genes across genotypes, expression of alleles across genotypes, expression of haplotypes across genotypes, expression of genes across cell types, expression of alleles across cell types, expression of haplotypes across cell types, expression of genes across tissue types, expression of alleles across tissue types, expression of haplotypes across tissue types, etc.

Conventional computational approaches for gene analysis, using machine learning (ML) methods, typically focus on improving performance of a single model for a given task. In contrast, the apparatuses, systems, and methods of the present disclosure may combine outputs from multiple models that use different pre-processing approaches and different ML methods to infer biological significance. Oftentimes, outputs derived from ML methods are difficult to interpret. There may be significant variability of output depending on many different factors based on model development.

The apparatuses, systems, and methods of the present disclosure may overcome these challenges by, for example, developing models that focus on increasing true positive rates and decreasing false positive rates as well as combining the output from many different models, using natural language processing, to mitigate effects of variability between models to ultimately infer biological significance of a given k-mer. As a specific example described in detail herein, the apparatuses, systems, and methods of the present disclosure may generate fifteen different models, and may employ a k-mer prioritization script based on k-mer weights output by each model as well as model performance to identify k-mers having a high confidence of being associated with a biological function.

To identify important genetic elements of a biological sequence, other approaches employ statistical tests, classifier feature weights of k-mers, or gradient based analysis of nucleotide importance in convolutional neural networks. In contrast, the apparatuses, systems, and methods of the present disclosure may adapt analysis methods from natural language processing (e.g., attention), and may additionally adapt gradient-based methods to analyze the importance of whole k-mers.

The apparatuses, systems, and methods of the present disclosure may identify DNA motifs that have high confidence for being biologically relevant. Therefore, the identified genetic elements are more likely to function as predicted in a biological context. Accordingly, the apparatuses, systems, and methods of the present disclosure may enable scientists to test fewer sequences empirically to identify a DNA sequence that elicits the desired response in vivo.

As mentioned above, natural language processing (NLP) is an area of artificial intelligence often focused on using deep learning methods to understand human language and infer meaning from words and sentences in large documents of text, etc. However, there are only a few instances where NLP has been applied in analysis of DNA sequences. In fact, processing a long letter sequence (e.g., a DNA sequence) by computer (e.g., using logisti regression, neural networks, etc.) may be inefficient and/or unreliable.

In order to efficiently process DNA sequence data, and reliably extract meaning from the DNA sequence data using NLP, the apparatuses, systems, and methods of the present disclosure may preprocess the DNA sequence data using, for example, a multitude of machine learning models, to generate NLP input data. As described in detail herein, generating NLP input data may include segmenting DNA sequences into DNA subsequences, and performing word embedding on the DNA subsequences. As further described herein, extracting meaning from the NLP input data using NLP is more reliable compared to extracting meaning from the DNA sequence data directly using NLP. Similarly, processing the NLP input data using NLP is more efficient compared to processing the DNA sequence data directly using NLP. Accordingly, the apparatuses, systems, and methods of the present disclosure may take advantage of NLP benefits to extract meaning from DNA sequence data while overcome related deficiencies (e.g., variability, computational inefficiencies, etc.).

As a specific example, discussed throughout the present disclosure for illustrative purposes, drought-responsive elements (DREs) in maize may be identified. In this example, a drought-responsive element (DRE) is a Cis-regulatory element. Associated promoter sequences may be classified as to whether or not the promoter sequences are drought responsive. Associated motifs (i.e., drought-responsive elements) within the promoter sequences may be identified. Natural language processing (NLP) may be used for identification of Cis-regulatory elements and, combined with expression genome-wide association study (eGWAS) data (or MAGIC, Structured NAM, or other forms of multi-parental segregating populations), for identification of upstream transcriptional regulators.

With reference to FIG. 1, a biological management system 100 may include a plurality of plants 110 (e.g., plant representative of a three-hundred maize line association panel) within a greenhouse environment 105, and a greenhouse computing device 160. The greenhouse computing 160 device may, for example, generate and/or receive plant data 116 including: 1) DNA sequence data from, for example, whole genome sequencing, and RNA-seq data (e.g., whole genome sequencing and RNA-seq data for two-hundred and forty-seven maize genotypes), and physiological measurements of an effect of two sequentially applied treatments (e.g., a pre-drought treatment and a moderate drought treatment); and 2) reference genome data (e.g., a B73 maize reference genome data). Reference genome data (also known as reference assembly data) may include digital DNA sequence data that may be an example representation of a set of genes in one idealized individual organism of a species (e.g., B73 maize). As described elsewhere herein, the reference genome data, or more generally, the plant data 116 may be received from a biological data site (e.g., biological data site 205 of FIG. 2).

The greenhouse computing device 160 may receive plant data 116 that is representative of plants 110 being sampled at 17 days after planting (dap), under well-watered conditions (>75% water holding capacity (WHC)), as "pre-drought" samples. The greenhouse computing device 160 may also receive plant data that is representative of plants then being exposed to moderate drought stress (25-35% WHC) starting at 17 dap until plants reached 29-32 dap, and sampled ("moderate-drought" samples). The greenhouse computing device 160 may also receive plant data that is representative of the plants 110 then be allowed to recover from the drought stress under well-watered conditions (>75% WHC) for approximately three days, and sampled at 30-33 dap ("recovery" samples). The greenhouse computing device 160 may further receive plant data 116 that is representative of the plants 110 then being given a subsequent severe drought treatment (10%-20% WHC) for approximately eight days, and sampled at 38-40 dap ("severe drought" samples).

Plant data 116 may include RNA-seq transcriptomic (TxP) data from pre-drought and moderate drought samples. RNA-Seq is a leading technology for analyzing gene expression on a global scale across a broad spectrum of sample types. RNA-seq may be used to quantifying and comparing gene expressions, and for differential expression (DE) detection. An RNA-Seq workflow at a gene level is also available as Bioconductor package rnaseqGene. Bioconductor is a free, open source and open development software project for analysis and comprehension of genomic data generated by wet lab experiments in molecular biology. Bioconductor may be based primarily on statistical R programming language, however, may contain contributions in other programming languages. RNA-seq may, for example, read from a dataset that is mapped to a reference transcriptome (Maize reference genome, version AGPv4). A transcriptome may include a set of all RNA transcripts, including coding and non-coding, in an individual or a population of cells. The term can also sometimes be used to refer to all RNAs, or mRNA alone, depending on the particular experiment. Gene-level counts may be generated using a tximport package in R.

The biological management system 100 may also include a natural language processing (NLP) computing device 131. The NLP computing device 131 may include a processor 134, a memory 135 having at least on set of computer-readable instructions 136 stored thereon and associated with natural language processing of DNA sequence data, a network adapter 137 a display 132 and a keyboard 133. As illustrated in FIG. 1, the NLP computing device 131 and the greenhouse computing device 160 may be communicatively interconnected to one another to transmit and/or receive plant data 116 via paths 176, 178, 179.

The biological management system 100 may further include a crop 185 (e.g., drought-resistant maize) planted and/or growing within a field 180. The crop 185 may incorporate DNA/biological traits 175 identified via, for example, the NLP computing device 131 and/or the greenhouse computing device 160.

Figure 2:
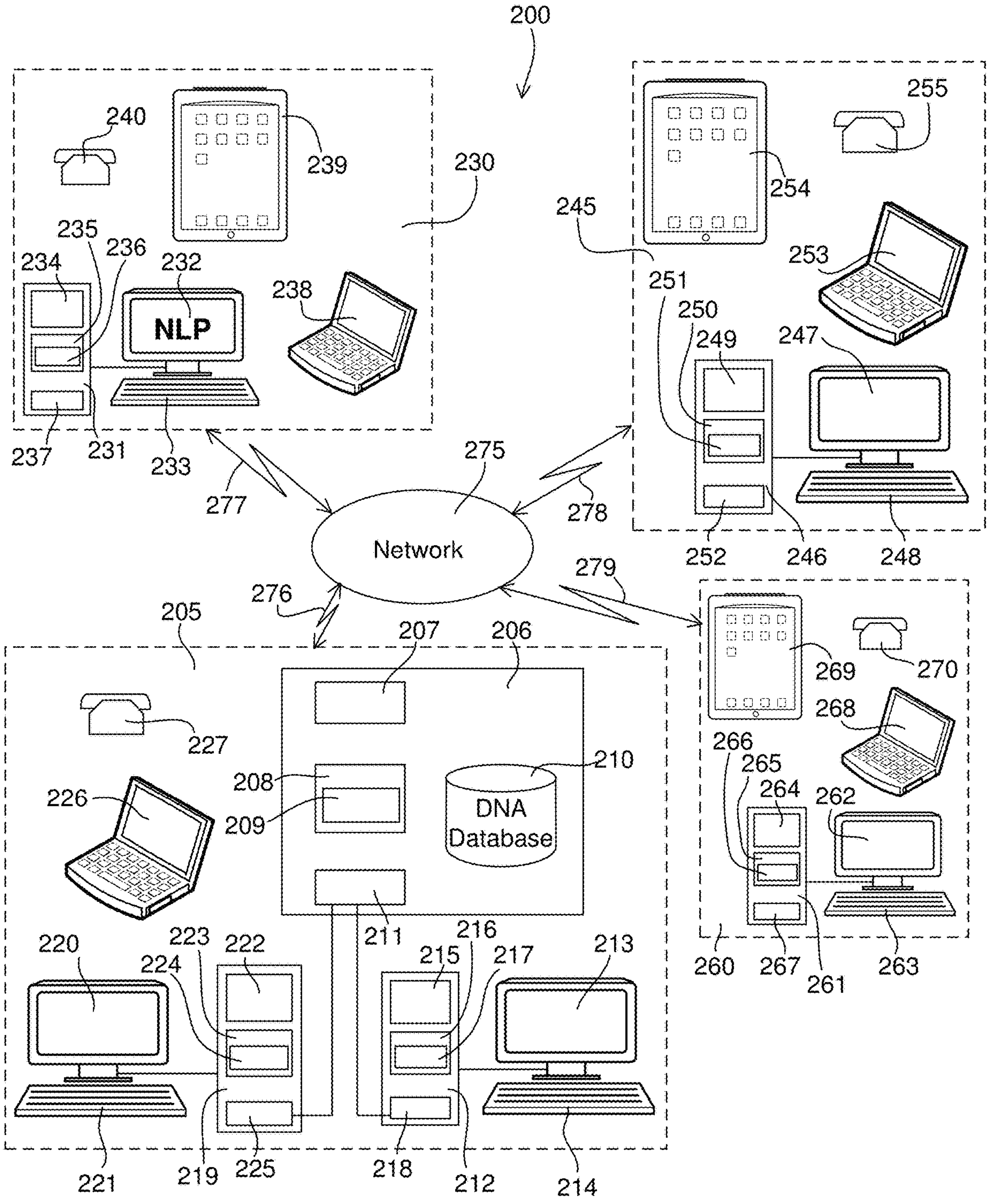
FIG. 2 depicts a high level block diagram of an example computing system for identifying known and/or novel cis-regulatory elements and associated transcriptional regulators.

Turning to FIG. 2, a computing system for identifying cis-regulatory elements (e.g., known and/or novel cis-regulatory elements) and associated transcriptional regulators 200 may include a biological data center 205 and a natural language processing (NLP) site 230 communicatively couple via a communications network 275. The computer system 200 may also include a computational and data analytics site 245 and a greenhouse site 260. While, for convenience of illustration, only a single biological data center 205 is depicted within the computer system 200 of FIG. 2, any number of biological data centers 205 may be included within the computer system 200. While, for convenience of illustration, only a single natural language processing (NLP) site 230 is depicted within the computer system 200 of FIG. 2, any number of natural language processing (NLP) sites 230 may be included may be included within the computer system 200. Indeed, the computer system 200 may accommodate thousands of natural language processing (NLP) sites 230.

DNA sequence data may be more efficient by distributing related data storage and/or processing among respective computing device located at the biological data center 205, the natural language processing (NLP) site 230, the computational and data analytics site 245, and/or the greenhouse site 260 compared to known computing devices and systems. Similarly, meaning may be more reliably extracted from the DNA sequence data using NLP systems by distributing related data storage and/or processing among respective computing device located at the biological data center 205, the natural language processing (NLP) site 230, the computational and data analytics site 245, and/or the greenhouse site 260 compared to known computing devices and systems.

While, for convenience of illustration, only a single computational and data analytics site 245 is depicted within the computer system 200 of FIG. 2, any number of computational and data analytics sites 245 may be included within the computer system 200. Any given computational and data analytics site 245 may be a mobile site. While, for convenience of illustration, only a single greenhouse site 260 is depicted within the computer system 200 of FIG. 2, any number of greenhouse sites 260 may be included within the computer system 200.

The communications network 275, any one of the network adapters 211, 218, 225, 237, 252, 267 and any one of the network connections 276, 277, 278, 279 may include a hardwired section, a fiber-optic section, a coaxial section, a wireless section, any sub-combination thereof or any combination thereof, including for example a wireless LAN, MAN or WAN, WiFi, WiMax, the Internet, a Bluetooth connection, or any combination thereof. Moreover, a biological data center 205, a natural language processing (NLP) site 230, a computational and data analytics site 245 and/or a greenhouse site 260 may be communicatively connected via any suitable communication system, such as via any publicly available or privately owned communication network, including those that use wireless communication structures, such as wireless communication networks, including for example, wireless LANs and WANs, satellite and cellular telephone communication systems, etc.

Any given biological data center 205 may include a mainframe, or central server, system 206, a server terminal 212, a desktop computer 219, a laptop computer 226 and a telephone 227. While the biological data center 205 of FIG. 2 is shown to include only one mainframe, or central server, system 206, only one server terminal 212, only one desktop computer 219, only one laptop computer 226 and only one telephone 227, any given biological data center 205 may include any number of mainframe, or central server, systems 206, server terminals 212, desktop terminals 219, laptop computers 226 and telephones 227. Any given telephone 227 may be, for example, a land-line connected telephone, a computer configured with voice over internet protocol (VOIP), or a mobile telephone (e.g., a smartphone).

Any given server terminal 212 may include a processor 215, a memory 216 having at least on set of computer-readable instructions 217 stored thereon, and associated with natural language processing of DNA sequence data, a network adapter 218 a display 213 and a keyboard 214. Any given desktop computer 219 may include a processor 222, a memory 223 having at least on set of computer-readable instructions 224 stored thereon and associated with natural language processing of DNA sequence data, a network adapter 225 a display 220 and a keyboard 221. Any given mainframe, or central server, system 206 may include a processor 207, a memory 208 having at least on set of computer-readable instructions 209, and associated with natural language processing of DNA sequence data, a network adapter 211 and a customer (or client) database 210. Any given lap top computer 226 may include a processor, a memory having at least on set of computer-readable instructions stored thereon, and associated with natural language processing of DNA sequence data, a network adapter, a display and a keyboard. Any given telephone 227 may include a processor, a memory having at least on set of computer-readable instructions stored thereon and associated with natural language processing of DNA sequence data, a display and a keyboard.

Any given natural language processing (NLP) site 230 may include a desktop computer 231, a lap top computer 238, a tablet computer 239 and a telephone 240. While only one desktop computer 231, only one lap top computer 238, only one tablet computer 239 and only one telephone 240 is depicted in FIG. 2, any number of desktop computers 231, lap top computers 238, tablet computers 239 and/or telephones 240 may be included at any given natural language processing (NLP) site 230. Any given telephone 240 may be a land-line connected telephone or a mobile telephone (e.g., smartphone). Any given desktop computer 231 may include a processor 234, a memory 235 having at least on set of computer-readable instructions stored thereon and associated with natural language processing of DNA sequence data 236, a network adapter 237 a display 232 and a keyboard 233. Any given lap top computer 238 may include a processor, a memory having at least on set of computer-readable instructions stored thereon and associated with natural language processing of DNA sequence data, a network adapter, a display and a keyboard. Any given tablet computer 239 may include a processor, a memory having at least on set of computer-readable instructions stored thereon and associated with natural language processing of DNA sequence data, a network adapter, a display and a keyboard. Any given telephone 240 may include a processor, a memory having at least on set of computer-readable instructions stored thereon and associated with natural language processing of DNA sequence data, a network adapter, a display and a keyboard.

Any given computational and data analytics site 245 may include a desktop computer 246, a lap top computer 253, a tablet computer 254 and a telephone 255. While only one desktop computer 246, only one lap top computer 253, only one tablet computer 254 and only one telephone 255 is depicted in FIG. 2, any number of desktop computers 246, lap top computers 253, tablet computers 254 and/or telephones 255 may be included at any given computational and data analytics site 245. Any given telephone 255 may be a land-line connected telephone or a mobile telephone (e.g., smartphone). Any given desktop computer 246 may include a processor 249, a memory 250 having at least on set of computer-readable instructions 251 stored thereon and associated with natural language processing of DNA sequence data, a network adapter 252 a display 247 and a keyboard 248. Any given lap top computer 253 may include a processor, a memory having at least on set of computer-readable instructions stored thereon and associated with natural language processing of DNA sequence data, a network adapter, a display and a keyboard. Any given tablet computer 254 may include a processor, a memory having at least on set of computer-readable instructions stored thereon and associated with natural language processing of DNA sequence data, a network adapter, a display and a keyboard. Any given telephone 255 may include a processor, a memory having at least on set of computer-readable instructions stored thereon and associated with natural language processing of DNA sequence data, a network adapter, a display and a keyboard.

Any given greenhouse site 260 may include a desktop computer 261, a lap top computer 268, a tablet computer 269 and a telephone 270. While only one desktop computer 261, only one lap top computer 268, only one tablet computer 269 and only one telephone 270 is depicted in FIG. 2, any number of desktop computers 261, lap top computers 268, tablet computers 269 and/or telephones 270 may be included at any given greenhouse site 260. Any given telephone 270 may be a land-line connected telephone or a mobile telephone (e.g., smartphone). Any given desktop computer 261 may include a processor 264, a memory 265 having at least on set of computer-readable instructions 266 stored thereon and associated with natural language processing of DNA sequence data, a network adapter 267 a display 262 and a keyboard 263. Any given lap top computer 268 may include a processor, a memory having at least on set of computer-readable instructions stored thereon and associated with natural language processing of DNA sequence data, a network adapter, a display and a keyboard. Any given tablet computer 269 may include a processor, a memory having at least on set of computer-readable instructions stored thereon and associated with natural language processing of DNA sequence data, a network adapter, a display and a keyboard. Any given telephone 270 may include a processor, a memory having at least on set of computer-readable instructions stored thereon and associated with natural language processing of DNA sequence data, a network adapter, a display and a keyboard.

Figure 3A:
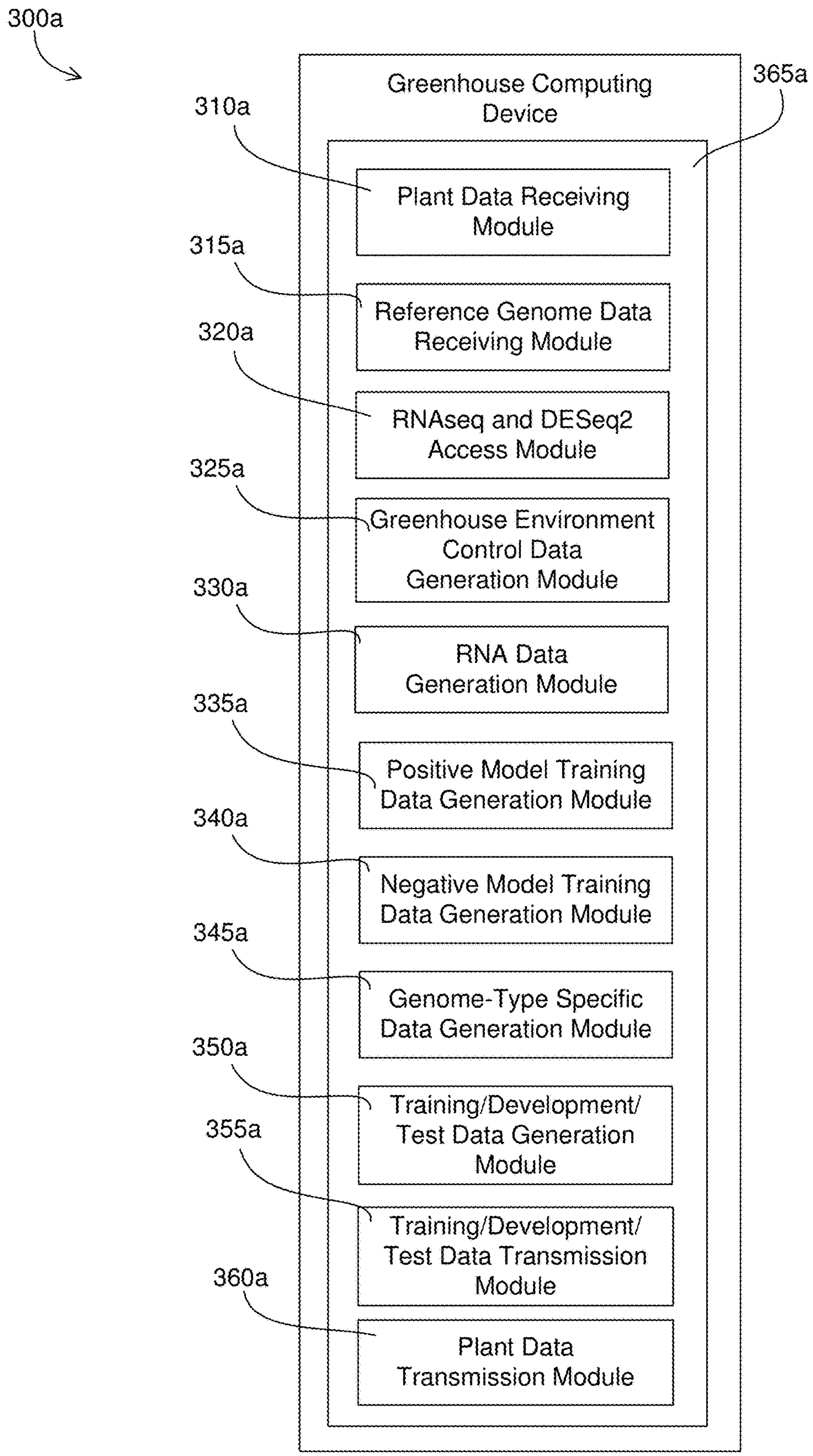
FIGS. 3A and 3B depict an example greenhouse computing device and an example method of implementation.
Figure 3B:
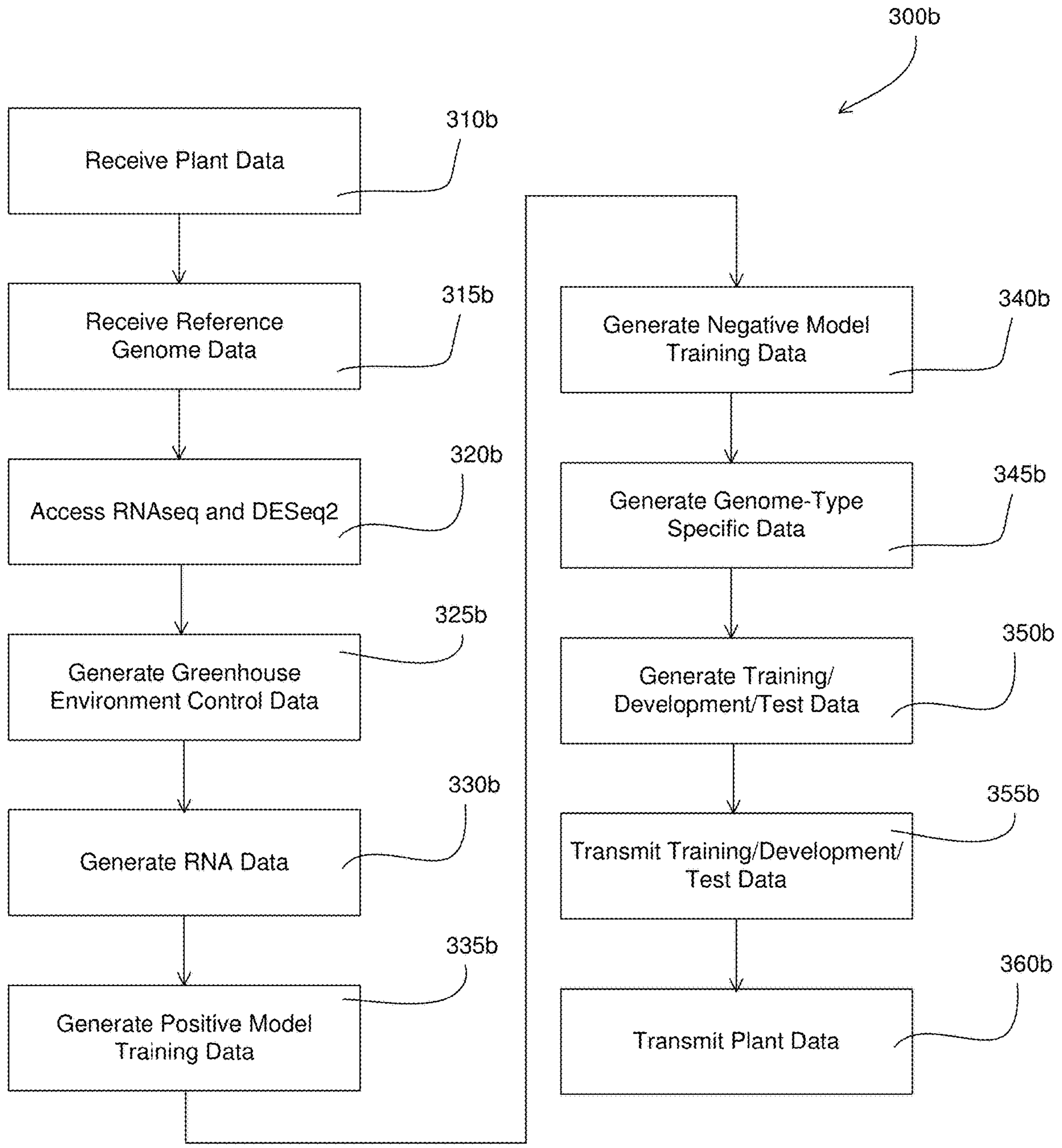

With reference to FIGS. 3A and 3B, a greenhouse computing device 300*a* may include a plant data receiving module 310*a*, a reference genome data receiving module 315*a*, a RNAseq and DESeq2 access module 320*a*, a greenhouse environment control data generation module 325*a*, a RNA data generation module 330*a*, a positive model training data generation module 335*a*, a negative model training data generation module 340*a*, a genome-type specific data generation module 345*a*, a training/development/test data generation module 350*a*, a training/development/test data transmission module 355*a*, and a plant data transmission module 360*a* stored on, for example, a memory 365*a*, as a set of computer-readable instructions. The greenhouse computing device 300*a* may be similar to, for example, the greenhouse computing device 160 of FIG. 1, 231, 238, 239, or 240 of FIG. 2. The modules 310*a*-360*a* may be similar to, for example, the module 266 of FIG. 2.

With additional reference to FIG. 3B a method of generating model input data 300*b* may be implemented by a processor (e.g., processor 264 of FIG. 2) executing, for example, at least a portion of the modules 310*a*-360*a* of FIG. 3A. In particular, the processor 264 may execute the plant data receiving module 310*a* to cause the processor 264 to, for example, receive DNA sequence from whole genome sequencing and RNA-seq data associated with a particular plant type (e.g., two-hundred forty-seven maize genotypes) (block 310*b*). The processor 264 may execute the reference genome data receiving module 315*a* to cause the processor 264 to, for example, receive reference genome data (block 315*b*). For example, the processor 264 may receive reference genome data from a biological data computer device (e.g., DNA database 210 of FIG. 2).

The processor 264 may execute the RNAseq and DESeq2 access module 320*a* to cause the processor 264 to, for example, receive physiological measurements of the effect of two sequentially applied treatments (e.g., a pre-drought treatment and moderate drought treatment) (block 320*b*). Concurrent with execution of the RNAseq and DESeq2 access module 320*a*, the processor 264 may execute the greenhouse environmental control data generation module 325*a* to cause the processor 264 to, for example, generate greenhouse environmental control data (block 325*b*). The processor 264 may control an environment inside the greenhouse based upon the greenhouse environmental control data (e.g., produce pre-drought conditions inside the greenhouse and produce moderate drought conditions inside the greenhouse).

The processor 264 may execute the RNA data generation module 330*a* to cause the processor 264 to, for example, generate RNA data using RNAseq and DESeq2 (block 330*b*). RNAseq may use next-generation sequencing to reveal a presence and quantity of RNA in a biological sample at a given moment by, for example, analyzing an associated continuously changing cellular transcriptome. DESeq2 may provide methods to test for differential expression by use of, for example, negative binomial generalized linear models. Estimates of dispersion and logarithmic fold changes may incorporate data-driven prior distributions.

The processor 264 may execute the positive model training data generation module 335*a* to cause the processor 264 to, for example, generate positive model training data (block 335*b*). The processor 264 may execute the negative model training data generation module 340*a* to cause the processor 264 to, for example, generate negative model training data (block 340*b*). The processor 264 may execute the genome-type specific data generation module 345*a* to cause the processor 264 to, for example, generate genome-type specific data (block 345*b*).

The processor 264 may execute the training/development/test data generation module 350*a* to cause the processor 264 to, for example, generate training/development/test data (block 350*b*). The processor 264 may execute the training/development/test data transmission module 355*a* to cause the processor 264 to, for example, transmit training/development/test data (block 355*b*). For example, the processor 264 may transmit training/development/test data to a NLP computing device (e.g., NLP computing device 131 of FIG. 1 or 231 of FIG. 2).

The processor 264 may execute the plant data transmission module 360*a* to cause the processor 264 to, for example, transmit plant data (block 360*b*). For example, the processor 264 may transmit plant data to the NLP computing device 131, 231.

Figure 4A:
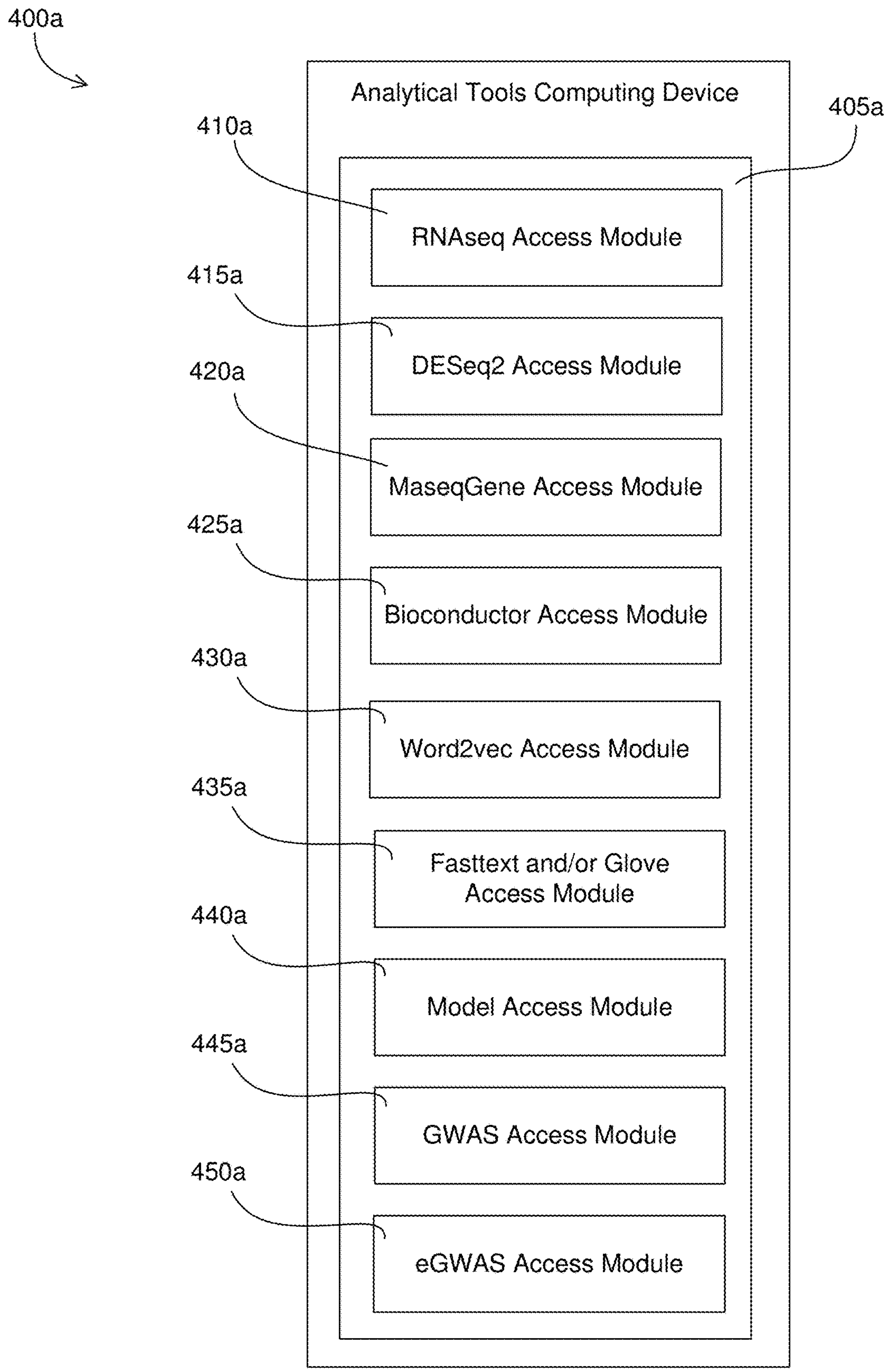
FIGS. 4A and 4B depict an example biological analytical tools computing device and an example method of implementation.
Figure 4B:
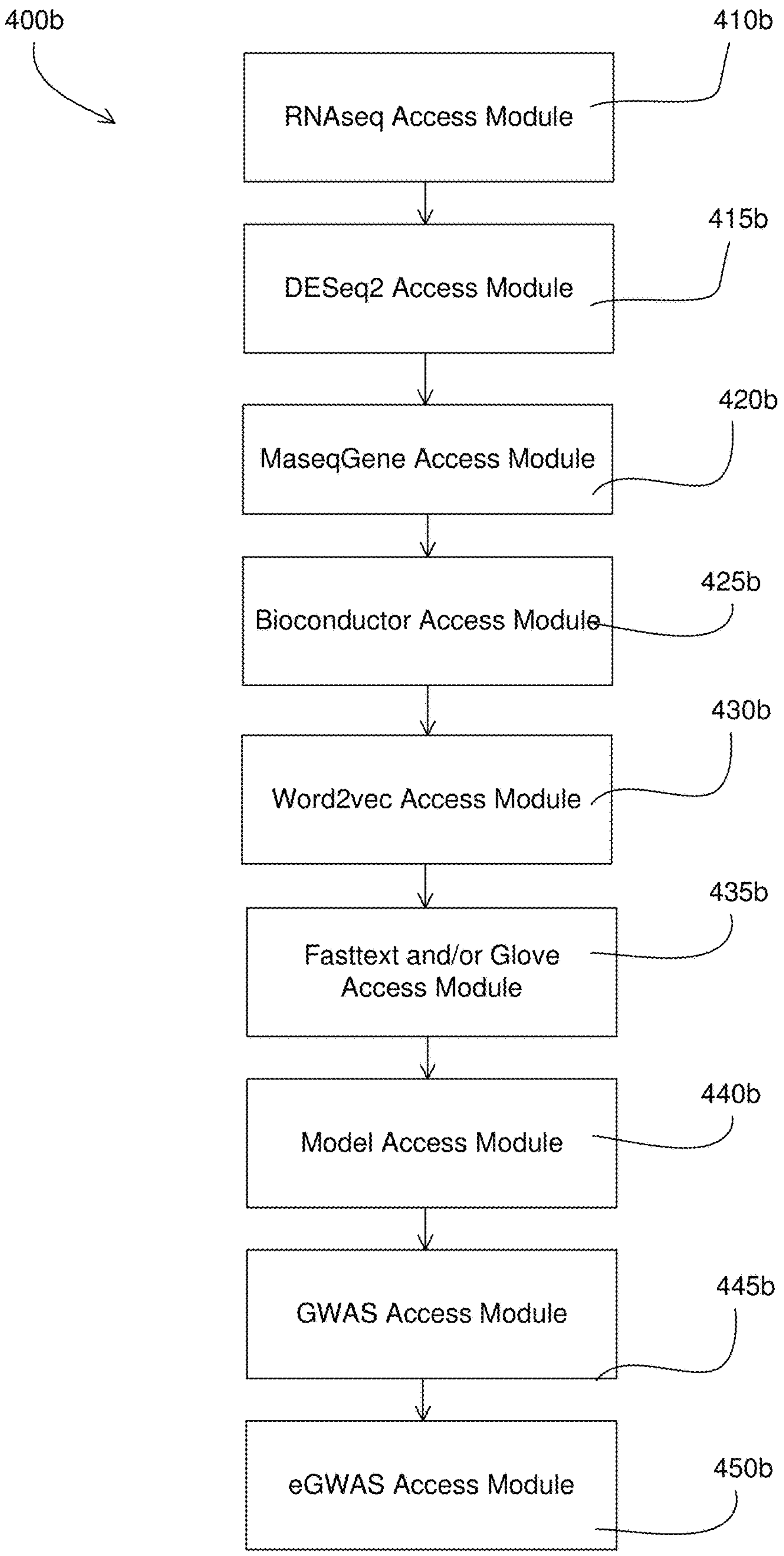

With reference to FIGS. 4A and 4B, a biological analytical tools computing device 400*a* may include a RNAseq access module 410*a*, a DESeq2 (or alternative methods of calculating differential gene expression such as EdgeR or Limma-Voom) access module 415*a*, a rnaseqGene access module 4120*a*, a Bioconductor access module 425*a*, a Word2vec access module 430*a*, a Fasttext/Glove access module 435*a*, a model access module 440*a*, a GWAS access module 445*a*, and a eGWAS access module 450*a*, stored on, for example, a memory 405*a* as a set of computer-readable instructions. The biological analytical tools computing device 400*a* may be similar to, for example, the biological analytical tools computing device 246 of FIG. 2. The modules 410*a*-450*a* may be similar to, for example, module 251 of FIG. 1.

With additional reference to FIG. 4B, a method of operating an analytical tools computing device 400*b* may be implemented by a processor (e.g., processor 249 of FIG. 2) executing, for example, at least a portion of module 251 of FIG. 1 or modules 410*a*-450*a* of FIG. 4A. In particular, the processor 249 may execute the RNAseq access module 410*a* to cause the processor 249 to, for example, facilitate access to the RNAseq tools (block 410*b*). For example, the processor 249 may facilitate greenhouse computing device 160, 261 access the RNAseq tools.

The processor 249 may execute the DESeq2 access module 415*a* to cause the processor 249 to, for example, facilitate access to the DESeq2 tools (block 415*b*). For example, the processor 249 may facilitate greenhouse computing device 160, 261 access the DESeq2 tools. The processor 249 may execute the rnaseqGene access module 420*a* to cause the processor 249 to, for example, facilitate access to the rnaseqGene tools (block 420*b*). For example, the processor 249 may facilitate greenhouse computing device 160, 261 access the rnaseqGene tools.

The processor 249 may execute the Bioconductor access module 425*a* to cause the processor 249 to, for example, facilitate access to the Bioconductor tools (block 425*b*). For example, the processor 249 may facilitate greenhouse computing device 160, 261 and/or NLP computing device 131, 231 access the Bioconductor tools. The processor 249 may execute the Word2vec access module 430*a* to cause the processor 249 to, for example, facilitate access to the Word2vec tools (block 430*b*). For example, the processor 249 may facilitate NLP computing device 131, 231 to access the Word2vec tools.

The processor 249 may execute the Fasttext/Glove access module 435*a* to cause the processor 249 to, for example, facilitate access to the Fasttext/Glove tools (block 435*b*). For example, the processor 249 may facilitate NLP computing device 131, 231 to access the Fasttext/Glove tools. The processor 249 may execute the model access module 440*a* to cause the processor 249 to, for example, facilitate access to the model tools (block 440*b*). For example, the processor 249 may facilitate NLP computing device 131, 231 access the model tools.

The processor 249 may execute the GWAS access module 445*a* to cause the processor 249 to, for example, facilitate access to the GWAS tools (block 445*b*). For example, the processor 249 may facilitate NLP computing device 131, 231 access the GWAS tools. The processor 249 may execute the eGWAS access module 450*a* to cause the processor 249 to, for example, facilitate access to the eGWAS tools (block 450*b*). For example, the processor 249 may facilitate NLP computing device 131, 231 access the eGWAS tools.

Figure 5A:
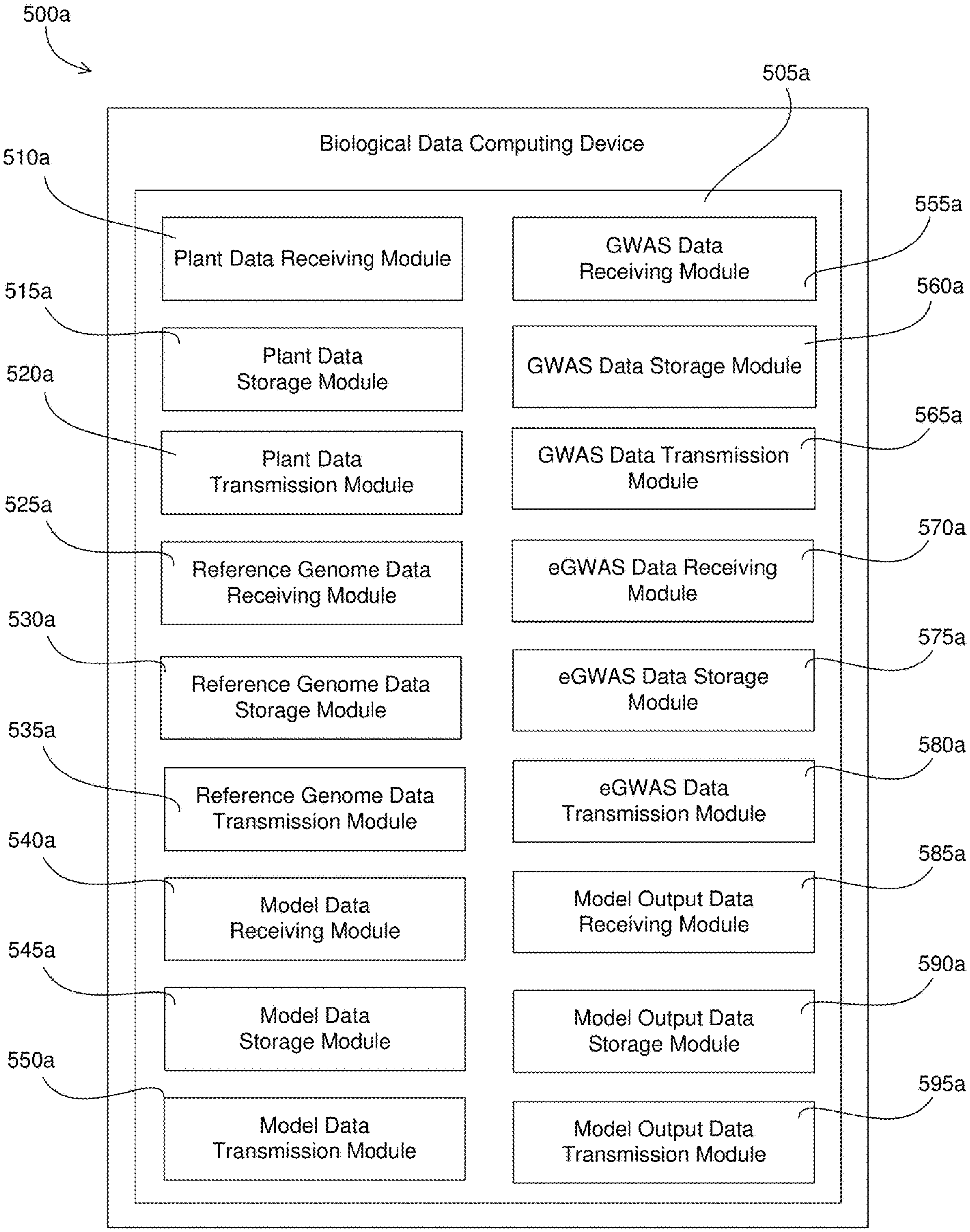
FIGS. 5A and 5B depict an example biological data computing device and an example method of implementation.
Figure 5B:
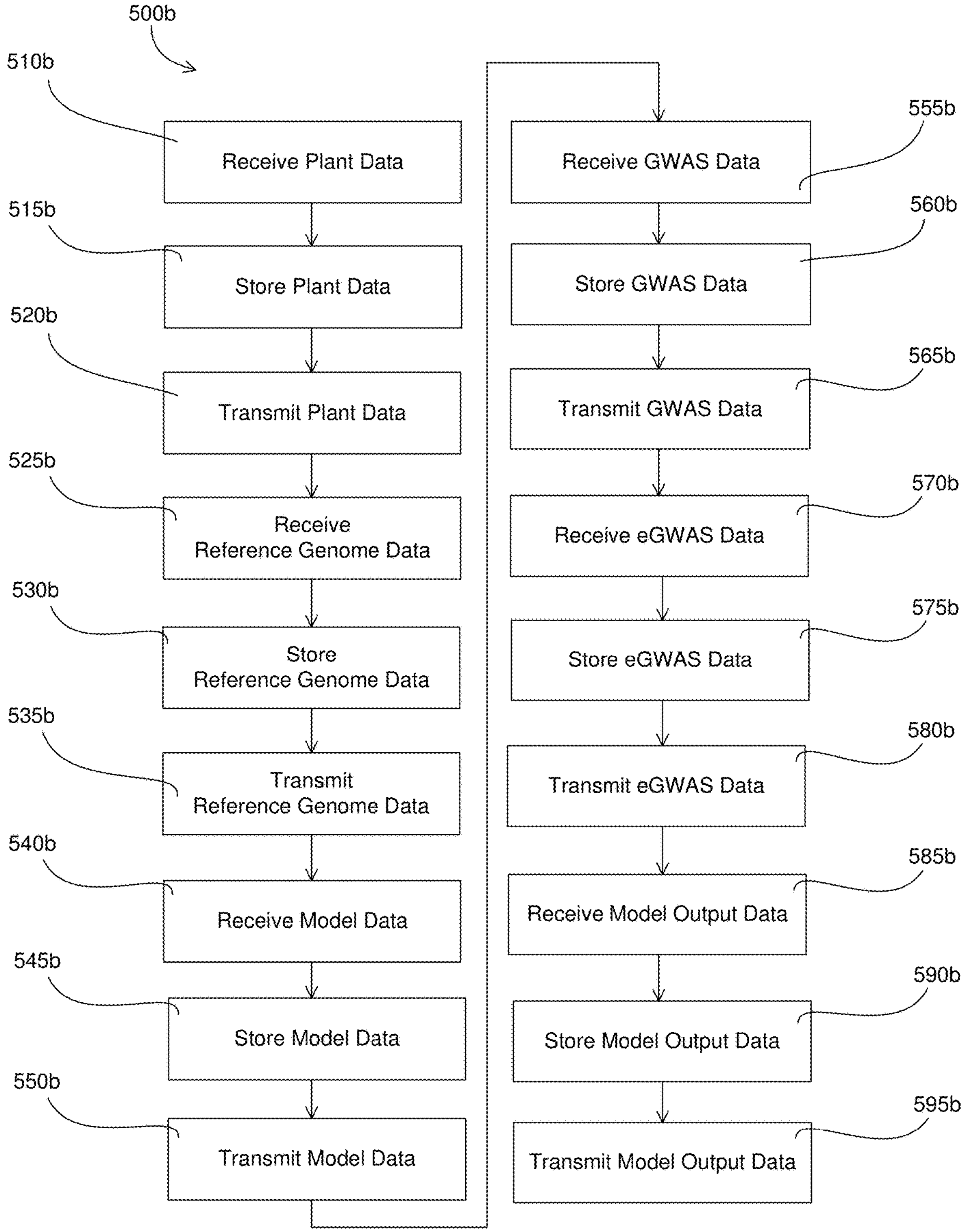

Turning to FIGS. 5A and 5B, a biological data computing device 500*a* may include a plant data receiving module 510*a*, a plant data storage module 515*a*, a plant data transmission module 520*a*, a reference genome data receiving module 525*a*, a reference genome data storage module 530*a*, a reference genome data transmission module 535*a*, a model data receiving module 540*a*, a model data storage module 545*a*, a model data transmission module 550*a*, a GWAS data receiving module 555*a*, a GWAS data storage module 560*a*, a GWAS data transmission module 565*a*, an eGWAS data receiving module 570*a*, an eGWAS data storage module 575*a*, an eGWAS data transmission module 580*a*, a model output data receiving module 585*a*, a model output data storage module 590*a*, and a model output data transmission module 595*a*, stored on, for example, a memory 505*a* as a set of computer-readable instructions. The biological data computing device 500*a* may be similar to, for example, the biological data computing device 206 of FIG. 2. The modules 510*a*-595*a* may be similar to, for example, module 209 of FIG. 1.

With additional reference to FIG. 5B, a method of operating biological data computing device 500*b* may be implemented by a processor (e.g., processor 207 of FIG. 2) executing, for example, at least a portion of module 209 of FIG. 1 or modules 510*a*-595*a* of FIG. 5A. In particular, the processor 207 may execute the plant data receiving module 510*a* to cause the processor 207 to, for example, receive plant data (block 510*b*). For example, the processor 207 may receive plant data from a greenhouse computing device 160, 261.

The processor 207 may execute the plant data storage module 515*a* to cause the processor 207 to, for example, store plant data (block 515*b*). For example, the processor 207 may store plant data in a DNA database (e.g., DNA database 210 of FIG. 2). The processor 207 may execute the plant data transmission module 520*a* to cause the processor 207 to, for example, transmit plant data (block 520*b*). For example, the processor 207 may transmit plant data to a NLP computing device 131, 231.

The processor 207 may execute the reference genome data receiving module 525*a* to cause the processor 207 to, for example, receive reference genome data (block 525*b*). For example, the processor 207 may receive reference genome data from a greenhouse computing device 160, 261. The processor 207 may execute the reference genome data storage module 530*a* to cause the processor 207 to, for example, store reference genome data (block 530*b*). For example, the processor 207 may store reference genome data in a DNA database (e.g., DNA database 210 of FIG. 2). The processor 207 may execute the reference genome data transmission module 535*a* to cause the processor 207 to, for example, transmit reference genome data (block 535*b*). For example, the processor 207 may transmit reference genome data to a NLP computing device 131, 231.

The processor 207 may execute the model data receiving module 540*a* to cause the processor 207 to, for example, receive model data (block 540*b*). For example, the processor 207 may receive model data from a NLP computing device 131, 231. The processor 207 may execute the model data storage module 545*a* to cause the processor 207 to, for example, store model data (block 545*b*). For example, the processor 207 may store model data in a DNA database (e.g., DNA database 210 of FIG. 2). The processor 207 may execute the model data transmission module 550*a* to cause the processor 207 to, for example, transmit model data (block 550*b*). For example, the processor 207 may transmit model data to a NLP computing device 131, 231.

The processor 207 may execute the GWAS data receiving module 555*a* to cause the processor 207 to, for example, receive GWAS data (block 555*b*). For example, the processor 207 may receive GWAS data from a NLP computing device 131, 231. The processor 207 may execute the GWAS data storage module 560*a* to cause the processor 207 to, for example, store GWAS data (block 560*b*). For example, the processor 207 may store GWAS data in a DNA database (e.g., DNA database 210 of FIG. 2). The processor 207 may execute the GWAS data transmission module 565*a* to cause the processor 207 to, for example, transmit GWAS data (block 565*b*). For example, the processor 207 may transmit GWAS data to a NLP computing device 131, 231.

The processor 207 may execute the eGWAS data receiving module 570*a* to cause the processor 207 to, for example, receive eGWAS data (block 570*b*). For example, the processor 207 may receive eGWAS data from a NLP computing device 131, 231. The processor 207 may execute the eGWAS data storage module 575*a* to cause the processor 207 to, for example, store eGWAS data (block 575*b*). For example, the processor 207 may store eGWAS data in a DNA database (e.g., DNA database 210 of FIG. 2). The processor 207 may execute the eGWAS data transmission module 580*a* to cause the processor 207 to, for example, transmit eGWAS data (block 580*b*). For example, the processor 207 may transmit eGWAS data to a NLP computing device 131, 231.

The processor 207 may execute the model output data receiving module 585*a* to cause the processor 207 to, for example, receive model output data (block 585*b*). For example, the processor 207 may receive model output data from a NLP computing device 131, 231. The processor 207 may execute the model output data storage module 590*a* to cause the processor 207 to, for example, store model output data (block 590*b*). For example, the processor 207 may store model output data in a DNA database (e.g., DNA database 210 of FIG. 2). The processor 207 may execute the model output data transmission module 595*a* to cause the processor 207 to, for example, transmit model output data (block 595*b*). For example, the processor 207 may transmit model output data to a NLP computing device 131, 231.

With reference to FIGS. 6A-H, a natural language processing computing device 600*a* may include model input data receiving module 610*a*, a k-mer data generation module 615*a*, a NLP model training data generation module 620*a*, a NLP model data generation module 625*a*, a sequence classification data generation module 630*a*, a Cis-regulatory element data generation module 635*a*, a GWAS data receiving module 640*a*, an eGWAS data receiving module 645*a*, a transcriptional regulatory data generation module 650*a*, a model output data receiving module 655*a*, a novel Cis-regulatory element verification data generation module 660*a*, and a NLP model data transmission module 665*a*, stored on, for example, a memory 605*a* as a set of computer-readable instructions. The NLP computing device 600*a* may be similar to, for example, the NLP computing device 131 of FIG. 1 or 231 of FIG. 2. The modules 610*a*-665*a* may be similar to, for example, module 136 of FIG. 1 or 236 of FIG. 2.

The processor 231 may receive a plant dataset 116 generated by, for example, a research experiment. The plant dataset 116 may be a source of model training data. For example, processor 264 may generate a plant dataset with plants under greenhouse conditions, and may include diverse maize lines (e.g., maize association panel).

The processor 231 may generate a positive model training dataset based on significantly differentially expressed genes (DEGs). The DEGs may be identified in response to drought treatment using DESeq2 within each individual genotype. DEGs that may be significantly upregulated with a log-fold change greater than one (LFC>1), with adjusted p-values of less than 0.05 may be added to a positive training dataset. DESeq2 may provide methods to test for differential expression by use of negative binomial generalized linear models; the estimates of dispersion and logarithmic fold changes incorporate data-driven prior distributions. Differential gene expression analysis based on the negative binomial distribution.

The processor 231 may generate a negative model training dataset based on DESeq2 results calculated for each individual genotype similar to, for example, how a positive training dataset may be generated. Genes that showed LFC<|0.5| with adjusted p-values of >0.9 may be selected as a pool of non-drought responsive genes. A presence of eight known housekeeping genes in a negative DRE training set, of which, all eight housekeeping genes may be present, may be used as a control dataset. For example, non-redundant genes, from a non-drought responsive pool for each genotype, may be combined to result in 22,279 genes in an associated negative training set. Of the set of non-drought responsive genes identified from each genotype, 200 genes may be randomly selected to be included in the negative training data.

The positive and/or negative data may include a list of labeled sequences. Each item (s,) in the list may consist of a DNA subsequence s (of length 3000 nt) of a respective gene's promoter region, and a label (1 if s's promoter region regulates a gene that is differentially expressed with respect to drought, 0 otherwise)). The data may be split into training, development and testing (70%, 15%, 15%). Alternatively, a five-fold cross-validation split may be created. In at least some circumstances, there may not be gene overlap between the splits.

Training a NLP model may include a weights optimizing process in which an error of predictions is minimized and the network reaches a specified level of accuracy. A method mostly used to determine an error contribution of each neuron is called backpropagation that may include calculation of a gradient of a loss function. It is possible to make a NLP system more flexible and more powerful by using additional hidden layers. Artificial neural networks (e.g., a NLP model) with multiple hidden layers between the input and output layers are called deep neural networks (DNNs). DNNs may model complex nonlinear relationships.

Reference genome data (e.g., a B73 maize reference genome) may be used to learn distributed representations of k-mers ("word embeddings"). A byte-pair encoding scheme may be derived using the reference genome data. Furthermore, coding sequences from the reference genome data may be used as, for example, "background knowledge" for classifying a corresponding promoter sequences.

To obtain genotype-specific sequences, whole genome sequencing data from, for example, two-hundred forty-seven diverse maize lines may be used to make variant calls. Overall, sequencing coverage may be low. Therefore, a single nucleotide polymorphisms (SNP) or insertion/deletion polymorphism (INDEL) may be considered a true sequence change when the data includes a high confidence interval. Genotype-specific promoter sequences (i.e., defined as 3 kb upstream of the coding sequence) may be used in both positive and negative training datasets. SNPs (pronounced "snips") may be, for example, a most common type of genetic variation. An INDEL may be a type of genetic variation in which a specific nucleotide sequence is present (insertion) or absent (deletion). While not as common as SNPs, INDELSs may be widely spread across an associated genome.

The processor 231 may implement a method of generating a training dataset, a development dataset, and a testing data, based upon a set of maize DNA sequences, may include: receiving 1) plant data, and 2) reference genome data (e.g., a B73 maize reference genome data), and may generate positive and negative data based on the plant data. The plant data may contain data that is representative of DNA sequence from whole genome sequencing and RNA-seq data (e.g., DNA sequence from whole genome sequencing and RNA-seq data for two-hundred forty-seven maize genotypes, and physiological measurements of the effect of two sequentially applied treatments (i.e., a pre-drought treatment and moderate drought treatment)). Positive and negative data may include: a list of labeled sequences, each item (s, l) in the list may consist of a DNA subsequence s (of length 3000 nt) of some gene's promoter region, and a label l (e.g., 1 if s's promoter region regulates a gene that is differentially expressed with respect to drought, 0 otherwise). The list of labeled sequences may be split into a training dataset, a development dataset, and a testing dataset (e.g., 70%, 15%, 15%, respectively), and a five-fold cross-validation split may also be generated. The split list of labeled sequences may not include gene overlap between the splits. A split list of labeled sequences dataset may be used to, for example, identify distributed representations of k-mers ("word embeddings"). For example, a byte-pair encoding scheme may be derived using the split list of labeled sequences dataset. Furthermore, coding sequences from a split list of labeled sequences dataset may be used as "background knowledge" for classifying corresponding promoter sequences.

To make model input data (i.e., data representative of DNA sequences) accessible to natural language processing algorithms, the DNA sequences may be represented as "words" and/or "sentences."

The plant data may be preprocessed using k-mers with high overlap. For example, a DNA sequence may be segmented as follows: for a given k, a sliding window (slide typically 1) of length k moves over the sequence. This may yield a list of highly overlapping k-mers. A list of highly overlapping k-mers may be used to represent the DNA sequence. An advantage of using a list of highly overlapping k-mers is that the list may yield a large amount of data (i.e., in the order of magnitude of the length of the input sequence). A disadvantage of using a list of highly overlapping k-mers is with respect to a correspondingly high overlap of neighboring k-mers. While high overlap of neighboring k-mers may be beneficial for transcript mapping, high overlap of neighboring k-mers may affect performance of NLP (i.e., NLP may not be designed for processing "sentences" where neighboring "words" have such a large overlap in meaning).

The plant data may be preprocessed via copying using a sliding window. For example, for a given k, a sliding window of length k and with slide k may be moved over a DNA sequence. Copying via sliding window may be repeated by starting the sliding and different points in the beginning (i.e., the first k positions). Copying via sliding window may yield k "sentences", where each sentence is already segmented into non-overlapping k-mers. The segmented sentences may represent the DNA sequence. A segmented sentence representation of a DNA sequence may be, for example, highly redundant. High redundancy may be an advantage, since high redundancy may increase associated training data. Moreover, varying an associated starting point, may eliminate an influence of an arbitrary chosen starting point (https://www.ncbi.nlm.nih.gov/pmc/articles/PMC5406869/). However, varying an associated starting point may lead to high "meaning" overlap in "sentences" for the same "document," which may negatively impact performance.

The plant data may be preprocessed by splitting input DNA sequences by characters. For example, the sequence GATTA may be represented as the list [G, A, T, T, A]. Splitting of an input sequence may result in a natural representation. A resulting split may not introduce artificial meaning overlap. Splitting of input sequences may lead to long input lengths (e.g., input lengths >=3000). Long input lengths may pose difficulties during NLP model learning optimization, as state-of-the-art NLP model methods may not be designed to process long input sequences.

The plant data may be preprocessed by segmenting the input DNA sequences into non-overlapping k-mers for a fixed k. Non-overlapping k-mer segmentation may yield a representation suitable for natural language processing algorithms, non-overlapping k-mer segmentation may be sensitive with respect to the choice of k and/or with respect to an associated sequence start.

The plant data may be preprocessed byte-pair encoding. Byte-pair encoding may compress associated data. By design, byte-pair encoding may also find a segmentation of input according to frequent subsequences. Byte-pair encoding may iteratively substitute most frequent pairs of an input with novel symbols (e.g., https://en.wikipeda.org/wiki/Byte pair encoding):

aaabdaaabac
ZabdZabac|Z=aa
ZYdZYac|Y=ab
XdXac|X=ZY

Based on above, the processor 237 may execute a byte-pair encoding module to, for example, cause the processor to generate a segmentation [aaab, d, aaab, ac].

Byte-pair encoding may be applied to DNA data. Similarly, byte-pair encoding may be applied to RNA data. Byte-pair encoding may have the same advantages as non-overlapping k-mer segmentation, however, byte-pair encoding may eliminate dependence on k-mer length and/or lessen dependence on an associated sequence start.

NLP input data may include word embeddings. For example, word embeddings may define vector representations of words. The vector representation of words may be computed by leveraging co-occurrence statistics over large corpora. More particularly, k-mers may be represented as vectors, leveraging co-occurrence of k-mers in long DNA sequences.

Figure 6A:
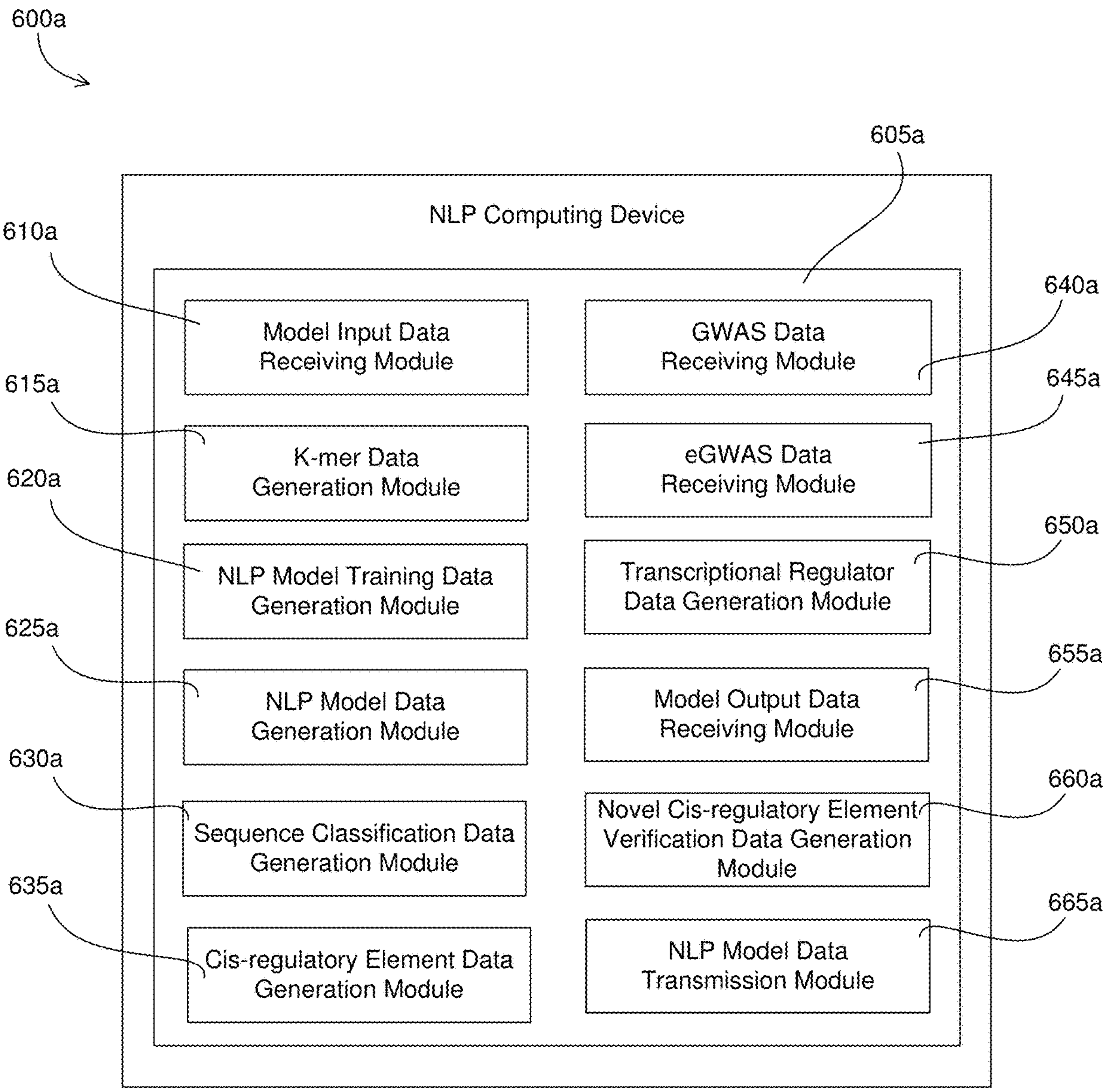
FIGS. 6A-H depict an example natural language processing computing device and example methods of implementation.
Figure 6B:
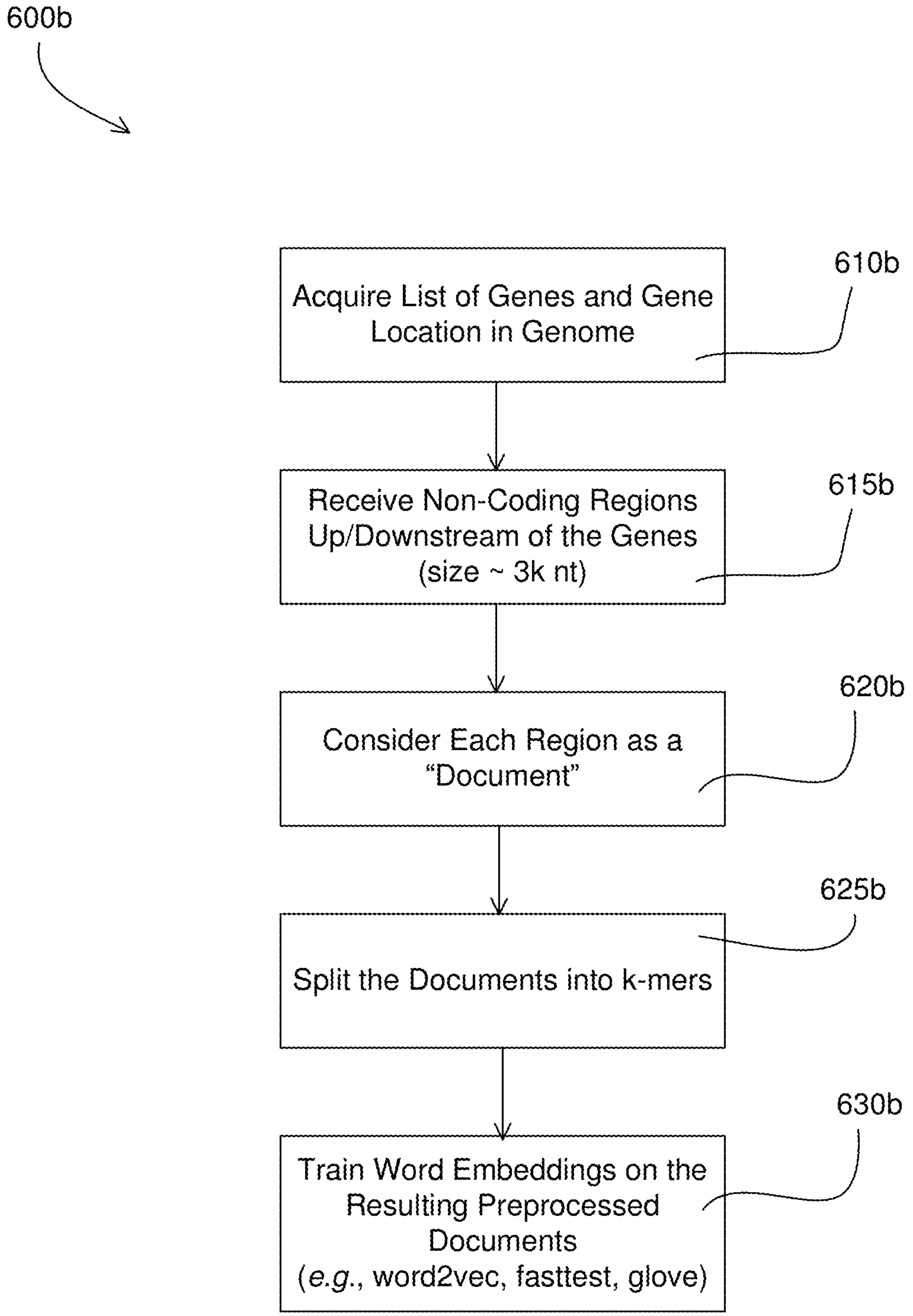

With additional reference to FIG. 6B, a method of generating NLP data 600*b* may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, The processor 231 may execute the NLP model data generation module 625*a* to cause the processor 231 to, for example, acquire a list of genes and respective gene locations in a genome (block 610*b*). The processor 231 may further execute the NLP model data generation module 625*a* to cause the processor 231 to, for example, receive non-coding regions up/downstream of the genes (e.g., size~3k nt) (block 615*b*). The processor 231 may further execute the NLP model data generation module 625*a* to cause the processor 231 to, for example, consider each region as a "document" (block 620*b*). The processor 231 may execute the k-mer data generation module 615*a* to cause the processor 231 to, for example, split the "document" into k-mers (block 625*b*). The processor 231 may further execute the NLP model data generation module 625*a* to cause the processor 231 to, for example, train word embeddings on the resulting preprocessed "documents" (block 630*b*). For example, the processor 231 may implement, for example, word2vec, fasttext, or glove to train word embeddings based on the resulting preprocessed "documents."

With respect to identifying drought-resistant elements (DREs) and/or transcriptional regulators in maize, an associated maize reference genome may be utilized for gathering long sequences is. Because, only non-coding sequences may be input, an input may include only non-coding sequences (or only promoter sequences) from the reference genome when computing word embeddings.

The trained word embeddings can then be used in approaches to predict drought-responsive elements (DREs) and DNA sequence motifs. DNA sequence "motifs" may be representative of short, recurring patterns in DNA that are presumed to have a biological function. Often the motifs indicate sequence-specific binding sites for proteins such as nucleases and transcription factors (TF). A transcription factor (TF) is a protein that controls the rate of transcription of genetic information from DNA to messenger RNA, by binding to a specific DNA sequence.

The processor 231 may classify DNA sequences, and the processor 231 may, for example, extract drought responsive elements (DREs) based on a sequence classification. For example, the processor 231 may implement a Bayesian mixture model, a hidden Markov model, a dynamic Bayesian network, deep multilayer perceptron (MLP), convolutional neural network (CNN), recursive neural network (RNN), recurrent neural network (RNN), long short-term memory (LSTM), sequence-to-sequence model, shallow neural networks, etc. The processor 231 may implement a feature-based machine learning classifier.

Figure 6C:
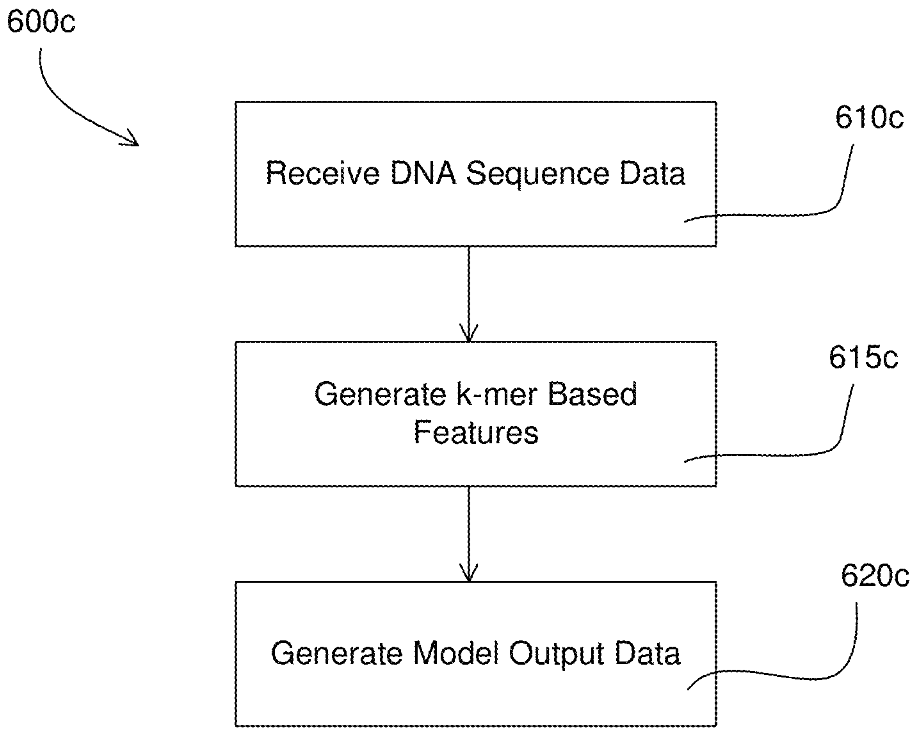

With additional reference to FIG. 6C, a method of classifying DNA sequences using a feature-based machine learning based NLP model 600*c* may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, the processor 231 may execute the model input data receiving module 610*a* to cause the processor 231 to, for example, receive DNA sequence data (block 610*c*). The processor 231 may execute the k-mer data generation module 615*a* to cause the processor 231 to, for example, generate k-mer based features (block 615*c*). The processor 231 may further execute the NLP model data generation module 625*a* to cause the processor 231 to, for example, generate NLP model output data (block 620*c*).

The processor 231 may transform sequences into k-mer based features which are then input to a machine classifier. Each sequence is represented by features, one feature for each possible k-mer. The feature could be the appearance of the k-mer, its frequency, or its tf-idf weighted frequency. These features then serve as input to a machine learning classifier that predicts whether the sequence is drought-responsive or not (for example a logistic regression classifier).

Even though individual k-mers may be, for example, described by arbitrary features, the individual k-mers may still be restricted to looking at each k-mer in isolation. The features may be more complex. For example, features may describe whether pairs of k-mers appear beneath each other. Thereby, a NLP model may be based on local k-mer context, and the feature weights of individual k-mers may be adjusted. For example, DREs may be extracted as described herein.

The processor 231 may implement a word embedding-based feed-forward neural network. Alternatively, the processor 231 may implement logistic regression which may be a linear classifier based on a featurization of the input. In natural language processing, vast improvements in results may be achieve with the use of artificial neural networks that rely on word embeddings of neural network inputs.

A neural network that may be suited for the NLP task is a feed-forward neural network. For example, a feed-forward neural network may receive, as input, a sequence of k-mers, represented by associated word embeddings. The feed-forward neural network may combine the input (e.g., by summing, averaging, or weighted averaging), sends it through one or more hidden layers, and may include an output layer a distribution over possible sequence-level outcomes (e.g., whether the sequence is drought-responsive or not).

Figure 6D:
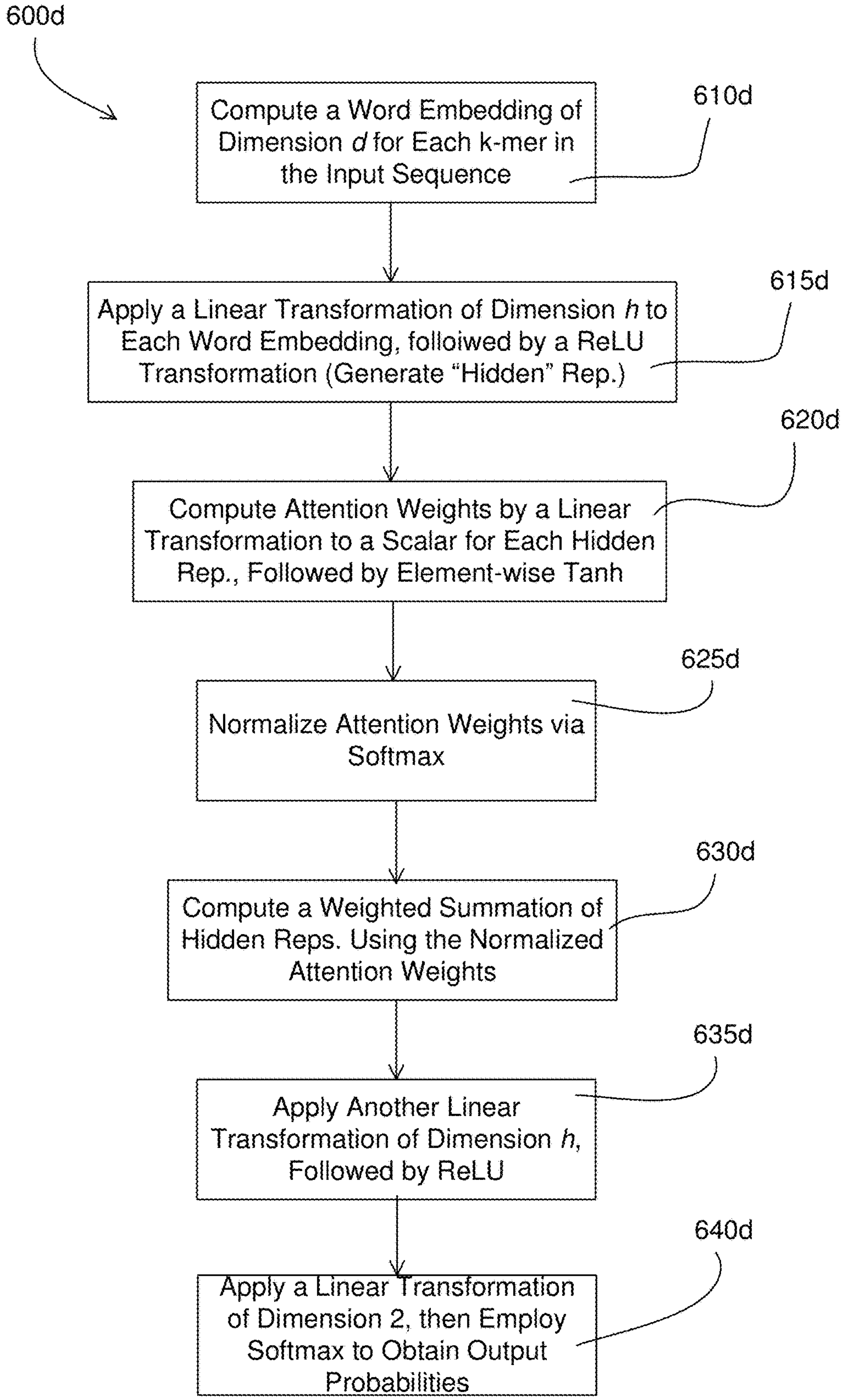

With additional reference to FIG. 6D, a method of classifying DNA sequences using a feed-forward neural network based NLP model 600*d* may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, the processor 231 may execute the NLP model training data generation module 620*a* to cause the processor 231 to, for example, compute a word embedding of dimension d for each k-mer in an input sequence (block 610*d*). The processor 231 may further execute the NLP model training data generation module 620*a* to cause the processor 231 to, for example, apply a linear transformation of dimension h to each word embedding, followed by a ReLU transformation (e.g., generate "hidden" representations) (block 615*d*). The processor 231 may further execute the NLP model data generation module 625*a* to cause the processor 231 to, for example, compute attention weights by a linear transformation to a scalar for each hidden representation, followed by element-wise Tanh (block 620*d*). The processor 231 may further execute the NLP model data generation module 625*a* to cause the processor 231 to, for example, normalize attention weights (block 625*d*). For example, the processor 231 may execute Softmax to cause the processor 231 to, for example, normalize attention weights (block 625*d*). The processor 231 may further execute the NLP model data generation module 625*a* to cause the processor 231 to, for example, compute a weighted summation of hidden representations (block 630*d*). The processor 231 may further execute the NLP model data generation module 625*a* to cause the processor 231 to, for example, compute attention weights by a linear transformation to a scalar for each hidden representation, followed by element-wise Tanh (block 635*d*). The processor 231 may further execute the NLP model data generation module 625*a* to cause the processor 231 to, for example, to apply a linear transformation of dimension 2, then obtain NLP model outputs (block 640*d*). For example, the processor 231 may execute Softmax to cause the processor 231 to, for example, to obtain NLP model output probabilities (block 640*d*).

A neural network may, for example, include inputs that influence an output (e.g., identification of a novel cis-element, identification of an upstream transcriptional regulators of novel cis-element, etc.). Processor 231 may execute a recurrent neural network based NLP model to classify DNA sequences.

Sequence-based models, such as recurrent neural networks (RNNs), process the input in sequential order. Typically, such approaches would embed each k-mer in the input, and then process these k-mers sequentially, building "hidden" representations that contain information about each k-mer in its context. Based on the hidden representation of the last k-mer in the sequence—that, by construction, contains the condensed representation of the whole sequence—a prediction is made whether the sequence is drought-responsive or not. Moreover, typically such models process the input once from left-to-right and once from right-to-left. The hidden representations from both directions are then combined.

Figure 6E:
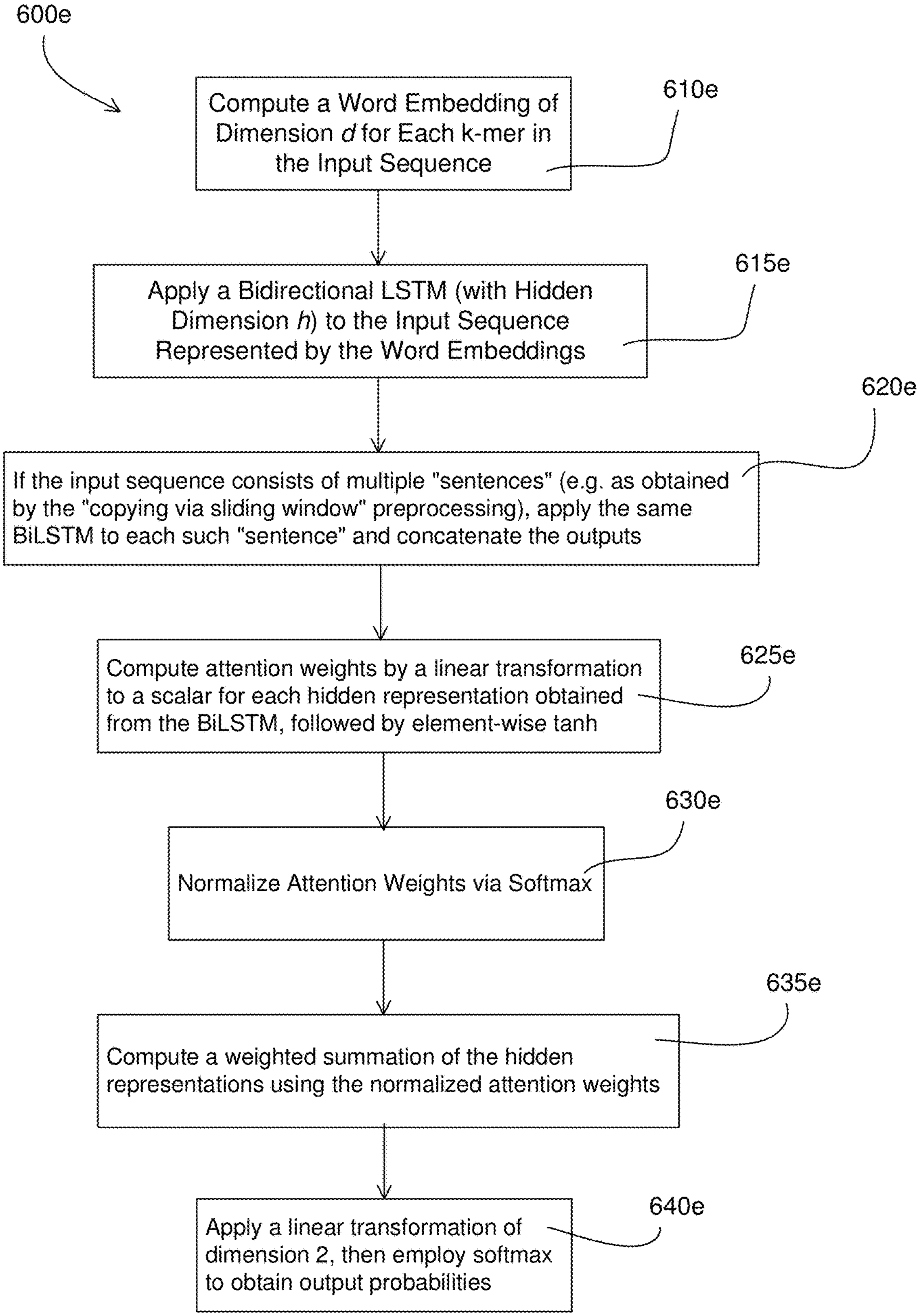

With additional reference to FIG. 6E, a method of classifying DNA sequences using a recurrent neural network based NLP model 600*e* may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, the processor 231 may execute the NLP model training data generation module 620*a* to cause the processor 231 to, for example, compute an embedding of dimension d for each k-mer that is in the input sequence (block 610*e*). The processor 231 may further execute the NLP model training data generation module 620*a* to cause the processor 231 to, for example, apply a bidirectional LSTM (with hidden dimension h) to the input sequence represented by word embeddings (block 615*e*). The processor 231 may further execute the NLP model data generation module 625*a* to cause the processor 231 to, for example, if the input sequence consists of multiple "sentences" (e.g., as obtained by the "copying via sliding window" preprocessing), apply the same BiLSTM to each such "sentence" and concatenate the outputs (block 620*e*). The processor 231 may further execute the NLP model data generation module 625*a* to cause the processor 231 to, for example, compute attention weights by a linear transformation to a scalar for each hidden representation obtained from the BiLSTM, followed by element-wise tanh (block 625*e*). The processor 231 may further execute the NLP model data generation module 625*a* to cause the processor 231 to, for example, normalize attention weights (block 630*e*). For example, the processor 231 may execute softmax to cause the processor 231 to, for example, normalize attention weights (block 625*e*). The processor 231 may further execute the NLP model data generation module 625*a* to cause the processor 231 to, for example, compute a weighted summation of the hidden representations using the normalized attention weights (block 635*e*). The processor 231 may further execute the NLP model data generation module 625*a* to cause the processor 231 to, for example, to apply a linear transformation of dimension 2, then employ softmax to obtain output probabilities (block 640*e*). For example, the processor 231 may execute softmax to cause the processor 231 to, for example, to obtain NLP model output probabilities (block 640*e*).

The processor 231 may perform Cis-regulatory element (e.g., DRE) extraction. A set of preprocessed DNA sequences and classification output data, including internal parameters of associated classification models, may be used for drought-resistant elements (DRE) extraction. Selection of a given model, or models, may depend on the preprocessing. For example, if a sequence is preprocessed into k-mers, the k-mers may be used directly as candidates for DREs. For example, the processor 231 may extract Cis-regulator elements based on a classical statistical approach. The processor 231 may implement a classical statistical approach to motif discovery, such as implemented in MEME or MotifSuite. A classical statistical approach may not include classification.

Figure 6F:
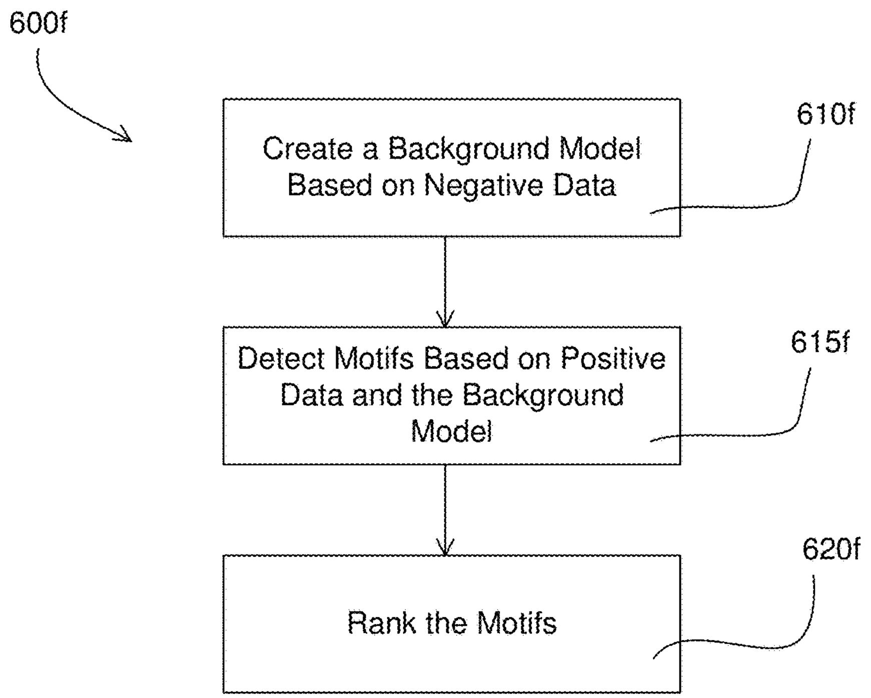

With additional reference to FIG. 6F, a method of extracting Cis-regulatory elements 600*f* may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, the processor 231 may execute the NLP model data generation module 625*a* to cause the processor 231 to, for example, create a background model on the negative data (block 610*f*). The processor 231 may further execute the NLP model data generation module 625*a* to cause the processor 231 to, for example, generate k-mer based features (block 615*f*). The processor 231 may execute the Cis-regulatory element data generation module 635*a* to cause the processor 231 to, for example, rank motifs (block 620*f*).

The processor 231 may generate feature weights of a classifier. For example, from a feature-based machine learning classifier, a ranked list of k-mers may be generated by, for example, sorting the list of k-mers with respect to a respective k-mer feature weight (this is the "bag-of-k-mer" approach used by Mejia-Guerra and Buckler). A feature-based machine learning classifier is relatively straight-forward, since associated feature weights may directly represent importance of k-mers for a prediction.

Figure 6G:
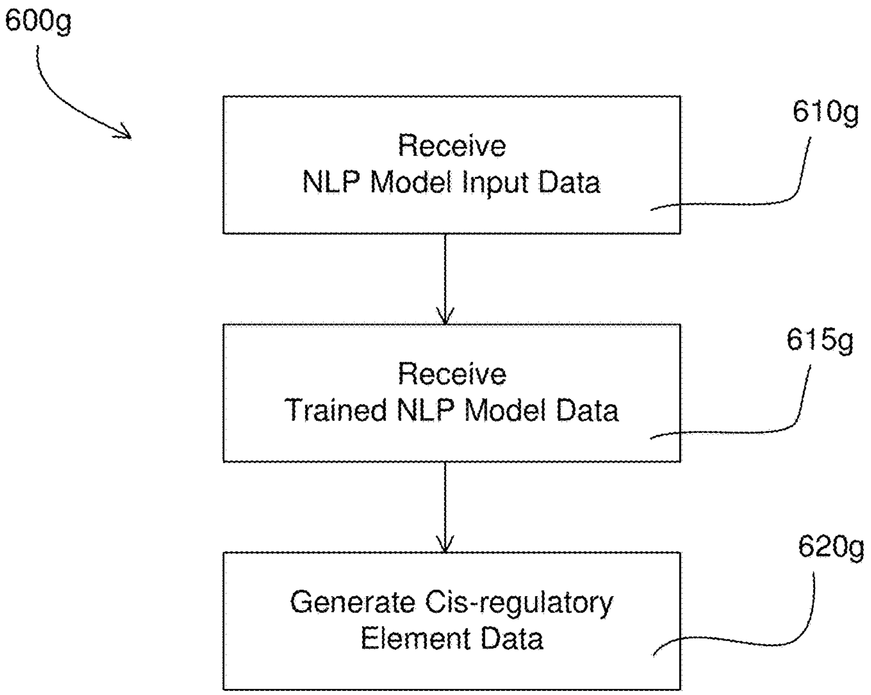

With additional reference to FIG. 6G, a method of extracting Cis-regulatory elements 600*g* may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, the processor 231 may execute the model input data receiving module 610*a* to cause the processor 231 to, for example, receive NLP model input data (block 610*g*).

The processor 231 may further execute the model input data receiving module 610*a* to cause the processor 231 to, for example, receive trained NLP model data (block 615*g*). The processor 231 may execute the Cis-regulatory element data generation module 635*a* to cause the processor 231 to, for example, generate Cis-regulatory element data (block 620*g*).

The processor 231 may incorporate saliency into natural language processing (NLP) (e.g., a magnitude of a derivative of an output with respect to an input). To compute saliency for an associated NLP model, the processor 231 may compute a derivate of an output score for a positive label with respect to input word embeddings. The processor 231 may either 1) compute an absolute value for each dimension and then sum; or 2) compute a dot product of embedding and gradient, then compute an absolute value. Thereby, the processor may determine an influence of model input k-mers on positive classification.

The processor 231 may generate attention weights of NLP models, and may be used to find NLP model input k-mers that may be most significant for DRE extraction. For example, a neural attention mechanism may equip a neural network with an ability to focus on a subset of inputs (or features) to the associated neural network (i.e., neural attention may select specific inputs). An attention mechanism may combine hidden representations from each k-mer, and may supply the combined hidden representations as additional information during DRE extraction. As the combination may be implemented as a weighted sum, the weights can be used to rank k-mers with respect to a respective k-mer's influence (e.g., k-mers may be ranked by influence on drought-responsiveness). Attention weights may measure an influence on a current DRE extraction. Hence, k-mers associated with being, for example, drought-responsive or not may be identified. An NLP model analysis, using attention weights, may be employed when, for example, only genes where a prediction is representative of the gene is drought-responsive are considered.

Figure 6H:
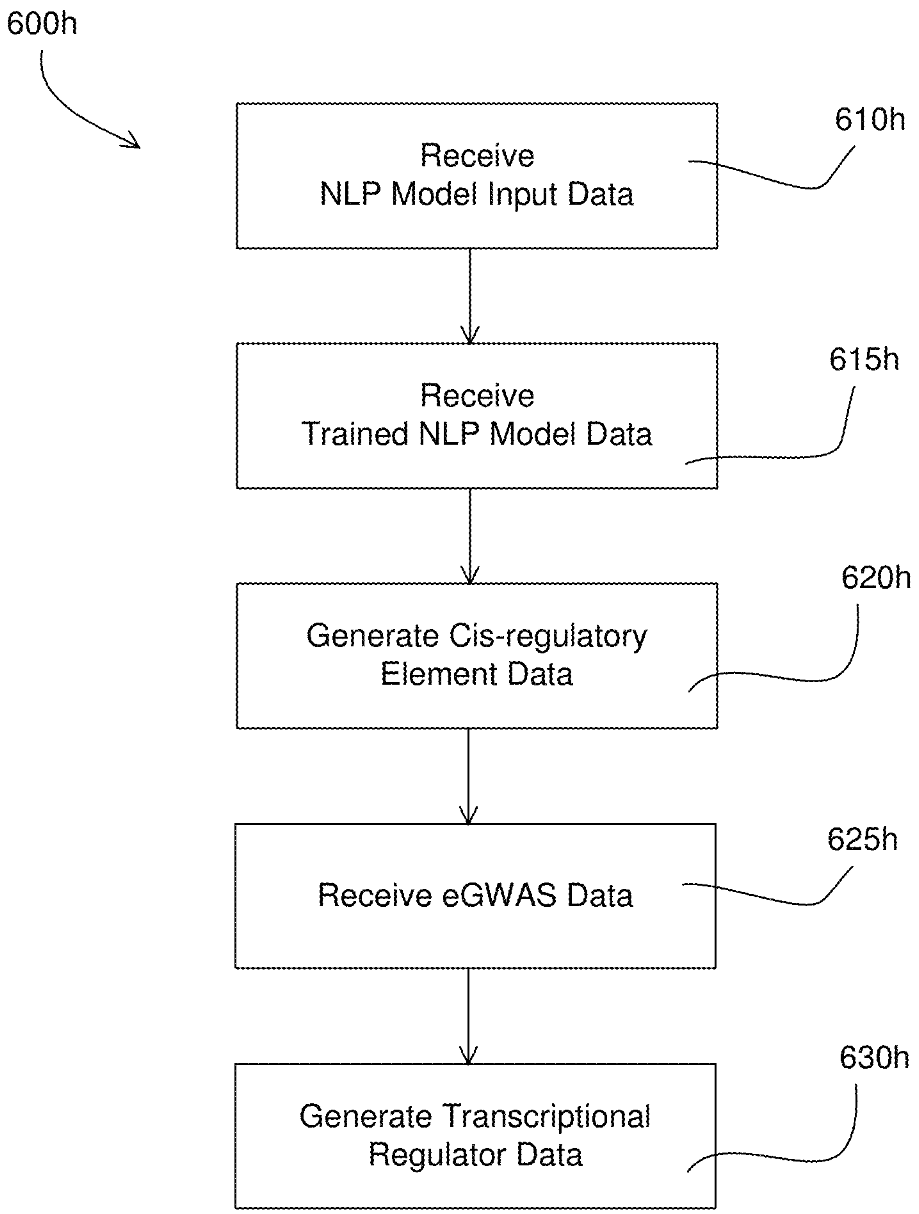

With additional reference to FIG. 6H, a method of identifying transcriptional regulators 600*h* may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, the processor 231 may execute the model input data receiving module 610*a* to cause the processor 231 to, for example, receive NLP model input data (block 610*h*). The processor 231 may further execute the model input data receiving module 610*a* to cause the processor 231 to, for example, receive trained NLP model data (block 615*h*). The processor 231 may execute the Cis-regulatory element data generation module 635*a* to cause the processor 231 to, for example, generate Cis-regulatory element data (block 620*h*). The processor 231 may further execute the eGWAS data receiving module 646*a* to cause the processor 231 to, for example, receive eGWAS data (block 615*h*). The processor 231 may execute the transcriptional regulator data generation module 650*a* to cause the processor 231 to, for example, generate transcriptional regulator data (block 620*h*).

As described herein, a given DNA sequence, or portion thereof, may be classified, for example, as to whether a corresponding gene is differentially expressed when exposed to drought. Subsequently, DREs (which may be referred to as "motifs") may be extracted from an associated NLP dataset. A motif may be small (e.g., 6 to 12 bp) subsequences of the DNA sequences that are correlated with the corresponding gene being differentially expressed when exposed to drought. Additionally, a list of genes that contain identified DREs may be generated.

A fundamental question for applying NLP methods to genomic data is how a whole sequence can be segmented into "sentences" and "words" that then can be digested by NLP algorithms. Given previous work there seems to be no consensus on this question. An approach in bioinformatics is to segment a sequence into highly overlapping k-mers. Alternatively, data augmentation may be performed by first obtaining shifted copies of an input sequence, and then splitting the shifted copies of the input sequence into non-overlapping k-mers.

Different combinations of preprocessing methods, classifiers, and feature extraction methods may be conducted on a dataset containing, for example, ~115,000 DNA sequences that represented the promoter sequence (including the 5'UTR) for ~12,000 genes across two-hundred forty-seven maize genotypes. The data may be split into training, development, and testing sets. Classification of promoter sequences as being drought-responsive or not may be evaluated by accuracy, recall/precision/F1 (with respect to the positive class), auROC, and average precision (AP). A plant dataset 116 may contained, for example, ~115,000 sequences that may represent promoter sequences (e.g., 3 kb upstream of the coding sequence) for ~12,000 genes. The plant dataset may be split into a training dataset, a development dataset, and a testing dataset.

Classification of promoter sequences may be classified into, for example, being drought-responsive or not by accuracy, recall/precision/F1 (with respect to the positive class), auROC, and average precision (AP). A baseline (e.g., a majority baseline) may be employed which may assign a class that is most frequent in the training data (i.e., the positive class).

A logistic regression classifier based on, for example, 6-mer splitting and L1 regularization with C=0.01 may be chosen as a learning-based baseline model (i.e., 6-mers have shown to yield good performance for related tasks in previous related work). When a dataset contains many more sequences than genes, many sequences in the dataset may have high overlap, which may lead to overfitting. An amount of similar sequence in the training subset may be reduced. For example, a relation "A is similar to B if A and B are of different genotypes for the same gene and if Hamming similarity is above 0.9". Equivalence classes may be calculated according to the relation, and one arbitrary sequence may be selected from each equivalence class. All sequences chosen this way comprised the training data. A variant may be considered in which preprocessing may be changed to "copying via sliding window" based on 6-mers. Alternatively, byte-pair encoding (BPE) may be used for preprocessing (e.g., a vocabulary size of 8,000 may be enforced). Approaches (e.g., DeepMotif and gkSVM) for related tasks may be adapted, and tried to run a classical motif finding approach based on MotifSuite. The approaches may produce either results close to random or results that may not be scalable to an associated size of datasets.

As illustrated in Table 1 below, baseline results and results for some simple neural network models are compared. Notably, any given model may be trained based upon training data, and may be evaluated based upon development data.

TABLE 1

| MODEL | ACCURACY | RECALL | PRECISON | F1 | AP | AUROC |
|---|---|---|---|---|---|---|
| Majority Class | 56.75 | 100.00 | 56.75 | 72.40 | 56.75 | 50.00 |
| Logistic Regression | 58.80 | 58.00 | 65.46 | 61.50 | 66.21 | 62.05 |
| Feed-forward NN | 60.40 | 51.19 | 70.94 | 59.47 | 69.32 | 65.48 |
| Recurrent NN | 65.47 | 59.01 | 74.81 | 65.99 | 76.45 | 72.12 |
| Recurrent NN with byte-pair encoding | 60.64 | 51.24 | 71.33 | 59.64 | 72.49 | 66.18 |

Evaluation of model performance may be based upon a developmental training set. For example, a pre-processing method may be used that includes a sliding window of 6-mers. While a sliding window of 6-mers may be used for pre-processing, a different sliding window may be used for pre-processing depending on, for example, plant data to be input. For example, neural networks may be initialized with word embeddings data trained on regulatory data.

To generate predictions and identify novel putative drought-response cis-elements, the entire dataset may be split into five folds (fold0-4), and predictions may be performed on each fold using multiple models. The data output from the models may be assembled into JSON files that listed the top 100 ranked k-mers predicted to be drought-responsive. Additional information including nucleotide position upstream of a CoDing Sequence (CDS), similarity to known DREs, and co-occurring k-mers may also reported with each k-mer. A CoDing Sequence (CDS) is a region of DNA or RNA whose sequence determines the sequence of amino acids in a protein.

The processor 231 may evaluate NLP model outputs to, for example, assess a biological relevance of k-mers classified as drought-responsive using NLP methods, a list of known DREs from maize may be compiled from the literature (See Table 5), and may be used as a "positive control" by testing for the presence of known DREs in NLP output data.

The processor 231 may analyze a model output to determine if an associated model output may be significantly enriched for known DREs. For example, the processor 231 may compare model output to five sets of randomly sampled k-mers, and to a set of known DREs. The processor 231 may calculate a similarity of known DREs to a population of 100 randomly sampled k-mers from a positive training dataset (repeated five times) or the top 100 k-mers classified as drought-responsive from a feed forward neural network (6-mer sliding window using attention for feature extraction).

Figure 7:
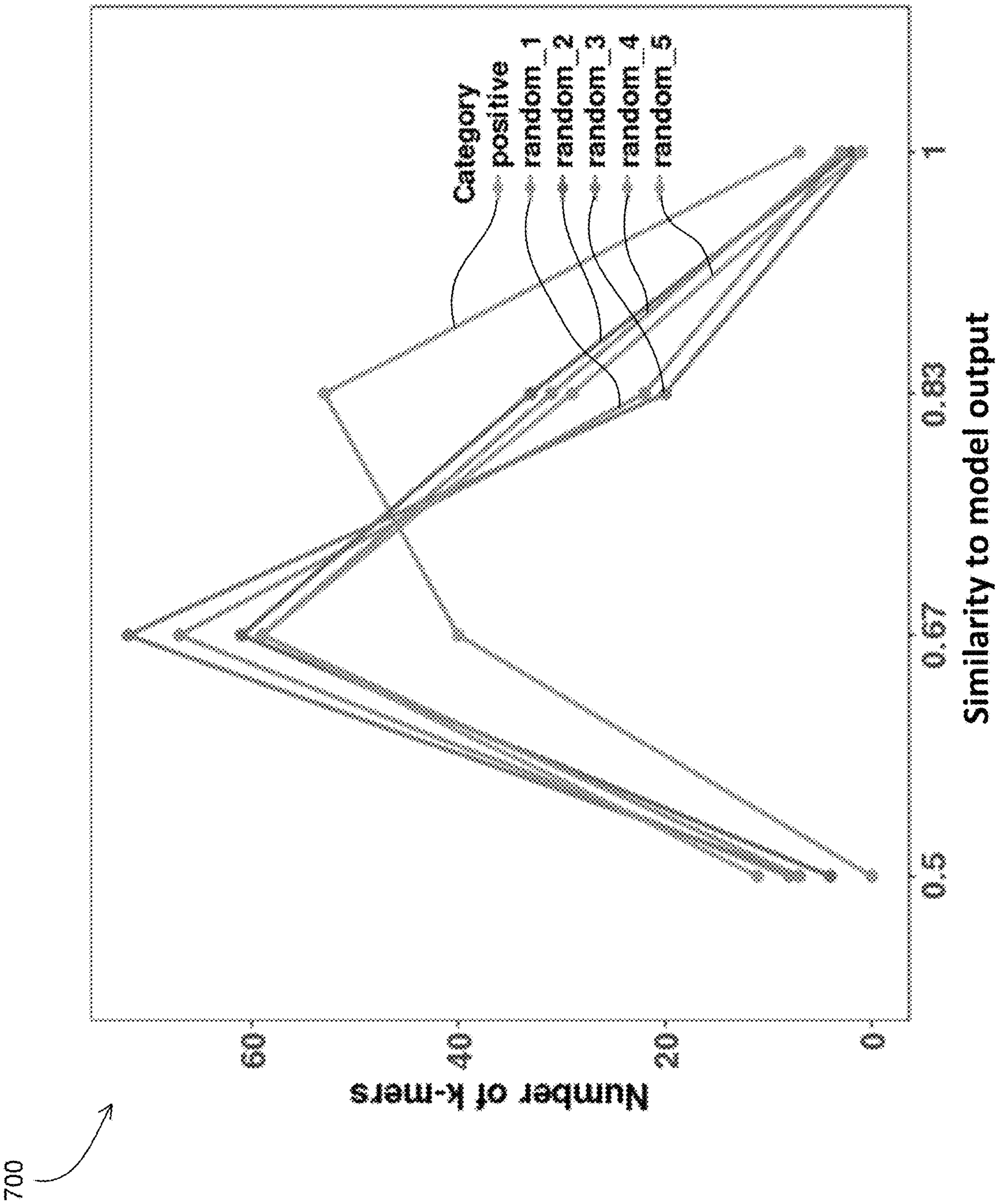
FIG. 7 depicts an example graph of a similarity of model output to random k-mers versus similarity of model output to known DREs for various biological data.

With reference to FIG. 7, k-mers identified using NLP methods classified significantly more k-mers (p-value=2.2e-07) that had higher similarity to known DREs than to the randomly sampled set of k-mers. Among other things, the graph 700 indicates that NLP methods may identify known DREs, and demonstrates that data sets that are generated using NLP methods are biologically relevant. As further illustrated in the graph 700, k-mers identified using NLP methods ("positive") may be significantly enriched for known DREs compared to being enriched for a randomly sampled population ("random"). The apparatuses, systems, and methods described herein may, for example, report the top 100 k-mers. While the top 100 k-mers may be reported, more or less k-mers may be reported to capture all relevant k-mers.

Figure 8A:
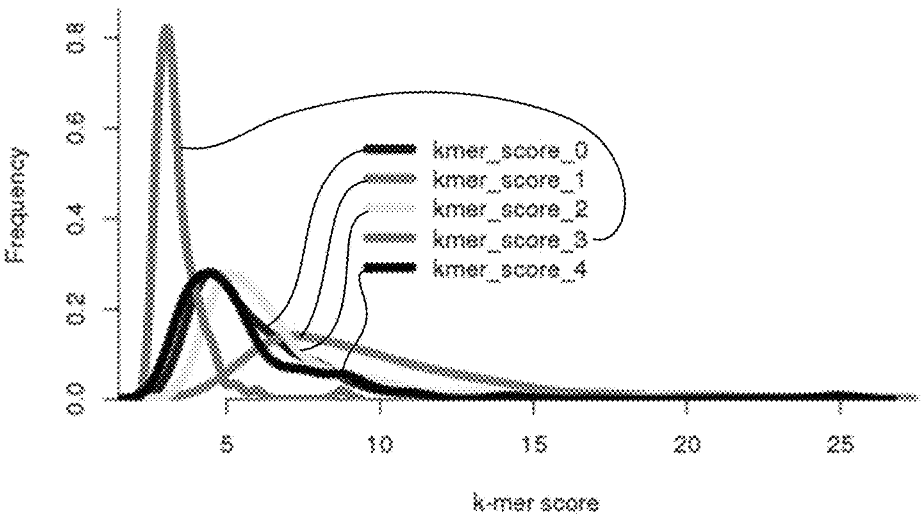
FIGS. 8A-C depict an example graph of k-mers scores versus frequency of occurrence for a plurality of models and respective input data preprocessing.
Figure 8B:
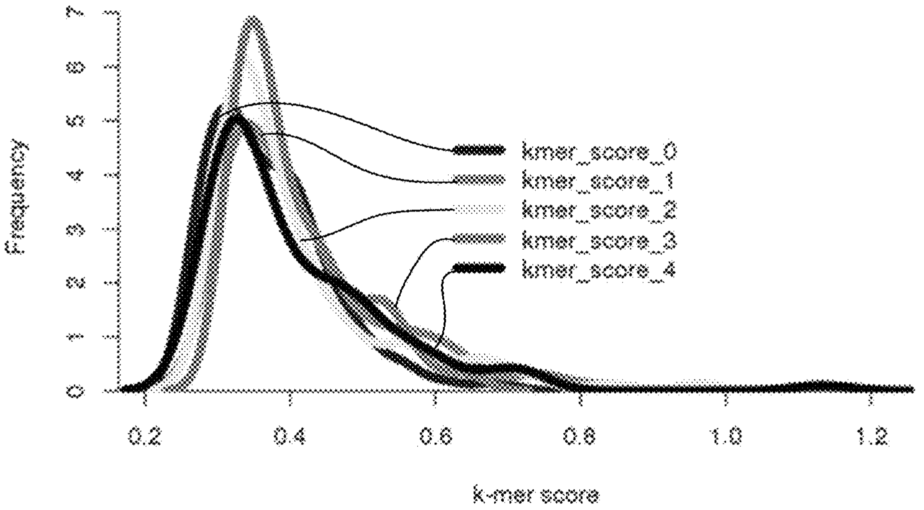
Figure 8C:
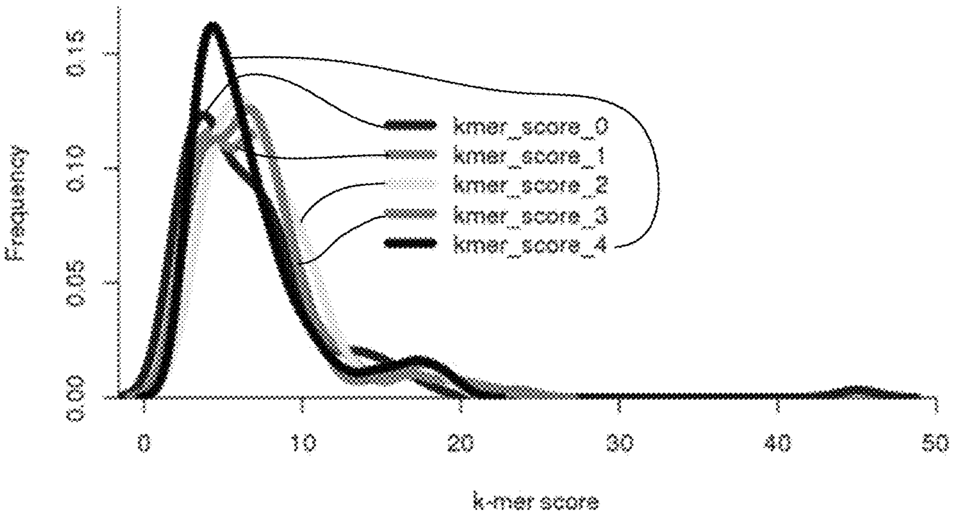

Turning to FIGS. 8A-C, graphs 800*a-c* may include k-mer scores for each of five folds that are plotted for three different models. Feature weights may be used to assign scores to each k-mer predicted by the model to be drought-responsive (i.e., k-mers with higher scores may indicate higher confidence that a given k-mer is drought-responsive). If the most relevant k-mers are reported, an increase of k-mers with low scores may occur. Alternatively, if all relevant k-mers are not captured, a consistent frequency across all k-mer scores may occur (i.e., indicating that relevant k-mers may be missing in the output, and more k-mers may be reported to reach a saturation point of k-mers that had low (baseline) scores). A very high frequency of k-mers with low scores may be observed in each of the folds for the three models assessed, compared to a low frequency of k-mers with high scores (i.e., this may indicate that using the 100 ranked k-mers from the model output is sufficient for capturing all relevant k-mers-k-mers with scores that indicated high confidence of drought-responsiveness).

Reporting the top 100 k-mers may be sufficient. A) Recurrent neural network (LSTM) using a sliding window B) Recurrent neural network (LSTM) using byte-pair encoding, C) feed-forward neural network using a sliding window, with feature weights reported using attention. Kmer_score_0 refers to scores of k-mers identified in fold 0, etc.

Figure 9:
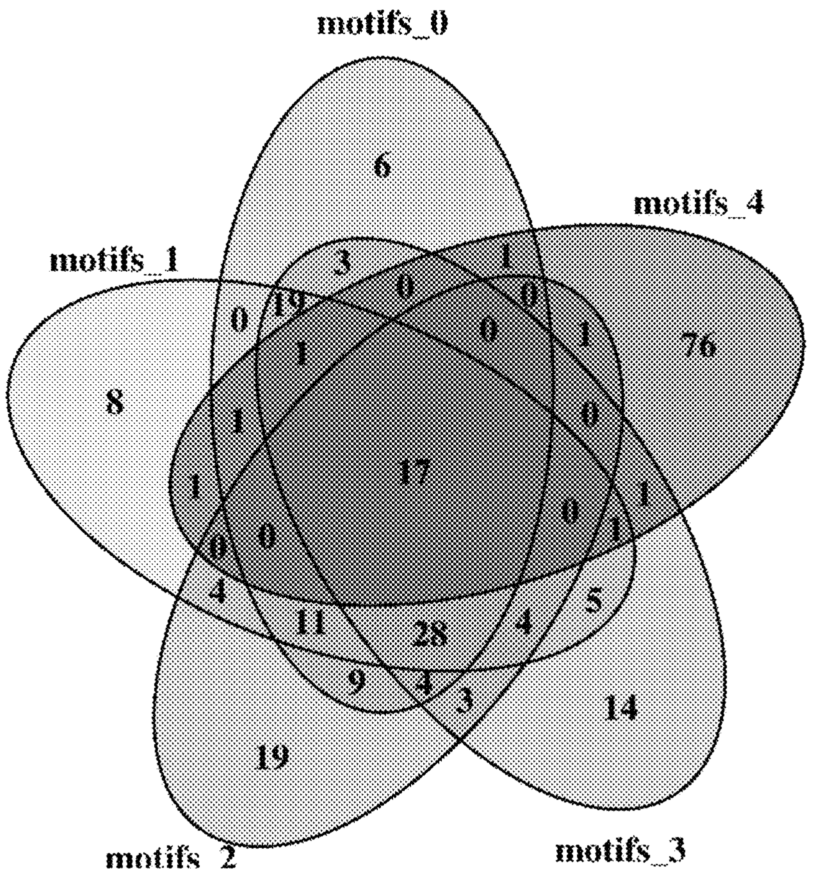
FIG. 9 illustrates example variation of k-mers identified in various motifs using the feed forward neural network.

With reference to FIG. 9, the similarity of the top 100 ranked k-mers predicted within each fold for each model may be compared. Little overlap of the top 100 k-mers identified within each fold by each model may occur (i.e., this could be due to the high frequency of low scoring k-mers, indicating that k-mers that have low scores are essentially reported at random). In other words, the difference between all low scoring k-mers may be extremely minimal. Therefore, assigning an arbitrary cutoff of reporting the top 100 k-mers may include k-mers that have very low confidence of actually being drought-responsive compared to the entire population of other low scoring k-mers. These observations may suggest that meaningful k-mers will likely only be present in a top 75th percentile of the entire 100 k-mer output. Variation of k-mers identified in each fold using the feed forward neural network (sliding window, feature weights reported using attention) are illustrated in FIG. 9. K-mers identified from fold 0 are labeled as "motifs_0" and so forth. Output is representative of the output from all models tested.

Figure 10:
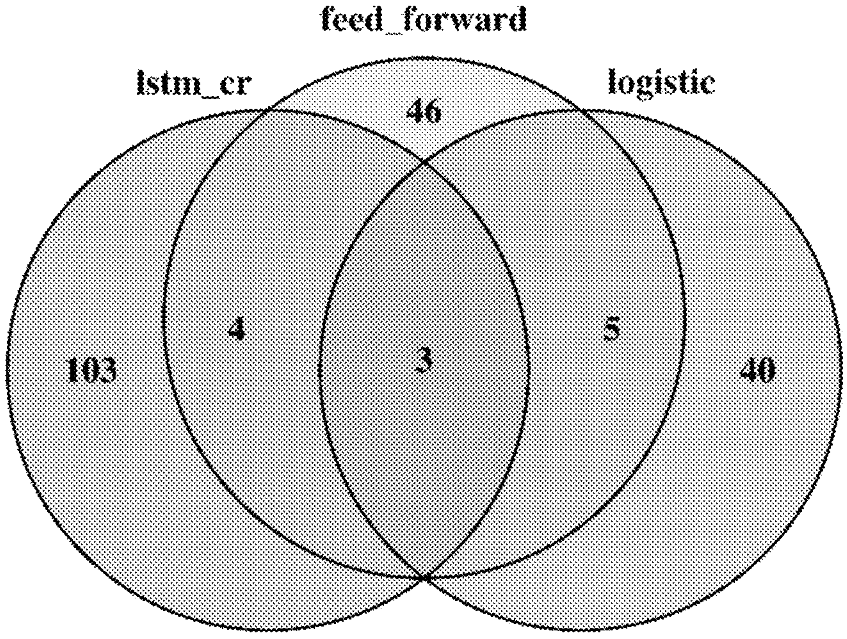
FIG. 10 illustrates an example comparison of top scoring k-mers identified by three different models.

Turning to FIG. 10, k-mers identified by multiple models may be compared. For example, the k-mers with scores in the top 75th percentile for three models (a recurrent neural network model (LSTM), a feed-forward neural network model, and a logistic regression model) that used a sliding window as the preprocessing method may be compared. Although a majority of top scoring k-mers may be identified by an individual model, two of three k-mers identified by all three models may be, for example, identical to known DREs (i.e., TGCATG and CATGCA). This may suggest that high confidence k-mers may be identified by combining the output from multiple models instead of relying on the output from only one model.

The graph 1000 illustrates a comparison of top scoring k-mers identified by the three models. Scores representing the top $75^{th}$ of k-mers identified by each of the three models may be compared. The number of k-mers that represent the top $75^{th}$ percentile may vary between different models due to redundancy of k-mers identified in multiple folds. Two of the three k-mers identified using all three models may correspond to two known DREs. This may indicate that high-confidence novel DREs may be discovered from combining output from multiple models. Recurrent neural network=lstm_cr, feed forward neural network=feed_forward, logistic regression=logistic. The three models compared may use, for example, a 6-mer sliding window.

Figure 11:
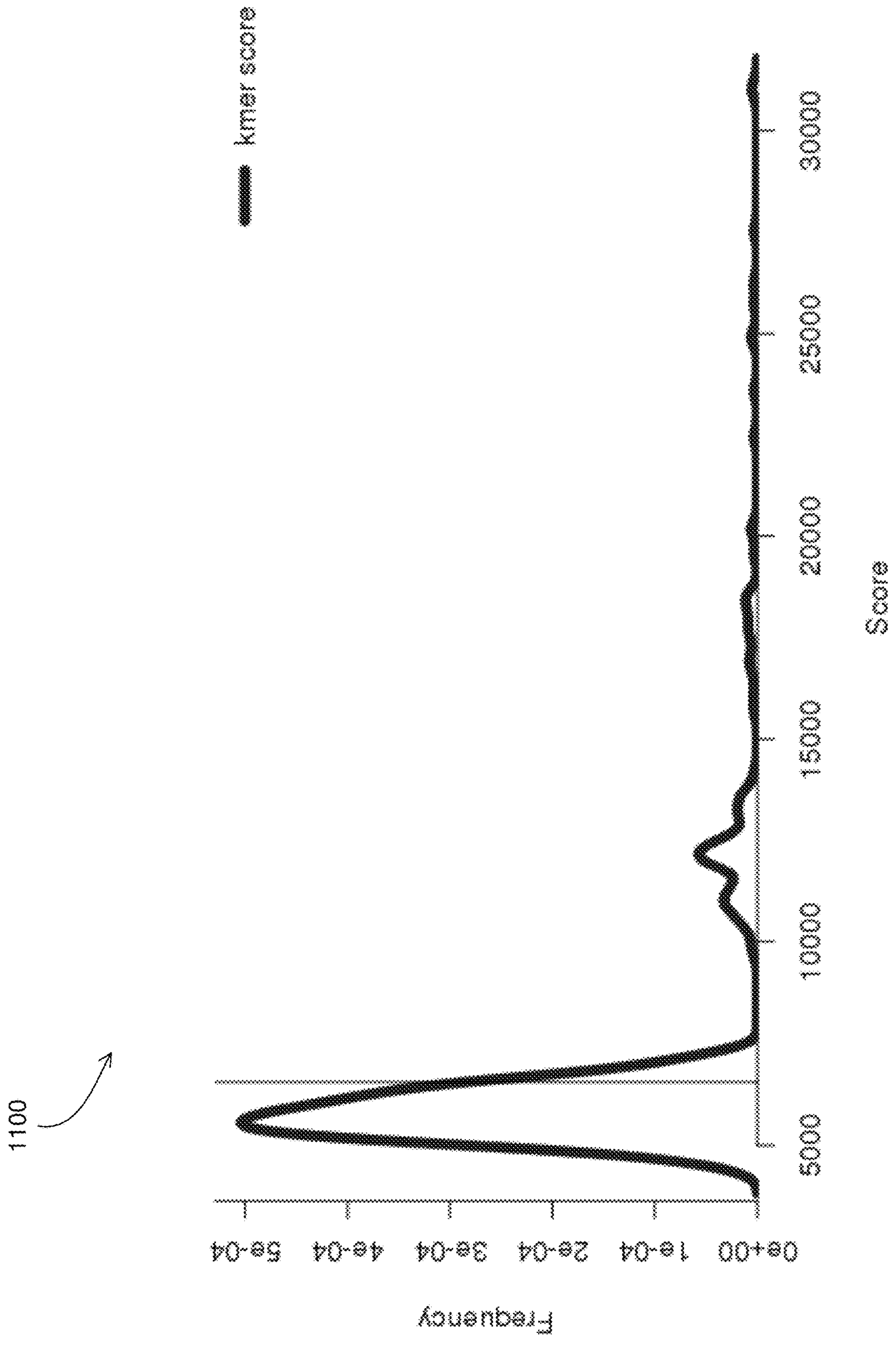
FIG. 11 depicts an example graph of putative novel drought-responsive k-mer scores based on feature weight, appearance in multiple models, and model performance (auROC) versus frequency of occurrence.

Turning to FIG. 11, putative novel drought-responsive k-mers ranked by score using a prioritization pipeline are illustrated. Novel k-mers may be identified by combining output from a plurality of different models. Each k-mer may be assigned a respective prioritization score based on feature weight, appearance in multiple models, and/or model performance (auROC). K-mers that are identical to known DREs may be removed, leaving only novel drought-responsive k-mers.

Figure 12:
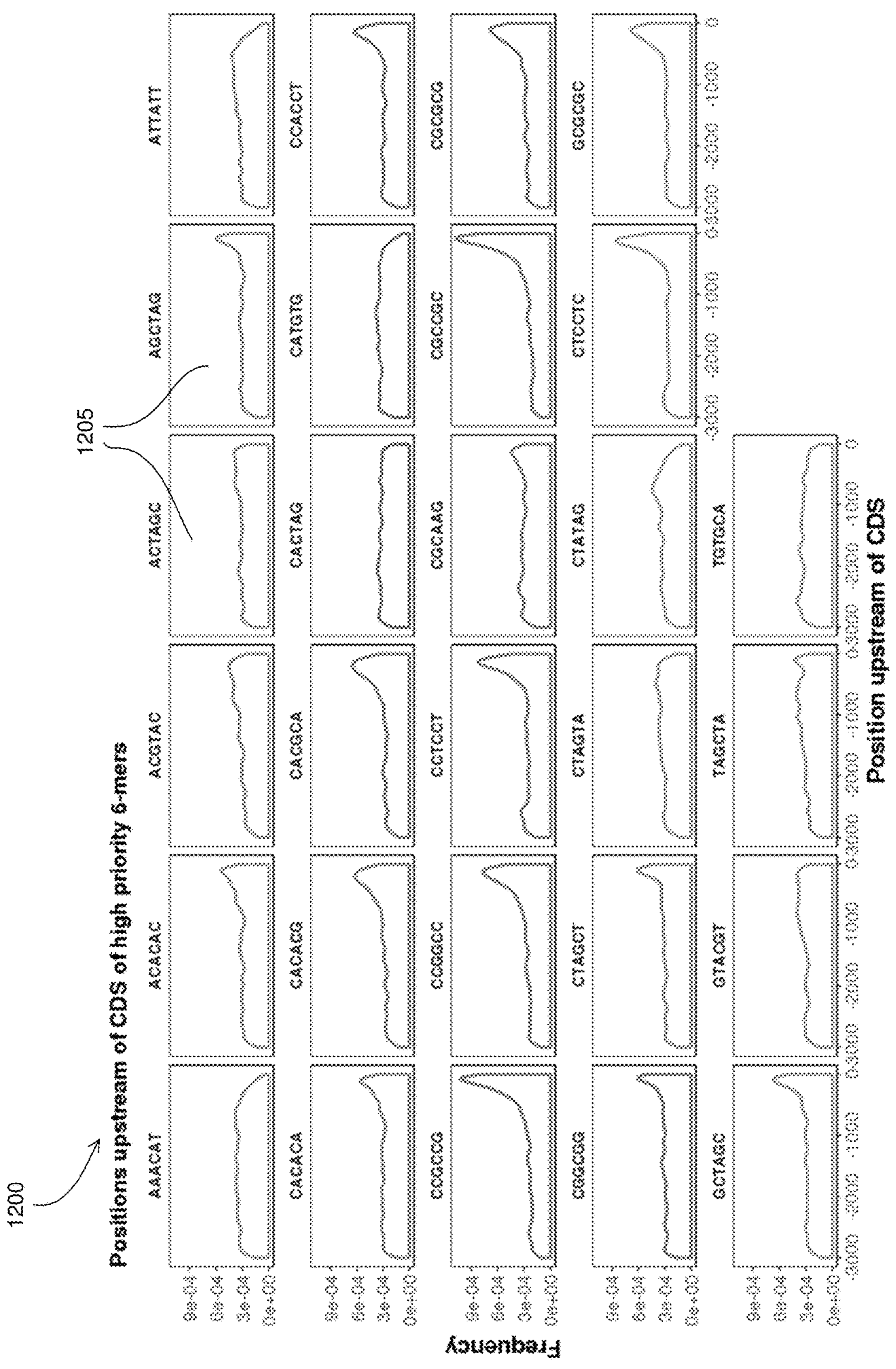
FIG. 12 depicts a plurality of example graphs illustrating distribution of novel k-mers with high prioritization scores within promoter regions.

With reference to FIG. 12, a graph 1200 may identify high confidence novel drought-responsive k-mers. A prioritization pipeline may be developed to prioritize novel k-mers for downstream analysis by combing the output of all models. This pipeline may account for a feature weight of each k-mer assigned by a model, the appearance of a k-mer in multiple models, and the performance of the model using auROC scores. After assigning scores to each k-mer based on those criteria, k-mers identical to known DREs may be removed, resulting in a ranked list of novel drought-responsive k-mers. A k-mer prioritization script may be used to identify high confidence novel drought-responsive k-mers.

For example, a processor 231 may execute a k-mer prioritization module to, for example, cause the processor 231 to store information associated with each k-mer instance. The information associated with each k-mer instance may include: a gene/genotype in which the respective k-mer appears; a drought-positive classification confidence on a gene/genotype-level for each model; k-mer weights according to each model (e.g., a feature weight for logistic regression, attention for feed-forward neural net, saliency for feed-forward neural net, etc.); a position; and/or normalized ranks of k-mer weights when compared to all weights given by a respective model (i.e., highest k-mer weight across all k-mers from all genes/genotypes according to a model has rank 1, and the lowest weight has rank 0). Subsequent to storing the information associated with each k-mer instance, the processor 231 may, for example, employ two methods to prioritize k-mers. The first method to prioritize k-mers may include: 1) For each model, select all k-mers that have an average rank of greater than 0.7; and 2) For the selected k-mers, select all k-mers that were selected from at least 80% of the considered models. The second method to prioritize k-mers may include: 1) Select all gene/genotype/model combinations where the confidence of the model's prediction for being drought-positive was at least 0.7; 2) Retain all gene/genotype combinations that were selected for all models; and 3) For each model, select all k-mers from the retained gene/genotype combinations that have an average rank of greater than 0.7 (computed over all genes/genotypes). Subsequent to the processor 231 prioritizing k-mers using the two methods different methods for prioritizing k-mers, the processor 231 may combine the output of the two different methods.

A graph, similar to graph 1200 may illustrate putative novel drought-responsive k-mers ranked by score using a prioritization pipeline. Novel k-mers may be identified by combining the output from all models developed in this study. Each k-mer may be assigned a prioritization scores based on feature weight, appearance in multiple models, and model performance (auROC). K-mers identical to known DREs may be removed, leaving only novel drought-responsive k-mers.

Figure 13:
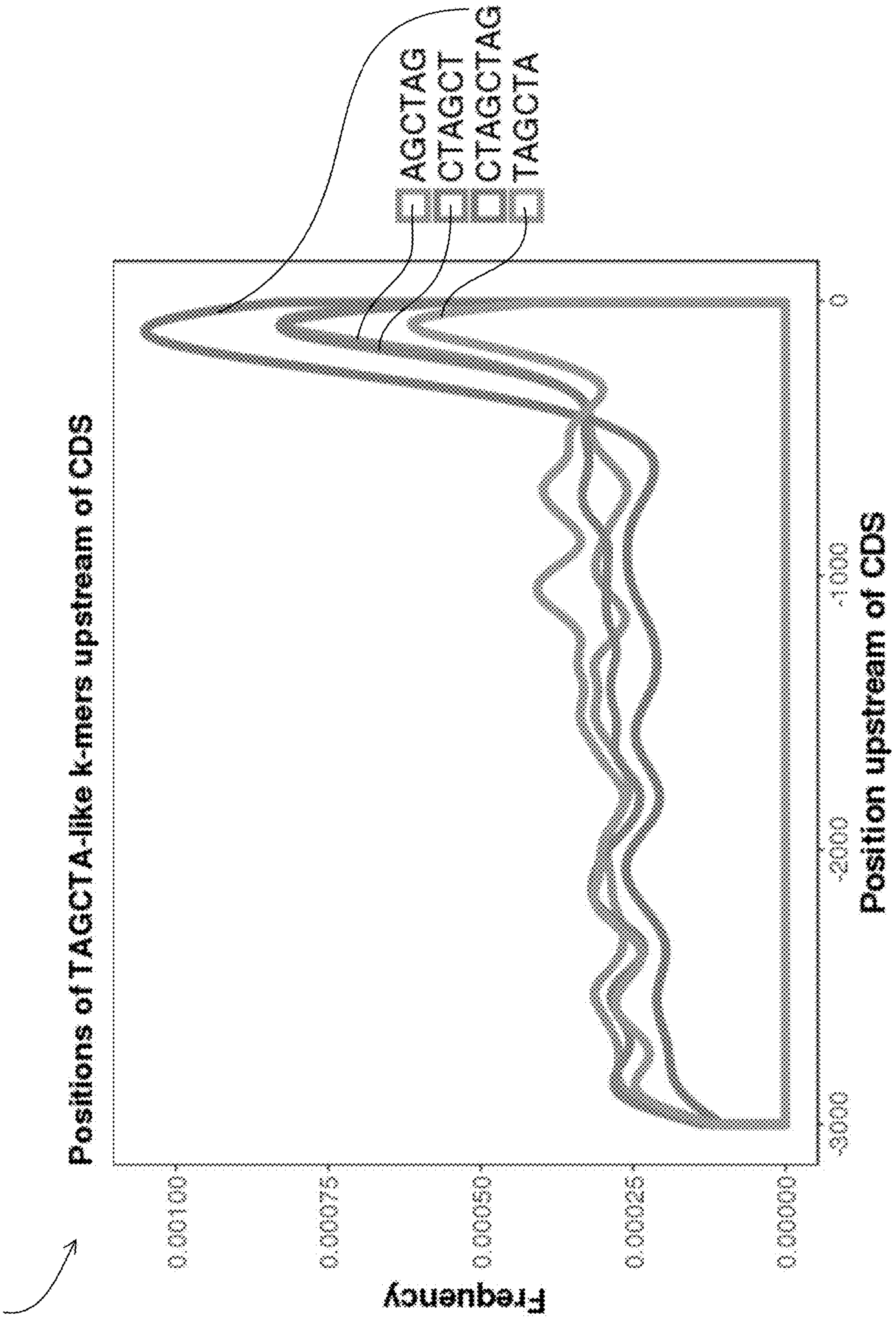
FIG. 13 depicts an example graph of frequency of occurrence verses positions of TAGCTA-like k-mers upstream of CDS.

Turning to FIG. 13, a plurality of graphs may be used to assess distribution patterns of high priority k-mers within promoter regions. For example, the positions of the top 28 high priority 6-mers across all occurrences in 3 kb upstream of CDS may be analyzed. The novel 6-mers with high prioritization scores may be enriched in regions near a start of a CDS, while others may display a more even distribution across an entire promoter region. Functional cis-elements may correspond to k-mers that show some pattern of enrichment across the promoter sequence, such as near a start codon. This may demonstrate that NPL models identified k-mers that show different patterns of position enrichment, indicating that these putative cis-elements may serve to regulate gene expression of different sets of genes. Graph 600 may illustrate a distribution of novel k-mers with high prioritization scores within promoter regions. For example, a location upstream of the CDS may be plotted for the 28 6-mers with the highest prioritization scores (i.e., clear differences in the distributions of each k-mer within the promoter region can be seen).

The top six priority novel k-mers identified using the prioritization pipeline are displayed in Table 2 (i.e., top six novel k-mers identified using the prioritization pipeline). For example, the TAGCTA k-mer may be chosen.

TABLE 2

| TOP PRIORITY NOVEL K-MERS | SCORE |
|---|---|
| CCTCCT | 31153.38 |
| TAGCTA | 30908.62 |
| CCGCCG | 26249.18 |
| AGCTAG | 24860.48 |
| CACACG | 23587.17 |
| CGCCGC | 20163.76 |

The processor 231 may identify TAGCTA-like motifs based on a TAGCTA k-mer chosen for downstream analysis from an output of an associated prioritization pipeline. The TAGCTA k-mer may have a high prioritization score. The TAGCTA k-mer may not be repetitive (e.g., compared to CCTCCT or CCGCCG). The TAGCTA k-mer may show a slight enrichment for occurring near the start of coding sequences.

The TAGCTA motif to only known DRE, the TATCCAT/C-motif (Aravind et al. 2017), and only shares 67% similarity to that motifs. Therefore, due to its low similarity to any known DREs, TAGCTA can be considered a putative novel drought-responsive motif.

Other high scoring k-mers, identified by other models, similar in sequence to TAGCTA may be searched. Thereby, an entire putative drought-responsive element may be captured (i.e., identified k-mers of length six or eight may be captured). Three other k-mers may be nearly identical in sequence to TAGCTA, and may be identified in the top 25 k-mers identified by the prioritization pipeline: AGCTAG, CTAGCTAG, CTAGCT. These additional three k-mers may, for example, have similarities ranging from 62.5% to 67% compared with known DREs (therefore, can also be considered novel). Combining these k-mers may give, for example, a consensus motif of: AGCTAGCTAG (SEQ ID NO: 1). All four individual k-mers, hereafter referred to as TAGCTA-like motifs, may be used for downstream analysis to validate association with drought-responsive phenotypes. A distribution of TAGCTA-like motifs in promoter regions of all genes in which the k-mer is considered informative (e.g., in the top 100 scoring k-mers in at least one fold) may be analyzed.

With reference to FIG. 13, a graph 1300 illustrates position of TAGCTA-like motifs in promoters of genes. As illustrated, positions upstream of the CDS may be retrieved of instances where TAGCTA-like motifs are reported in, for example, the top 100 k-mers from all models tested. The processor 231 may validate novel drought-responsive k-mers using GWAS. The processor 231 may select genes for expression GWAS.

Figure 14:
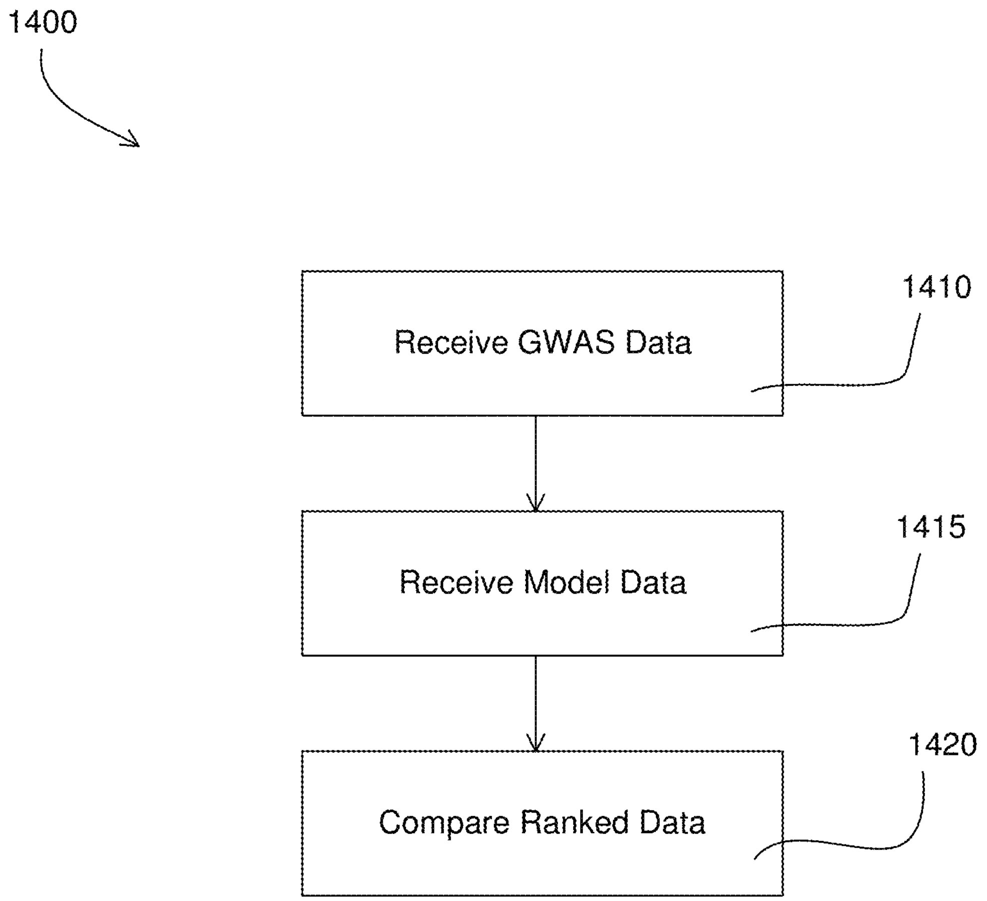
FIG. 14 depicts a flow diagram for an example method of validating novel cis-regulatory elements.

Turning to FIG. 14, a method of validating novel cis-regulatory elements 1400 may be implemented by a processor (e.g., processor 231 of FIG. 2) executing, for example, at least a portion of module 136 of FIG. 1, 236 of FIG. 2, or at least a portion of modules 610*a*-665*a* of FIG. 6A. In particular, the processor 231 may execute the GWAS data receiving module 640*a* to cause the processor 231 to, for example, receive GWAS data (block 1410). The processor 231 may execute the model output data receiving module 655*a* to cause the processor 231 to, for example, receive model output data (block 1415). The processor 231 may execute the novel Cis-regulatory element verification data generation module 660*a* to cause the processor 231 to, for example, compare ranked data (e.g., ranked Cis-regulatory element data (block 1420)).

As a particular example, the processor 231 may execute the sequence classification data generation module 630*a* (e.g., an optimization/model combination, etc.) to, for example, cause the processor 231 to combine outputs from at least two machine learning models (e.g., two different natural language processing models, etc.) to identify at least one genetic element. Alternatively, the processor 231 may execute the sequence classification data generation module 630*a* (e.g., an optimization/model combination, etc.) to, for example, cause the processor 231 to combine outputs from multiple different machine learning models to identify at least one genetic element.

To validate the results of using NLP methods to identify known or novel Cis-regulatory elements (e.g., putative drought-responsive cis-elements), GWAS may be performed on expression levels of a small set of genes when, for example, validation using wet lab techniques is unavailable. Previous GWAS results, based on four drought-responsive phenotypes: photosynthetic efficiency (PE), relative leaf area (RLA), water use efficiency (WUE), and leaf rolling (LR), may be used for validation. For example, primary and secondary gene models associated with the top 1,000 GAPIT ranked hits for each phenotype analyzed for the presence of TAGCTA-like motifs in their promoter sequence (3 kb upstream of the CDS) may be used. Patterns in the distribution of TAGCTA-like motifs may be compared across genotype to identify if differences in the position of TAGTCA-like motifs varied by genotype. Genotype-specific variation may be observed in both position and frequency of TAGCTA-like motifs in genes significantly associated with drought-related phenotypes (See FIGS. 13, 15, 17 and 19).

Expression of these genes may also vary across genotypes. For example, gene expression values from moderate-drought samples may be plotted for each genotype. Expression levels of these genes may be significantly associated with drought-related phenotypes that may also varied by genotype (See FIGS. 14, 16, 18 and 20).

Significant GWAS hits for each drought-associated phenotype that contained TAGCTA-like motifs ranged from 22 to 74 genes. A subset of these genes may be selected for expression GWAS based on genotypic variations in position of TAGCTA-like motifs in the promoter and genes expression (See Table 3).

Figure 15A:
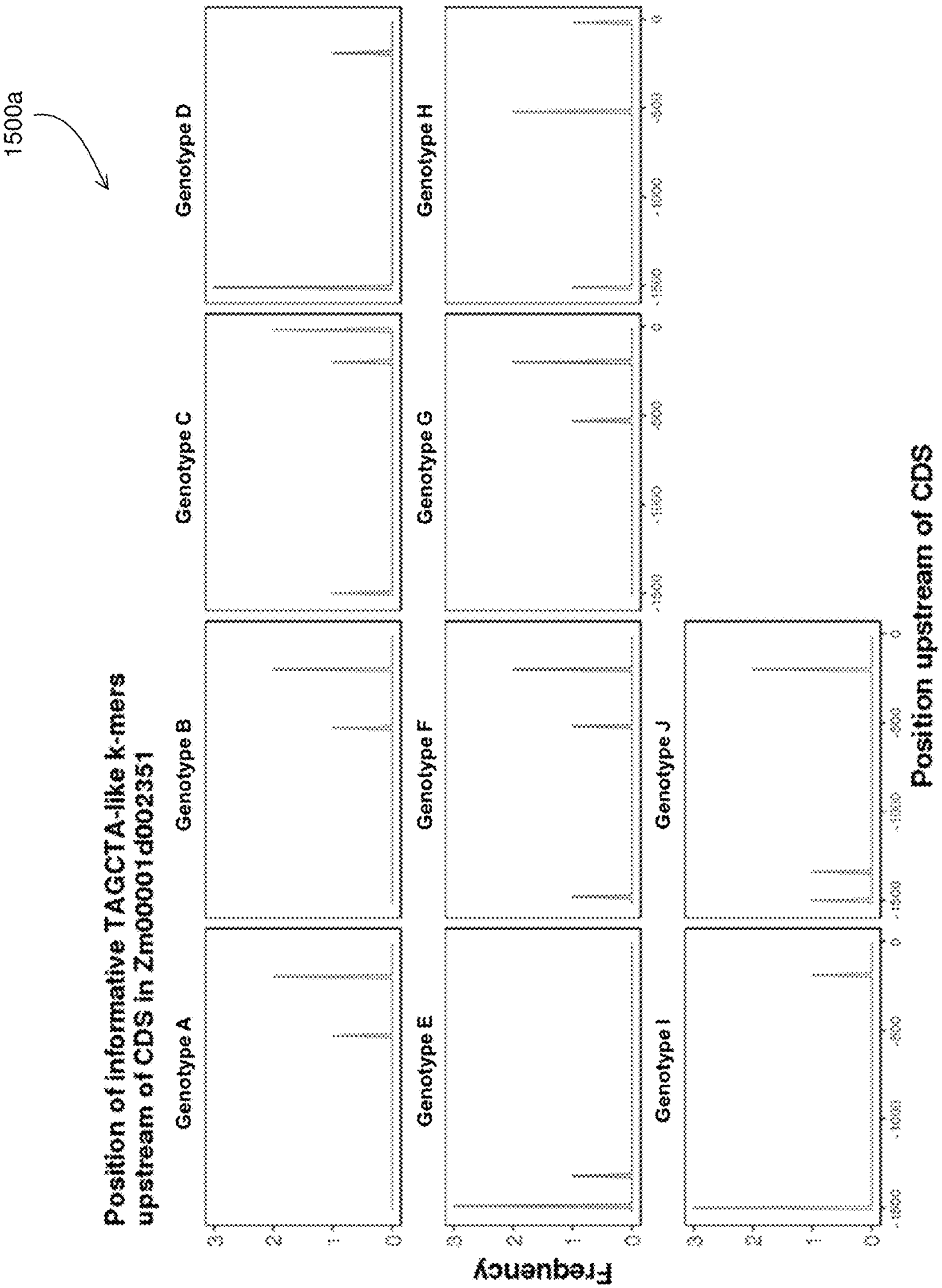
FIGS. 15A-C depict various example graphs of Zm0001d002351 gene data.
Figure 15B:
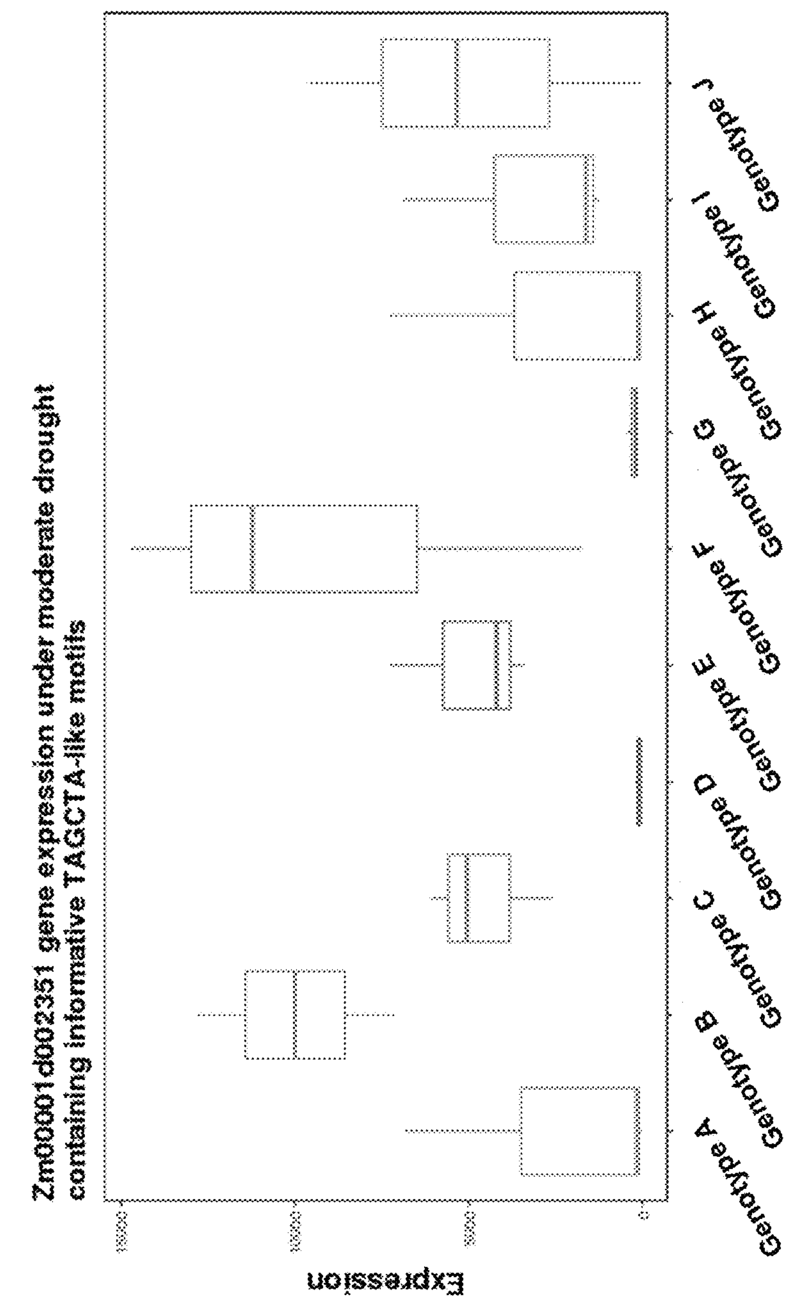
Figure 15C:
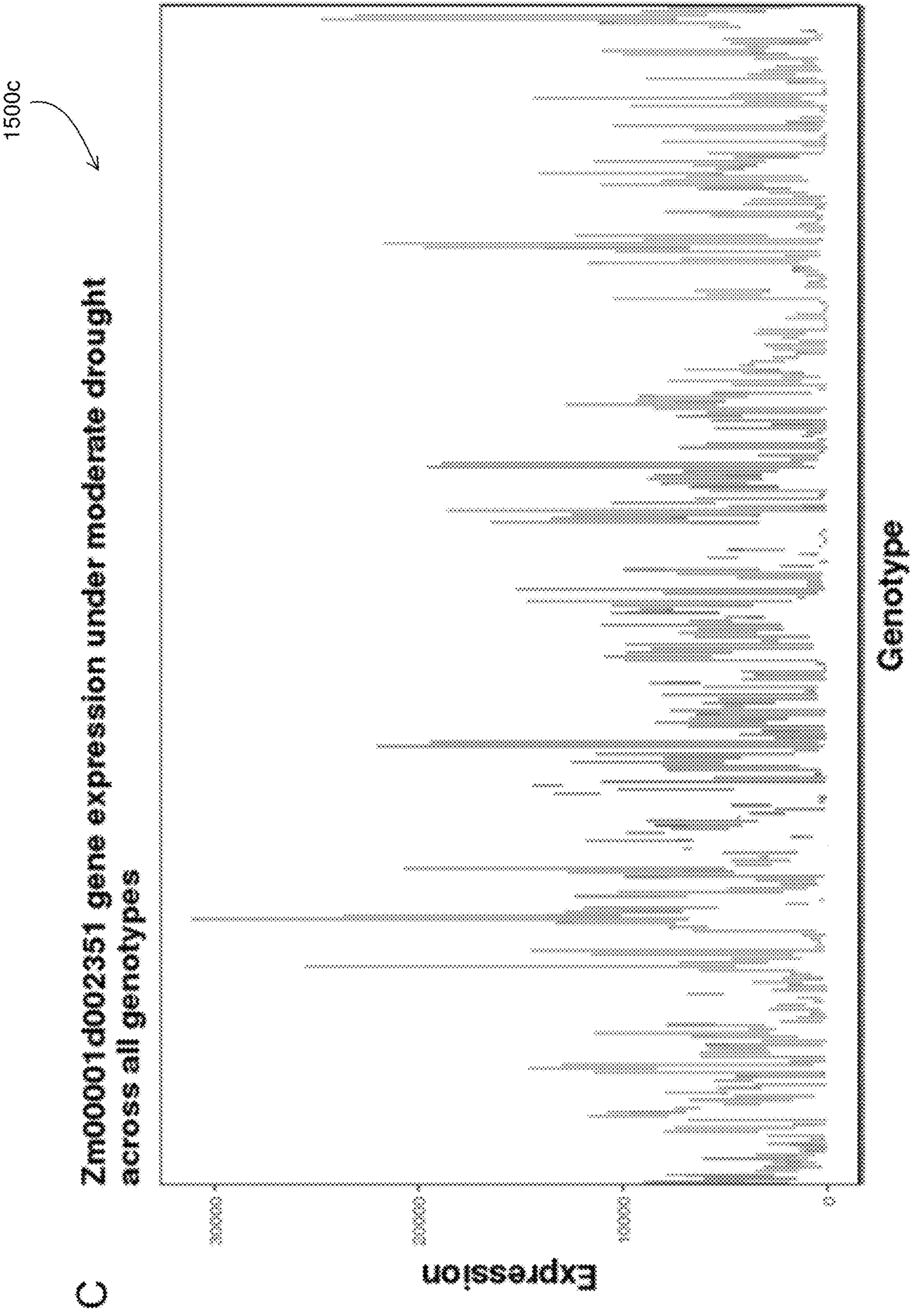

Turning to FIGS. 15A-C, a plurality of graphs 800*a-c* illustrate genotypic variation in position of TAGCTA-like motifs and gene expression of Zm00001d002351. The graphs 1500*a-c* may illustrate position of informative TAGCTA-like k-mers across genotypes in which they appear. "Informative" k-mers refers to k-mers present in the top 100 scoring k-mers by model output. The graphs 1500*a-c* may illustrate expression of Zm00001d002351 under moderate drought in genotypes that contained informative TAGCTA-like motifs in promoter regions. The graphs 1500*a-c* may illustrate expression of Zm00001d002351 across all genotypes under moderate drought conditions. Zm00001d002351 may be used as an example to visualize differences in position of TAGCTA-like motifs in promoter regions and expression variation across genotypes.

With respect to identification of drought-resistant elements in maize, twenty-one genes, that contained TAGCTA-like motifs, may be selected for validation using expression GWAS (eGWAS) based on criteria described herein. Of these twenty-one genes, five to six genes may be, for example, associated with each drought responsive phenotype (e.g., photosynthetic efficiency (PE), leaf rolling (LR), water use efficiency (WUE), relative leaf area (RLA), etc.).

TABLE 3

| GENE | DROUGHT ASSOCIATED PHENOTYPE |
|---|---|
| Zm00001d033304 | Leaf rolling |
| Zm00001d047994 | Leaf rolling |
| Zm00001d042886 | Leaf rolling |
| Zm00001d007954 | Leaf rolling |
| Zm00001d033068 | Leaf rolling |
| Zm00001d044272 | WUE |
| Zm00001d043166 | WUE |
| Zm00001d002351 | WUE |
| Zm00001d026223 | WUE |
| Zm00001d030526 | WUE |
| Zm00001d026042 | RLA |
| Zm00001d052457 | RLA |
| Zm00001d015217 | RLA |
| Zm00001d003931 | RLA |
| Zm00001d024952 | RLA |
| Zm00001d020810 | RLA |
| Zm00001d038576 | PE |
| Zm00001d006297 | PE |
| Zm00001d029461 | PE |
| Zm00001d039701 | PE |
| Zm00001d021736 | PE |

As illustrated above, Table 3 includes genes that may be selected for expression GWAS. Genes may be selected based on significant association with drought-responsive phenotypes, presence of TAGCTA-like motifs near the CDS, and variation in gene expression across genotypes. Count data for each gene may be used as a biological trait to be analyzed in both pre-drought and moderate drought conditions. Expression data may be checked for normality and outliers may be removed before downstream analysis. General linear mixed model may be used to estimate genotype effect, as well as, to estimate best linear unbiased prediction (BLUP) of genotypes for each gene. Genotype effect may be, for example, highly significant for all genes. Heritability of all genes may, for example, range from 24.5 to 94.7.

TABLE 4

| SUMMARY OF GWAS RESULTS | MODERATE DROUGHT (NUMBER OF GENES) | PRE-DROUGHT (NUMBER OF GENES) |
|---|---|---|
| Primary peaks corresponded to GOI | 12 | 12 |
| Secondary peaks present | 2 | 1 |
| No clear peak | 9 | 9 |

As illustrated above, Table 4 includes a summary of eGWAS results from twenty-one genes with expression as a biological trait. More than half of the genes used as the biological trait may be, for example, found in the top GWAS hits. Of the twenty-one genes, with expression used as the biological trait for GWAS analysis, twelve genes showed a strong primary peak that corresponded to SNPs associated with the gene of interest (GOI), including SNPs in regulatory regions upstream of the GOI (See Table 4). Two genes showed a strong secondary peak in separate chromosomes (See FIGS. 9 and 10). Zm00001d002351 has been characterized as a terpene synthase. The strong peak on chromosome two under moderate drought conditions correspond to SNPs associated with the Zm00001d002351 gene model, including SNPs in the 5'UTR and promoter region. The peak in chromosome one under both pre-drought and moderate drought conditions corresponds to a bZIP transcription factor, which constitute a class of proteins known to regulate terpene synthases (Spyropoulou 2012 PhD thesis).

Figure 16A:
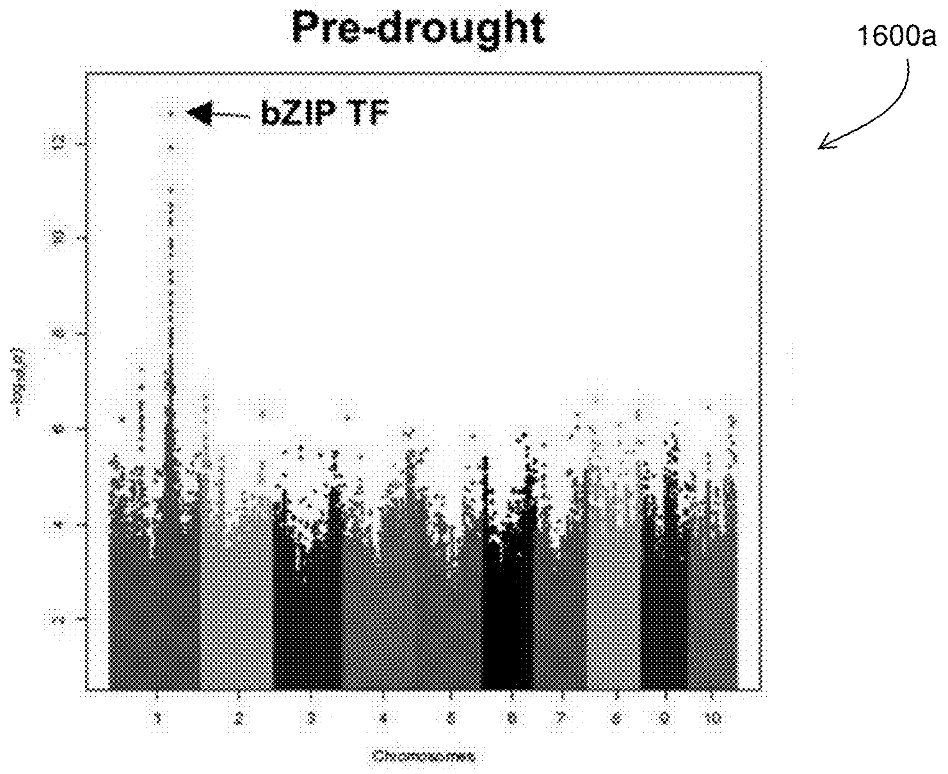
FIGS. 16A and 16B depict example eGWAS results for Zm00001d002351 gene data.
Figure 16B:
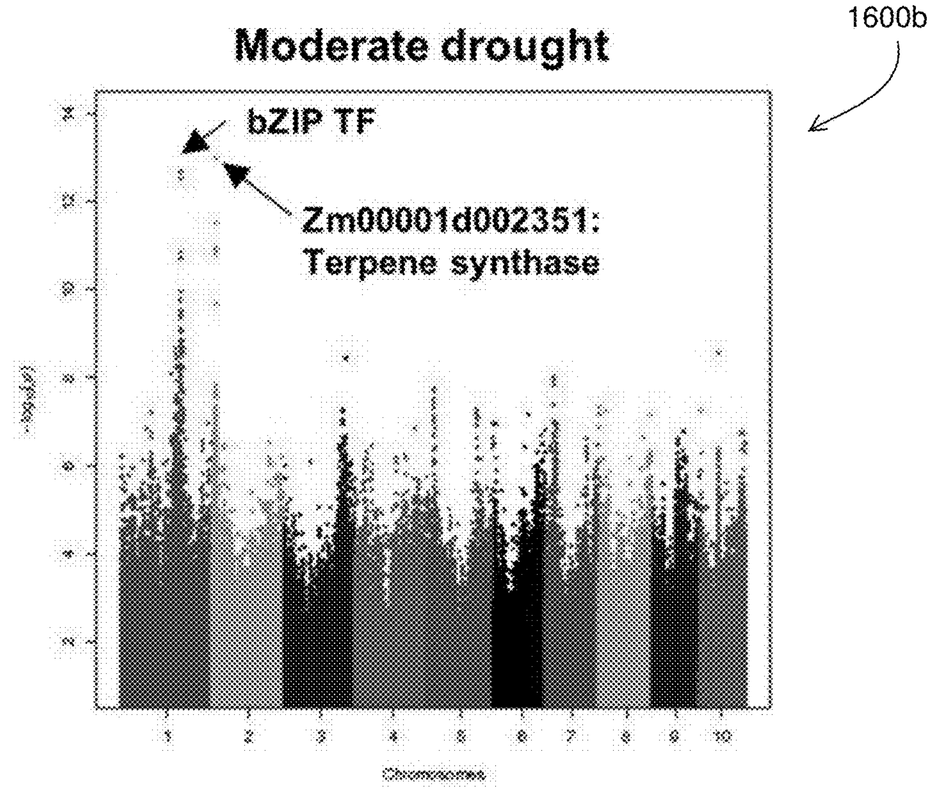

With reference to FIGS. 16A and 16B, graphs 1600*a,b* may illustrate eGWAS results for Zm00001d002351. As illustrated, a peak in chromosome two under moderate drought conditions may correspond to a gene of interest. The peak in chromosome one in both drought conditions corresponds to a bZIP transcription factor, which are a class of transcription factors known to regulate terpene synthases.

Figure 17A:
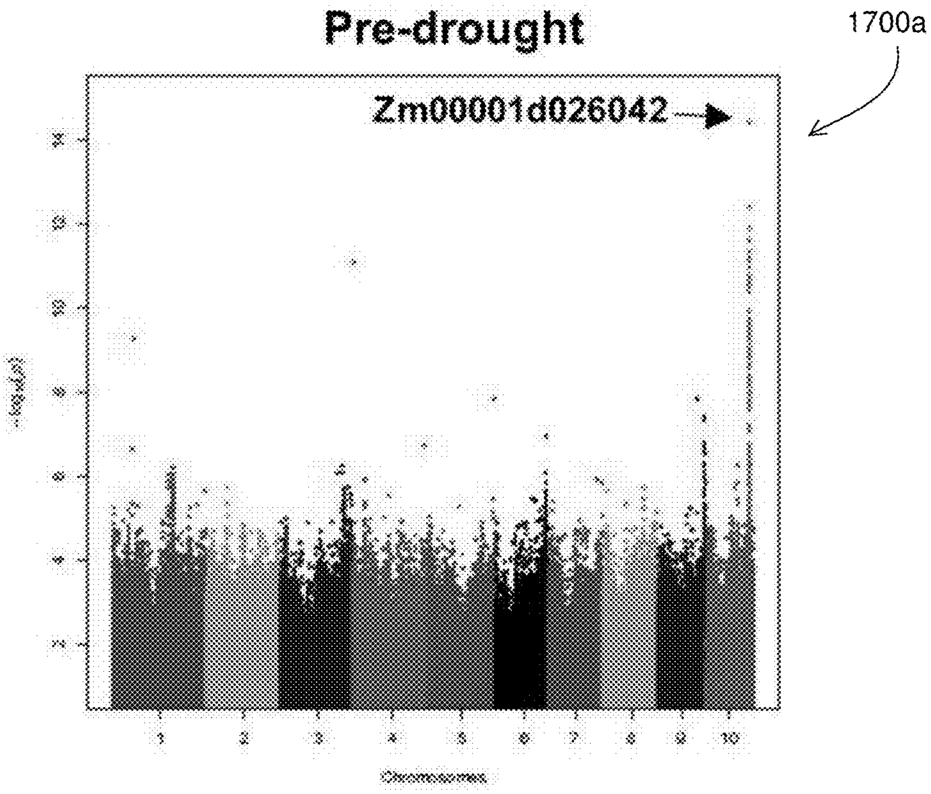
FIGS. 17A and 17B depict example eGWAS results for Zm00001d026042 gene data.
Figure 17B:
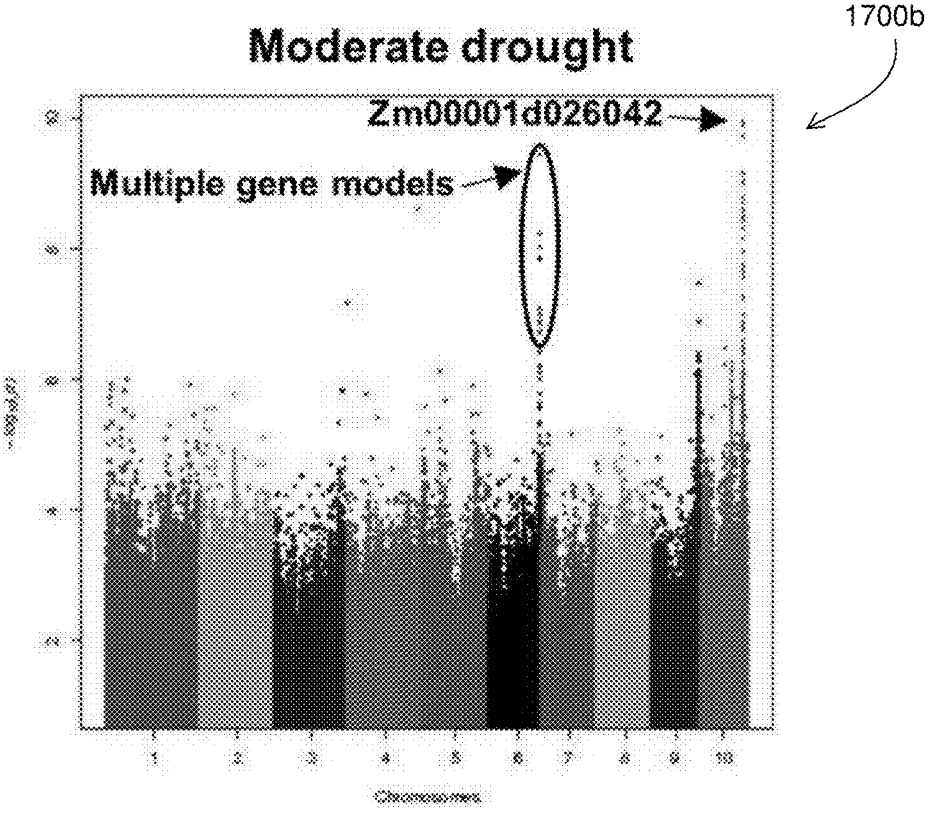

Turning to FIGS. 17A and 17B, graphs 1700*a,b* illustrates eGWAS results for Zm00001d026042, a gene that has not yet been functionally characterized, show a strong peak in chromosome ten, which correspond to SNPs associated with Zm00001d026042, including SNPs in the 5'UTR and promoter regions. The secondary peak contains SNPs within multiple gene models including several transcription factors. With additional reference to FIG. 10B, a graph 1000*b* illustrates eGWAS results for Zm00001d026042 with a peak on chromosome 10 corresponds to the Zm00001d026042 gene model. As further illustrated, a peak on chromosome eight under moderate drought conditions contains SNPs from multiple gene models including a NAC, MYB, and MADS box transcription factor.

The decreased cost of next-generation sequencing technologies has enabled RNA-seq and whole genome sequencing for large-scale experiments. This plethora of sequencing data along with advancements in computational capabilities allows for opportunities to develop innovative ways to interrogate NGS data. Natural language processing methods are a set of algorithms designed to detect context and sentiment in documents containing words and sentences, however, application of these algorithms to DNA and RNA sequences is a recent advancement and little evidence in the literature exists for application of these methods to cis-element discovery. For example, NLP methods may be performed using a combined dataset RNA-seq and whole genome sequencing (WGS) data across two-hundred forty-seven maize genotypes and successfully identified a set of novel drought-responsive cis-elements.

Different models may be used for preprocessing and scoring methods. High variation in the top 100 scoring k-mers identified by each model may be observed. Accordingly, outputs of a plurality of models may be combined, and weighting k-mers based on an associated score, model performance (auROC), and a frequency of appearance in multiple models, may improve a confidence of novel cis-element identification.

For example, known DREs may be significantly enriched in model outputs and a set of novel putative DREs may be identified. At least one such novel DRE may be verified using eGWAS. Expression of several genes significantly associated with four drought-responsive phenotypes that contained the novel TAGCTA-like motif may be demonstrated to be highly heritable, and that SNPs in the promoter region may be associated with variation in gene expression across genotypes. Furthermore, upstream transcriptional regulators of novel cis-elements may be identified by combing NLP approaches with eGWAS.

The processor 231 may take evolutionary relationships into account to, for example, improve NLP model performance. Evolutionary relationships may be taken into account when splitting sequence data into testing and training sets, thereby, model performance may be improved. For example, evolutionary relatedness may be accounted for by ensuring that all sequences from a gene model from multiple genotypes only appeared in either the training, development, or testing data sets. In other words, if a gene is predicted to be drought-responsive in multiple genotypes, all genotypic specific sequences corresponding to the promoter region for that gene all appeared in only data set.

Figure 18A:
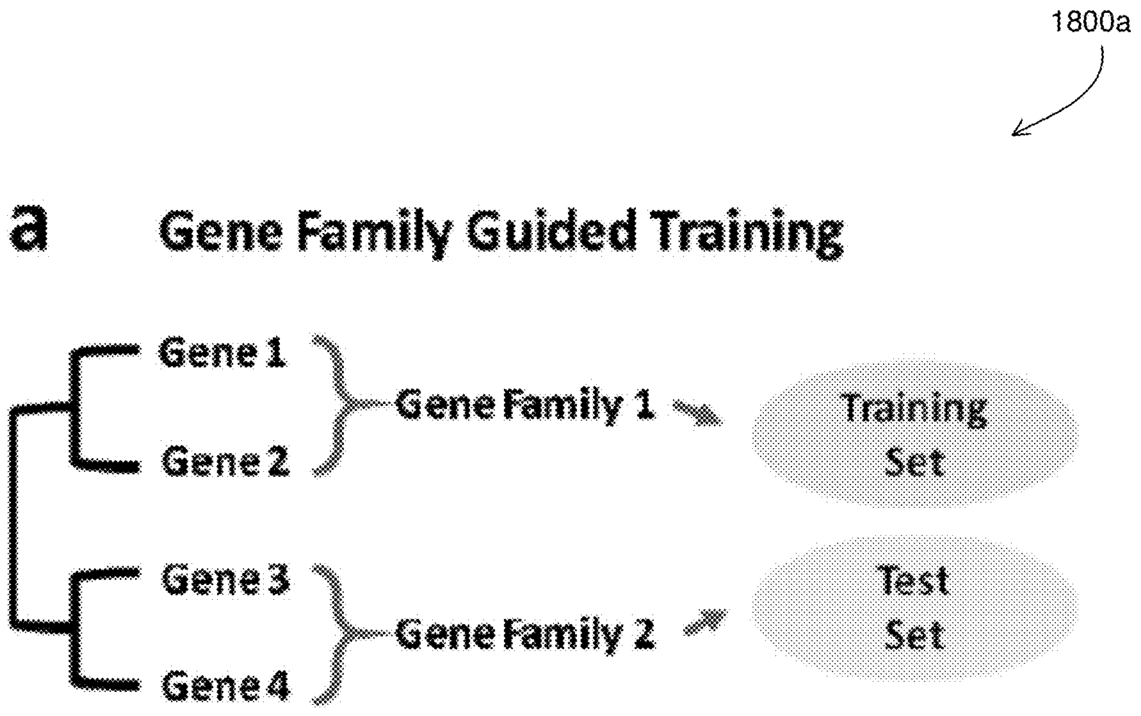
FIGS. 18A and 18B depict example evolutionary informed strategies for deep learning.
Figure 18B:
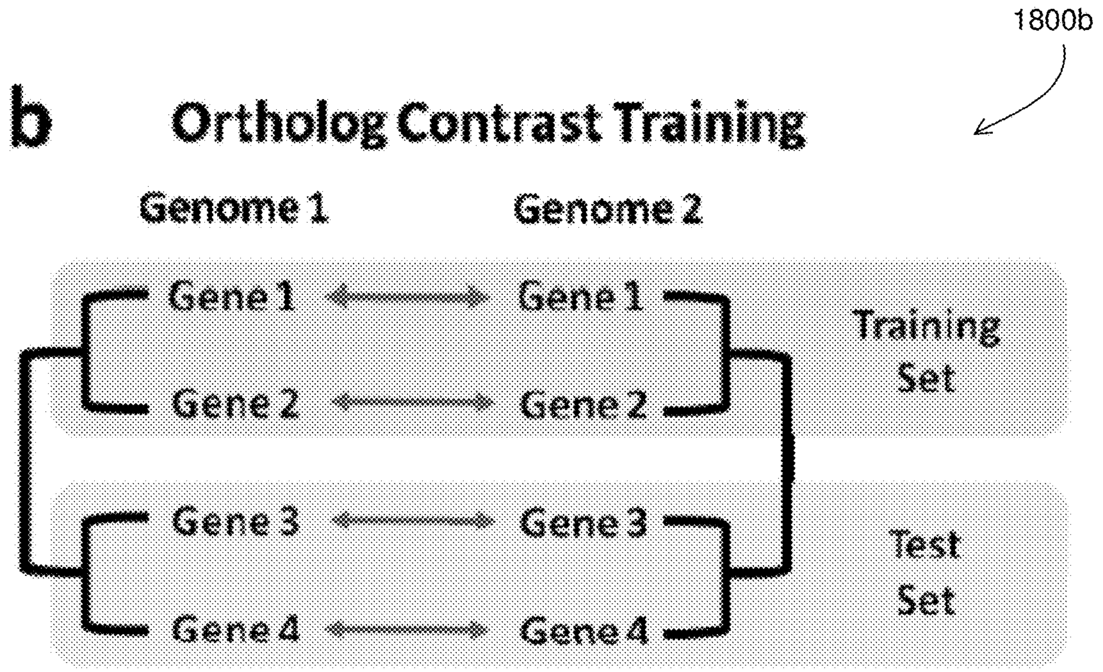

With reference to FIGS. 18A and 18B, if highly similar DNA sequences appear in all training, development, and testing datasets, the model may learn to make predictions based on sequence homology and not drought-responsiveness, and may result in models that are overfit. Use of evolutionary informed strategies for deep learning may include, as illustrated in FIG. 18A, prediction tasks involving a single species, genes are grouped into gene families before being further divided into training and test set, to prevent deep learning models from learning family-specific sequence features that are associated with target variables. Use of evolutionary informed strategies for deep learning may include, as illustrated in FIG. 18B, prediction tasks involving two species, orthologs are paired before being divided into training and test set, to eliminate evolutionary dependencies.

Figure 19:
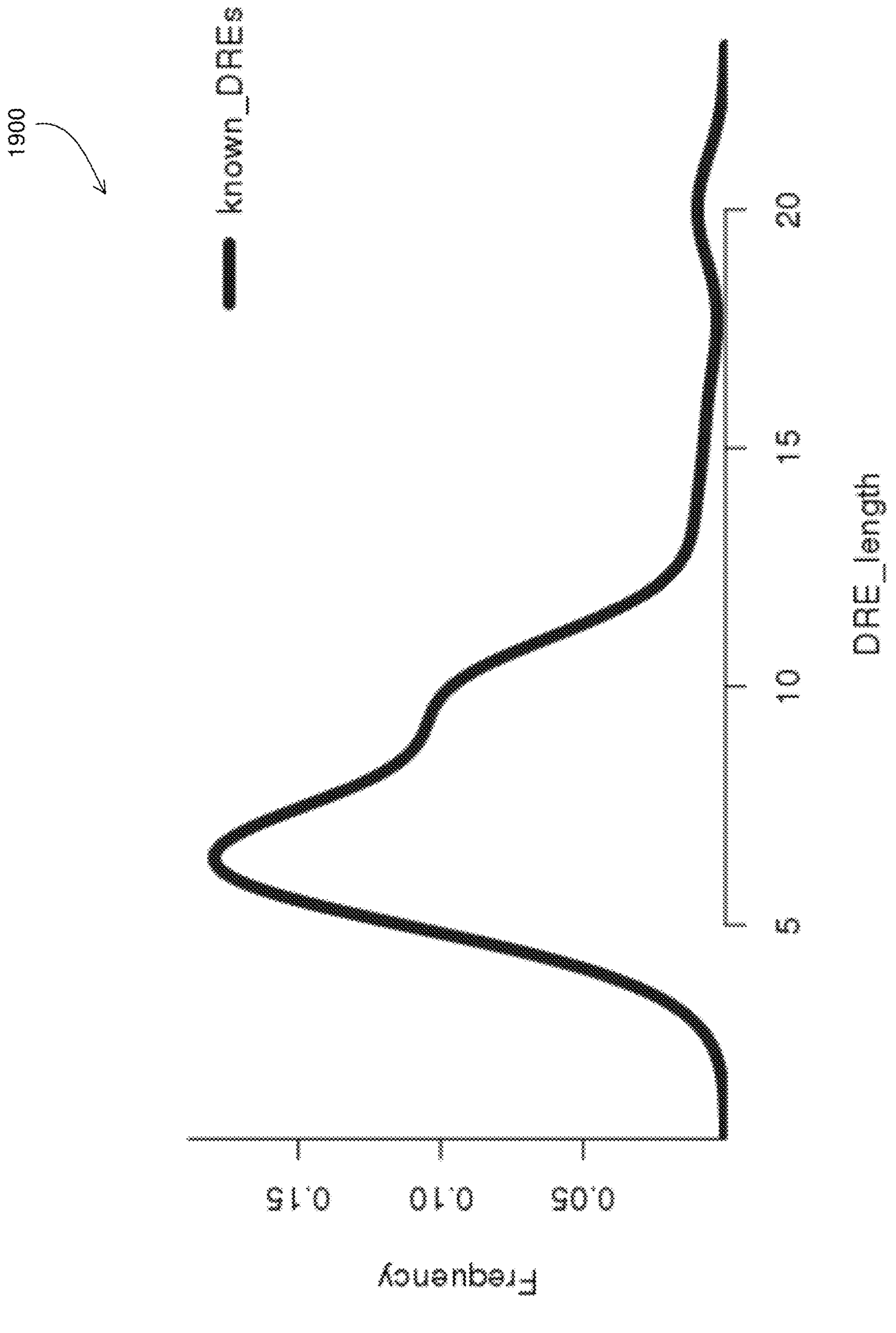
FIG. 19 depicts an example graph of lengths of know DREs verses frequency of occurrence.

Turning to FIG. 19, a graph 1900 illustrates a length of known DREs in maize. As illustrated, most known DREs in maize have a length of six base pairs. Thus, a k-mer of length six for identification of novel drought-responsive k-mers may be used.

TABLE 5

| DRE name | DRE sequence | SEQ ID NO: | Genetic source | cis-element length | Reference |
|---|---|---|---|---|---|
| TATCCAT/C-motif | TATCCAT | | miRNA | 7 | Aravind et al. 2017 |
| GA-motif | AAGGAAGA | | miRNA | 8 | Aravind et al. 2017 |
| LTR | CCGAAA | | miRNA | 6 | Aravind et al. 2017 |
| CCGTCC-box | CCGTCC | | miRNA | 6 | Aravind et al. 2017 |
| MNF1 | GTGCCCTT | | miRNA | 8 | Aravind et al. 2017 |
| ATCT-motif | AATCTAATCC | 2 | miRNA | 10 | Aravind et al. 2017 |
| GC-motif | CCCCCG | | miRNA | 6 | Aravind et al. 2017 |
| AE-box | AGAAACAT | | miRNA | 8 | Aravind et al. 2017 |
| GARE-motif | AAACAGA | | miRNA | 7 | Aravind et al. 2017 |
| TCT-motif | TCTTAC | | miRNA | 6 | Aravind et al. 2017 |
| RY-element | CATGCATG | | miRNA | 8 | Aravind et al. 2017 |
| 5UTR Py-rich stretch | TTTCTTCTCT | 3 | miRNA | 10 | Aravind et al. 2017 |
| TCA-element | CAGAAAAGGA | 4 | miRNA | 10 | Aravind et al. 2017 |
| ACE | GACACGTATG | 5 | miRNA | 10 | Aravind et al. 2017 |
| Box I | TTTCAAA | | miRNA | 7 | Aravind et al. 2017 |
| HSE | AAAAAATTTC | 6 | miRNA | 10 | Aravind et al. 2017 |
| TGA-element | AACGAC | | miRNA | 6 | Aravind et al. 2017 |
| Box-W1 | TTGACC | | miRNA | 6 | Aravind et al. 2017 |
| W box | TTGACC | | miRNA | 6 | Aravind et al. 2017 |
| CCAAT-box | CAACGG | | miRNA | 6 | Aravind et al. 2017 |
| CATT-motif | GCATTC | | miRNA | 6 | Aravind et al. 2017 |
| O2-site | GATGACATGG | 7 | miRNA | 10 | Aravind et al. 2017 |
| GCN4_motif | TGAGTCA | | miRNA | 7 | Aravind et al. 2017 |
| Box 4 | ATTAAT | | miRNA | 6 | Aravind et al. 2017 |

TABLE 5-continued

| DRE name | DRE sequence | SEQ ID NO: | Genetic source | cis-element length | Reference |
|---|---|---|---|---|---|
| CAT-box | GCCACT | | miRNA | 6 | Aravind et al. 2017 |
| GT1-motif | GGTTAA | | miRNA | 6 | Aravind et al. 2017 |
| I-box | GATATGG | | miRNA | 7 | Aravind et al. 2017 |
| AAGAA-motif | GAAAGAA | | miRNA | 7 | Aravind et al. 2017 |
| TC-rich repeats | ATTTTCTTCA | 8 | miRNA | 10 | Aravind et al. 2017 |
| GAG-motif | GAGAGAT | | miRNA | 7 | Aravind et al. 2017 |
| ABRE | GCAACGTGTC | 9 | miRNA | 10 | Aravind et al. 2017 |
| circadian | CAANNNNATC | 10 | miRNA | 10 | Aravind et al. 2017 |
| ARE | TGGTTT | | miRNA | 6 | Aravind et al. 2017 |
| CGTCA-motif | CGTCA | | miRNA | 5 | Aravind et al. 2017 |
| TGACG-motif | TGACG | | miRNA | 5 | Aravind et al. 2017 |
| Sp1 | CC(G/A)CCC | | miRNA | 6 | Aravind et al. 2017 |
| MBS | CAACTG | | miRNA | 6 | Aravind et al. 2017 |
| G-Box | CACGTT | | miRNA | 6 | Aravind et al. 2017 |
| Skn-1_motif | GTCAT | | miRNA | 5 | Aravind et al. 2017 |
| TATA-box | ATATAAT | | miRNA | 7 | Aravind et al. 2017 |
| CAAT-box | CCAAT | | miRNA | 5 | Aravind et al. 2017 |
| -300MOTIFZMZEIN | RTGAGTCAT | | gene | 9 | Mittal et al. 2018 |
| -314MOTIFZMSBE1 | ACATAAAATAAAAAAAGGCA | 11 | gene | 20 | Mittal et al. 2018 |
| ABREAZMRAB28 | GCCACGTGGG | 12 | gene | 10 | Mittal et al. 2018 |
| ABREBZMRAB28 | TCCACGTCTC | 13 | gene | 10 | Mittal et al. 2018 |
| ANAERO1CONSENSUS | AAACAAA | | gene | 7 | Mittal et al. 2018 |
| ANAERO3CONSENSUS | TCATCAC | | gene | 7 | Mittal et al. 2018 |
| ANAEROBICCISZMGAPC4 | CGAAACCAGCAACGGTCCAG | 14 | gene | 20 | Mittal et al. 2018 |
| ARECOREZMGAPC4 | AGCAACGGTC | 15 | gene | 10 | Mittal et al. 2018 |
| C1MOTIFZMBZ2 | TAACTSAGTTA | 16 | gene | 11 | Mittal et al. 2018 |
| DOFCOREZM | AAAG | | gene | 4 | Mittal et al. 2018 |
| DRE1COREZMRAB17 | ACCGAGA | | gene | 7 | Mittal et al. 2018 |
| DRECRTCOREAT | RCCGAC | | gene | 6 | Mittal et al. 2018 |
| GCAACREPEATZMZEIN | GCAACGCAAC | 17 | gene | 10 | Mittal et al. 2018 |

TABLE 5-continued

| DRE name | DRE sequence | SEQ ID NO: | Genetic source | cis-element length | Reference |
|---|---|---|---|---|---|
| GCBP2ZMGAPC4 | GTGGGCCCG | | gene | 9 | Mittal et al. 2018 |
| IDRSZMFER1 | CACGAGSCCKCCAC | 18 | gene | 14 | Mittal et al. 2018 |
| INTRONLOWER | TGCAGG | | gene | 6 | Mittal et al. 2018 |
| INTRONUPPER | MAGGTAAGT | | gene | 9 | Mittal et al. 2018 |
| MNF1ZMPPC1 | GTGCCCTT | | gene | 8 | Mittal et al. 2018 |
| MYBPLANT | MACCWAMC | | gene | 8 | Mittal et al. 2018 |
| MYBPZM | CCWACC | | gene | 6 | Mittal et al. 2018 |
| OCSENHANMOTIFAT | ACGTAAGCGCTTACGT | 19 | gene | 16 | Mittal et al. 2018 |
| OCTAMOTIF2 | CGCGGCAT | | gene | 8 | Mittal et al. 2018 |
| OPAQUE2ZMB32 | GATGAYRTGG | 20 | gene | 10 | Mittal et al. 2018 |
| POLASIG3 | AATAAT | | gene | 6 | Mittal et al. 2018 |
| QELEMENTZMZM13 | AGGTCA | | gene | 6 | Mittal et al. 2018 |
| RYREPEAT4 | TCCATGCATGCAC | 21 | gene | 13 | Mittal et al. 2018 |
| SPHZMC1 | CGTCCATGCAT | 22 | gene | 11 | Mittal et al. 2018 |
| TATAPVTRNALEU | TTTATATA | | gene | 8 | Mittal et al. 2018 |
| DRE | A/GCCGAC | | gene | 6 | Liu et al. 2013 |

As illustrated below, Table 6 includes a list of known DREs motifs split into 6-mers.

TABLE 6

| DRE name | DRE sequence |
|---|---|
| 5UTR Py-rich stretch-0-0 | TTTCTT |
| 5UTR Py-rich stretch-1-0 | TTCTTC |
| 5UTR Py-rich stretch-2-0 | TCTTCT |
| 5UTR Py-rich stretch-3-0 | CTTCTC |
| ?300MOTIFZMZEIN-0-0 | ATGAGT |
| ?300MOTIFZMZEIN-0-1 | GTGAGT |
| ?300MOTIFZMZEIN-1-0 | TGAGTC |
| ?300MOTIFZMZEIN-2-0 | GAGTCA |
| ?314MOTIFZMSBE1-0-0 | ACATAA |
| ?314MOTIFZMSBE1-1-0 | CATAAA |
| ?314MOTIFZMSBE1-2-0 | ATAAAA |
| ?314MOTIFZMSBE1-3-0 | TAAAAT |
| ?314MOTIFZMSBE1-4-0 | AAAATA |
| ?314MOTIFZMSBE1-5-0 | AAATAA |
| ?314MOTIFZMSBE1-6-0 | AATAAA |
| ?314MOTIFZMSBE1-7-0 | ATAAAA |
| ?314MOTIFZMSBE1-8-0 | TAAAAA |

TABLE 6-continued

| DRE name | DRE sequence |
|---|---|
| ?314MOTIFZMSBE1-9-0 | AAAAAA |
| ?314MOTIFZMSBE1-10-0 | AAAAAA |
| ?314MOTIFZMSBE1-11-0 | AAAAAG |
| ?314MOTIFZMSBE1-12-0 | AAAAGG |
| ?314MOTIFZMSBE1-13-0 | AAAGGC |
| AAGAA-motif-0-0 | GAAAGA |
| ABRE-0-0 | GCAACG |
| ABRE-1-0 | CAACGT |
| ABRE-2-0 | AACGTG |
| ABRE-3-0 | ACGTGT |
| ABREAZMRAB28-0-0 | GCCACG |
| ABREAZMRAB28-1-0 | CCACGT |
| ABREAZMRAB28-2-0 | CACGTG |
| ABREAZMRAB28-3-0 | ACGTGG |
| ABREBZMRAB28-0-0 | TCCACG |
| ABREBZMRAB28-1-0 | CCACGT |
| ABREBZMRAB28-2-0 | CACGTC |
| ABREBZMRAB28-3-0 | ACGTCT |

TABLE 6-continued

| DRE name | DRE sequence |
|---|---|
| ACE-0-0 | GACACG |
| ACE-1-0 | ACACGT |
| ACE-2-0 | CACGTA |
| ACE-3-0 | ACGTAT |
| AE-box-0-0 | AGAAAC |
| AE-box-1-0 | GAAACA |
| ANAERO1CONSENSUS-0-0 | AAACAA |
| ANAERO3CONSENSUS-0-0 | TCATCA |
| ANAEROBICCISZMGAPC4-0-0 | CGAAAC |
| ANAEROBICCISZMGAPC4-1-0 | GAAACC |
| ANAEROBICCISZMGAPC4-2-0 | AAACCA |
| ANAEROBICCISZMGAPC4-3-0 | AACCAG |
| ANAEROBICCISZMGAPC4-4-0 | ACCAGC |
| ANAEROBICCISZMGAPC4-5-0 | CCAGCA |
| ANAEROBICCISZMGAPC4-6-0 | CAGCAA |
| ANAEROBICCISZMGAPC4-7-0 | AGCAAC |
| ANAEROBICCISZMGAPC4-8-0 | GCAACG |
| ANAEROBICCISZMGAPC4-9-0 | CAACGG |
| ANAEROBICCISZMGAPC4-10-0 | AACGGT |
| ANAEROBICCISZMGAPC4-11-0 | ACGGTC |
| ANAEROBICCISZMGAPC4-12-0 | CGGTCC |
| ANAEROBICCISZMGAPC4-13-0 | GGTCCA |
| ARECOREZMGAPC4-0-0 | AGCAAC |
| ARECOREZMGAPC4-1-0 | GCAACG |
| ARECOREZMGAPC4-2-0 | CAACGG |
| ARECOREZMGAPC4-3-0 | AACGGT |
| ATCT-motif-0-0 | AATCTA |
| ATCT-motif-1-0 | ATCTAA |
| ATCT-motif-2-0 | TCTAAT |
| ATCT-motif-3-0 | CTAATC |
| Box I-0-0 | TTTCAA |
| C1MOTIFZMBZ2-0-0 | TAACTG |
| C1MOTIFZMBZ2-0-1 | TAACTC |
| C1MOTIFZMBZ2-1-0 | AACTGA |
| C1MOTIFZMBZ2-1-1 | AACTCA |
| C1MOTIFZMBZ2-2-0 | ACTGAG |
| C1MOTIFZMBZ2-2-1 | ACTCAG |
| C1MOTIFZMBZ2-3-0 | CTGAGT |

TABLE 6-continued

| DRE name | DRE sequence |
|---|---|
| C1MOTIFZMBZ2-3-1 | CTCAGT |
| C1MOTIFZMBZ2-4-0 | TGAGTT |
| C1MOTIFZMBZ2-4-1 | TCAGTT |
| DRE1COREZMRAB17-0-0 | ACCGAG |
| GA-motif-0-0 | AAGGAA |
| GA-motif-1-0 | AGGAAG |
| GAG-motif-0-0 | GAGAGA |
| GARE-motif-0-0 | AAACAG |
| GCAACREPEATZMZEIN-0-0 | GCAACG |
| GCAACREPEATZMZEIN-1-0 | CAACGC |
| GCAACREPEATZMZEIN-2-0 | AACGCA |
| GCAACREPEATZMZEIN-3-0 | ACGCAA |
| GCBP2ZMGAPC4-0-0 | GTGGGC |
| GCBP2ZMGAPC4-1-0 | TGGGCC |
| GCBP2ZMGAPC4-2-0 | GGGCCC |
| GCN4_motif-0-0 | TGAGTC |
| HSE-0-0 | AAAAAA |
| HSE-1-0 | AAAAAT |
| HSE-2-0 | AAAATT |
| HSE-3-0 | AAATTT |
| I-box-0-0 | GATATG |
| IDRSZMFER1-0-0 | CACGAG |
| IDRSZMFER1-1-0 | ACGAGG |
| IDRSZMFER1-1-1 | ACGAGC |
| IDRSZMFER1-2-0 | CGAGGC |
| IDRSZMFER1-2-1 | CGAGCC |
| IDRSZMFER1-3-0 | GAGGCC |
| IDRSZMFER1-3-1 | GAGCCC |
| IDRSZMFER1-4-0 | AGGCCG |
| IDRSZMFER1-4-1 | AGGCCT |
| IDRSZMFER1-4-2 | AGCCCG |
| IDRSZMFER1-4-3 | AGCCCT |
| IDRSZMFER1-5-0 | GGCCGC |
| IDRSZMFER1-5-1 | GGCCTC |
| IDRSZMFER1-5-2 | GCCCGC |
| IDRSZMFER1-5-3 | GCCCTC |
| IDRSZMFER1-6-0 | GCCGCC |
| IDRSZMFER1-6-1 | GCCTCC |
| IDRSZMFER1-6-2 | CCCGCC |

TABLE 6-continued

| DRE name | DRE sequence |
|---|---|
| IDRSZMFER1-6-3 | CCCTCC |
| IDRSZMFER1-7-0 | CCGCCA |
| IDRSZMFER1-7-1 | CCTCCA |
| INTRONUPPER-0-0 | AAGGTA |
| INTRONUPPER-0-1 | CAGGTA |
| INTRONUPPER-1-0 | AGGTAA |
| INTRONUPPER-2-0 | GGTAAG |
| MNF1-0-0 | GTGCCC |
| MNF1-1-0 | TGCCCT |
| MNF1ZMPPC1-0-0 | GTGCCC |
| MNF1ZMPPC1-1-0 | TGCCCT |
| MYBPLANT-0-0 | AACCAA |
| MYBPLANT-0-1 | AACCTA |
| MYBPLANT-0-2 | CACCAA |
| MYBPLANT-0-3 | CACCTA |
| MYBPLANT-1-0 | ACCAAA |
| MYBPLANT-1-1 | ACCAAC |
| MYBPLANT-1-2 | ACCTAA |
| MYBPLANT-1-3 | ACCTAC |
| O2-site-0-0 | GATGAC |
| O2-site-1-0 | ATGACA |
| O2-site-2-0 | TGACAT |
| O2-site-3-0 | GACATG |
| OCSENHANMOTIFAT-0-0 | ACGTAA |
| OCSENHANMOTIFAT-1-0 | CGTAAG |
| OCSENHANMOTIFAT-2-0 | GTAAGC |
| OCSENHANMOTIFAT-3-0 | TAAGCG |
| OCSENHANMOTIFAT-4-0 | AAGCGC |
| OCSENHANMOTIFAT-5-0 | AGCGCT |
| OCSENHANMOTIFAT-6-0 | GCGCTT |
| OCSENHANMOTIFAT-7-0 | CGCTTA |
| OCSENHANMOTIFAT-8-0 | GCTTAC |
| OCSENHANMOTIFAT-9-0 | CTTACG |
| OCTAMOTIF2-0-0 | CGCGGC |
| OCTAMOTIF2-1-0 | GCGGCA |
| OPAQUE2ZMB32-0-0 | GATGAC |
| OPAQUE2ZMB32-0-1 | GATGAT |
| OPAQUE2ZMB32-1-0 | ATGACA |

TABLE 6-continued

| DRE name | DRE sequence |
|---|---|
| OPAQUE2ZMB32-1-1 | ATGACG |
| OPAQUE2ZMB32-1-2 | ATGATA |
| OPAQUE2ZMB32-1-3 | ATGATG |
| OPAQUE2ZMB32-2-0 | TGACAT |
| OPAQUE2ZMB32-2-1 | TGACGT |
| OPAQUE2ZMB32-2-2 | TGATAT |
| OPAQUE2ZMB32-2-3 | TGATGT |
| OPAQUE2ZMB32-3-0 | GACATG |
| OPAQUE2ZMB32-3-1 | GACGTG |
| OPAQUE2ZMB32-3-2 | GATATG |
| OPAQUE2ZMB32-3-3 | GATGTG |
| RY-element-0-0 | CATGCA |
| RY-element-1-0 | ATGCAT |
| RYREPEAT4-0-0 | TCCATG |
| RYREPEAT4-1-0 | CCATGC |
| RYREPEAT4-2-0 | CATGCA |
| RYREPEAT4-3-0 | ATGCAT |
| RYREPEAT4-4-0 | TGCATG |
| RYREPEAT4-5-0 | GCATGC |
| RYREPEAT4-6-0 | CATGCA |
| SPHZMC1-0-0 | CGTCCA |
| SPHZMC1-1-0 | GTCCAT |
| SPHZMC1-2-0 | TCCATG |
| SPHZMC1-3-0 | CCATGC |
| SPHZMC1-4-0 | CATGCA |
| TATA-box-0-0 | ATATAA |
| TATAPVTRNALEU-0-0 | TTTATA |
| TATAPVTRNALEU-1-0 | TTATAT |
| TATCCAT/C-motif-0-0 | TATCCA |
| TC-rich repeats-0-0 | ATTTTC |
| TC-rich repeats-1-0 | TTTTCT |
| TC-rich repeats-2-0 | TTTCTT |
| TC-rich repeats-3-0 | TTCTTC |
| TCA-element-0-0 | CAGAAA |
| TCA-element-1-0 | AGAAAA |
| TCA-element-2-0 | GAAAAG |
| TCA-element-3-0 | AAAAGG |

Figure 20:
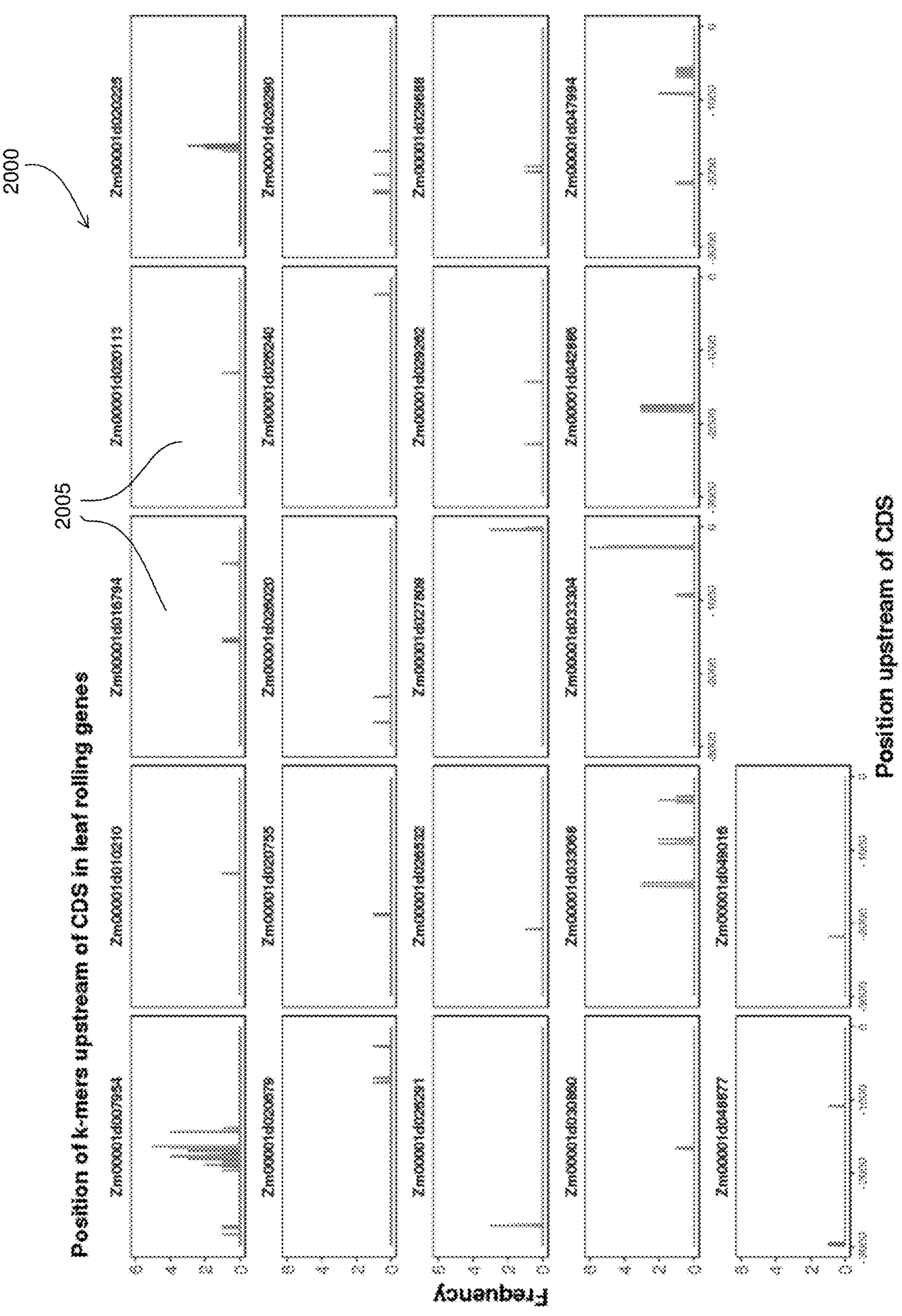
FIG. 20 depicts a plurality of example graphs that illustrate genes associated with leaf rolling phenotypes in response to drought that contain TAGCTA-like motifs in their promoter sequence.

With reference to FIG. 20, a plurality 2000 of graphs 2005 illustrate genes associated with leaf rolling phenotypes in response to drought that contain TAGCTA-like motifs in their promoter sequence. Each line may represent a different genotype. As illustrated in FIG. 20, genotype-specific distribution and frequency of TAGCTA-like motifs in promoter regions may be observed.

Figure 21:
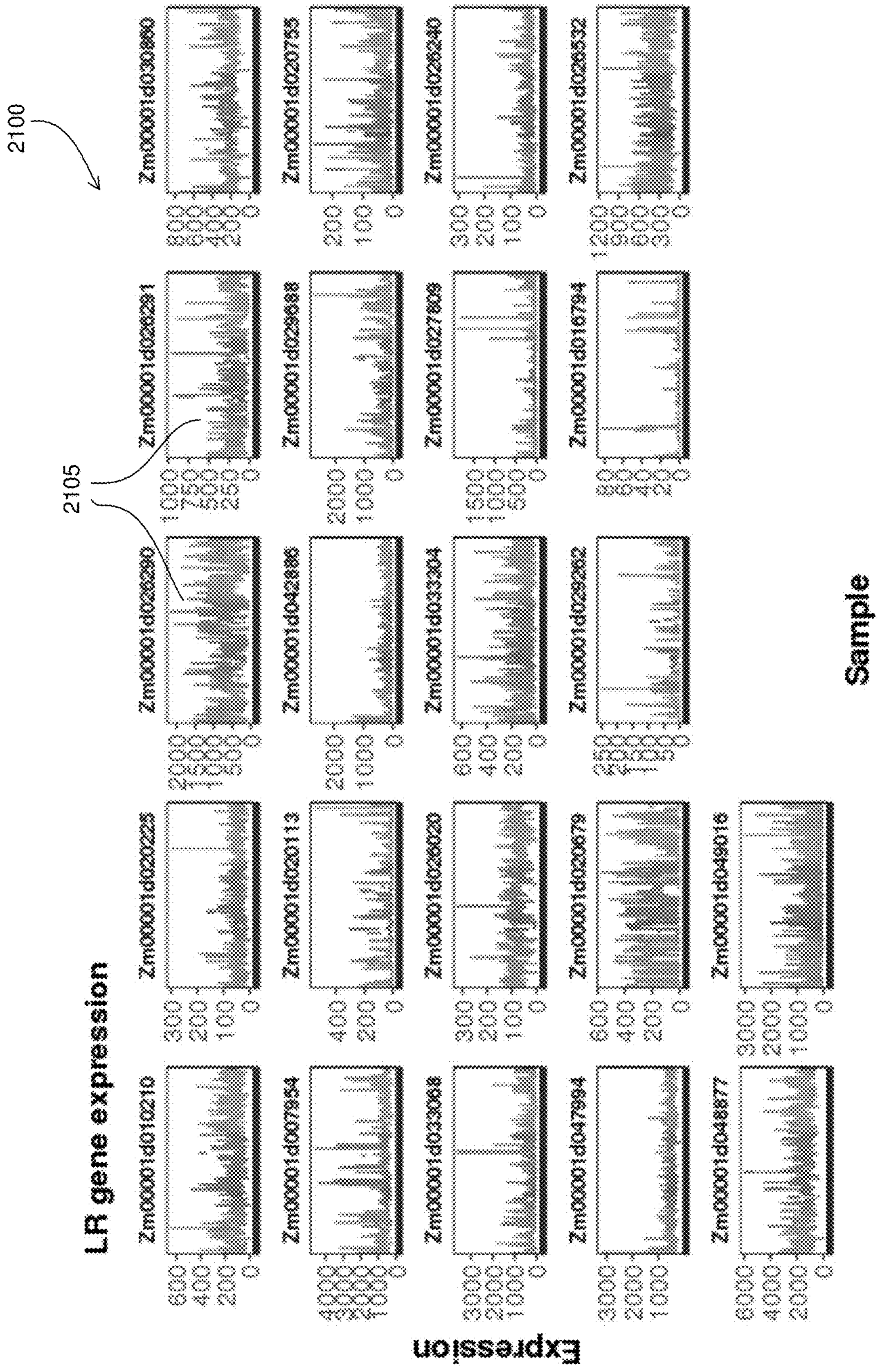
FIG. 21 depicts a plurality of example graphs that illustrate expression of genes associated with leaf rolling phenotypes in response to drought that contain TAGCTA-like motifs in their promoter sequence.

Turning to FIG. 21, a plurality 2100 of graphs 2105 illustrate expression of genes associated with leaf rolling phenotypes in response to drought that contain TAGCTA-like motifs in their promoter sequence. Each line may represent a different genotype (Sample). As illustrated in FIG. 21, expression of genes may vary by genotype.

Figure 22:
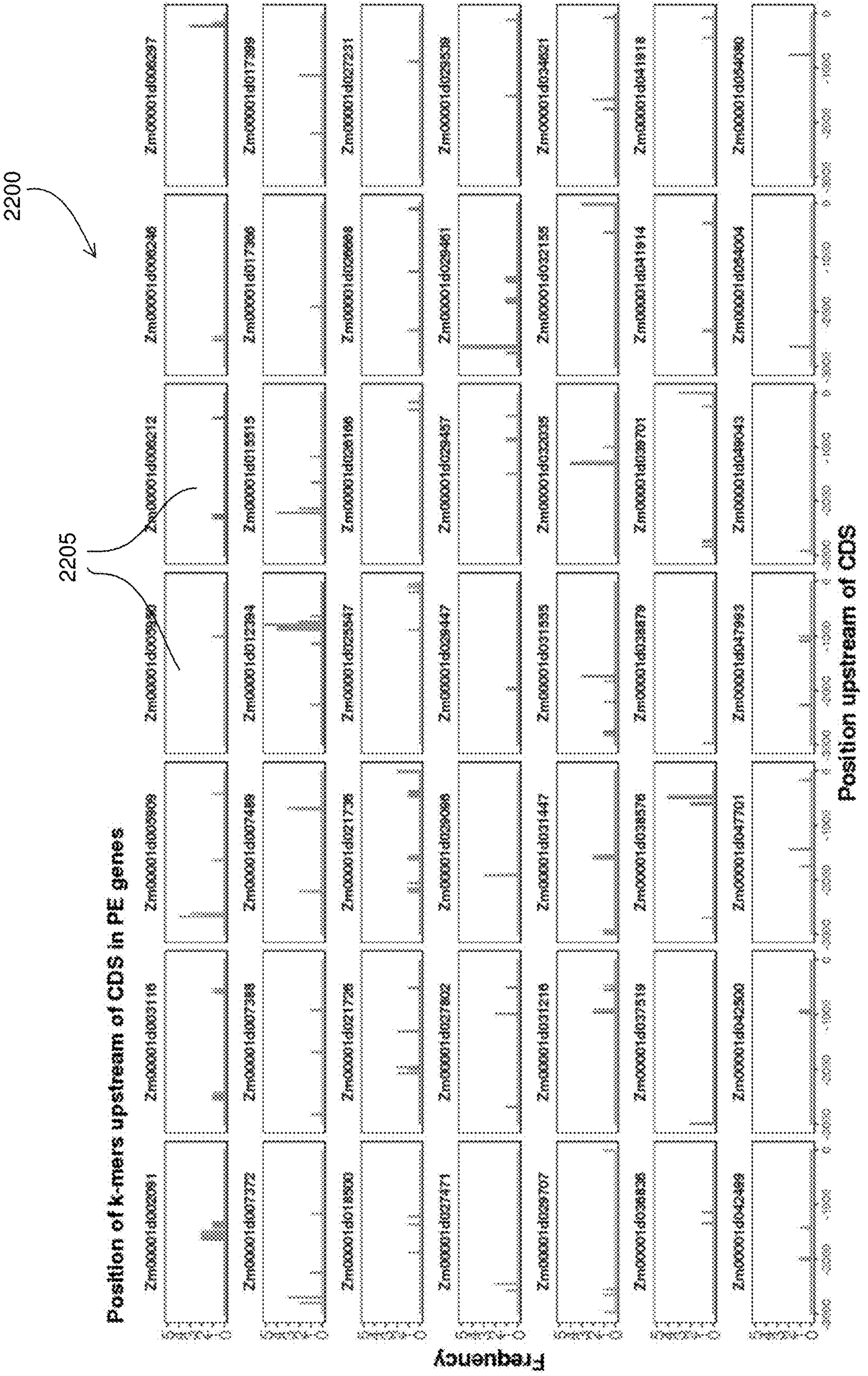
FIG. 22 depicts a plurality of example graphs that illustrate genes associated with photosynthetic efficiency phenotypes in response to drought that contain TAGCTA-like motifs in their promoter sequence.

With reference to FIG. 22, a plurality 2200 of graphs 2205 illustrate genes associated with photosynthetic efficiency phenotypes in response to drought that contain TAGCTA-like motifs in their promoter sequence. Each line may represent a different genotype. As illustrated in FIG. 22, genotype-specific distribution and frequency of TAGCTA-like motifs in promoter regions may be observed.

Figure 23:
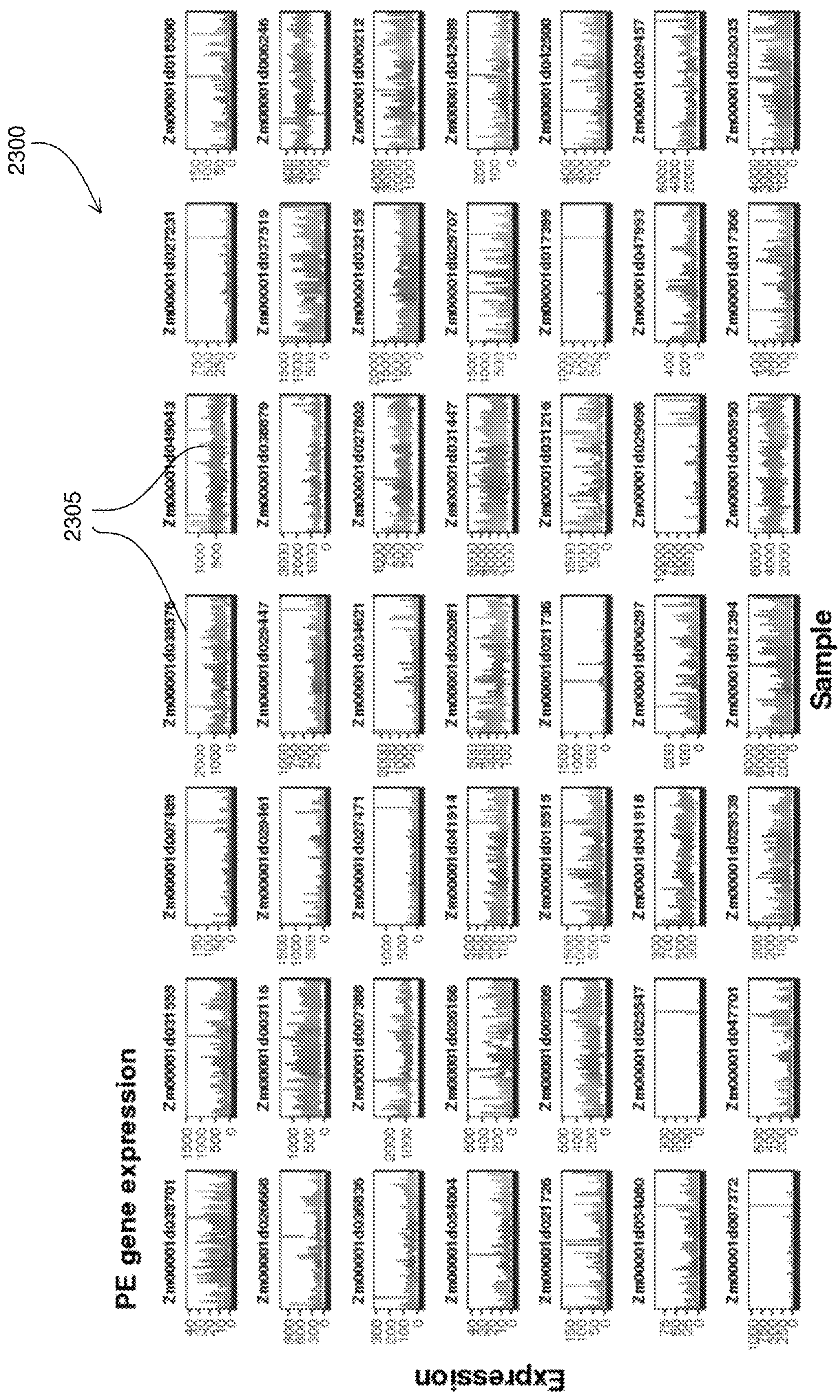
FIG. 23 depicts a plurality of example graphs that illustrate expression of genes associated with photosynthetic efficiency phenotypes in response to drought that contain TAGCTA-like motifs in their promoter sequence.

Turning to FIG. 23, a plurality 2300 of graphs 2305 illustrate expression of genes associated with photosynthetic efficiency phenotypes in response to drought that contain TAGCTA-like motifs in their promoter sequence. Each line may represent a different genotype. As illustrated in FIG. 23, expression of genes may vary by genotype.

Figure 24:
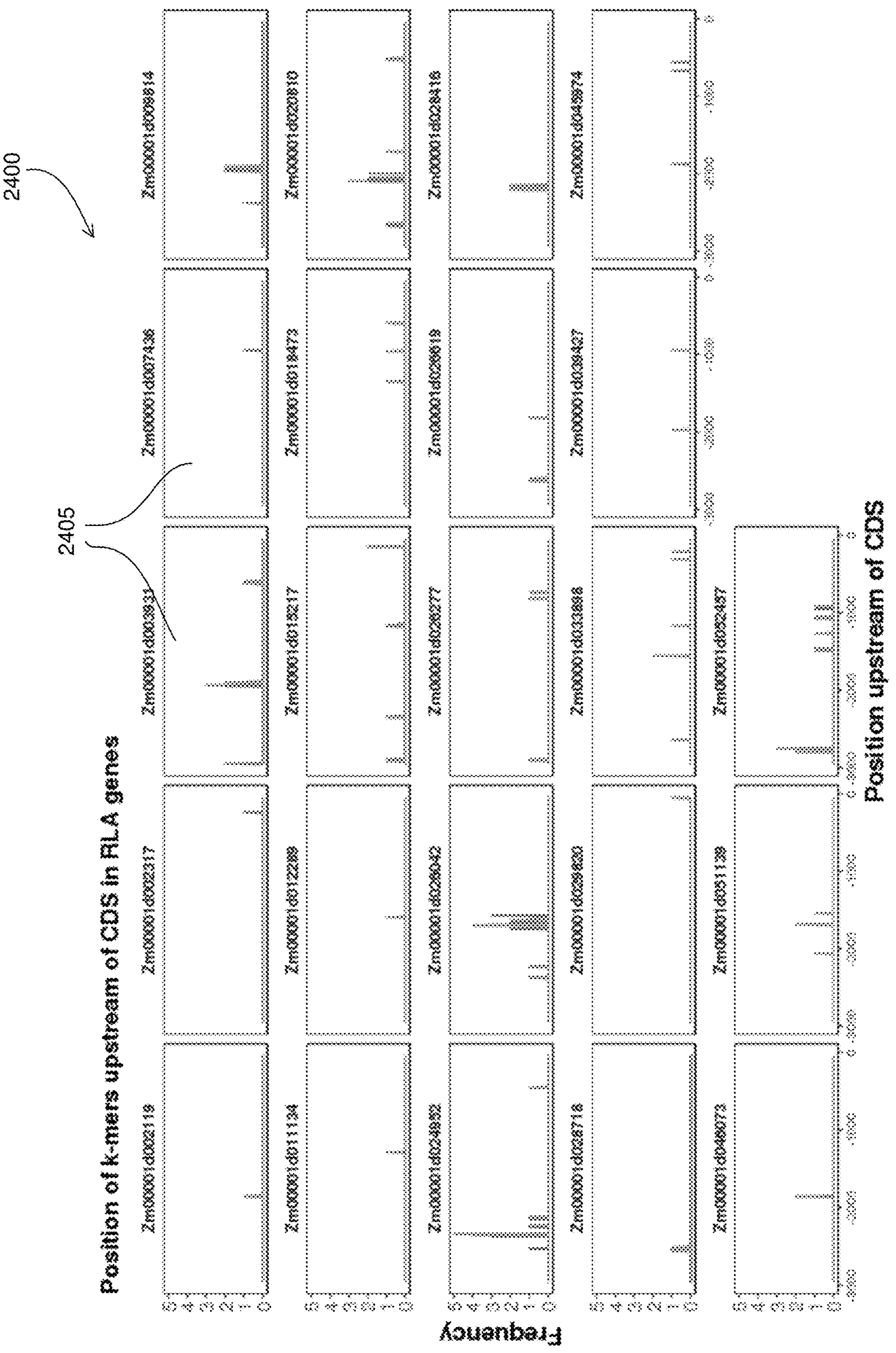
FIG. 24 depicts a plurality of example graphs that illustrate genes associated with relative leaf area phenotypes in response to drought that contain TAGCTA-like motifs in their promoter sequence.

With reference to FIG. 24, a plurality 2400 of graphs 2405 illustrate genes associated with relative leaf area phenotypes in response to drought that contain TAGCTA-like motifs in their promoter sequence. As illustrated, each graph 2405 may represent data associated with a plurality of different genotypes. As illustrated in FIG. 24, genotype-specific distribution and frequency of TAGCTA-like motifs in promoter regions may be observed.

Figure 25:
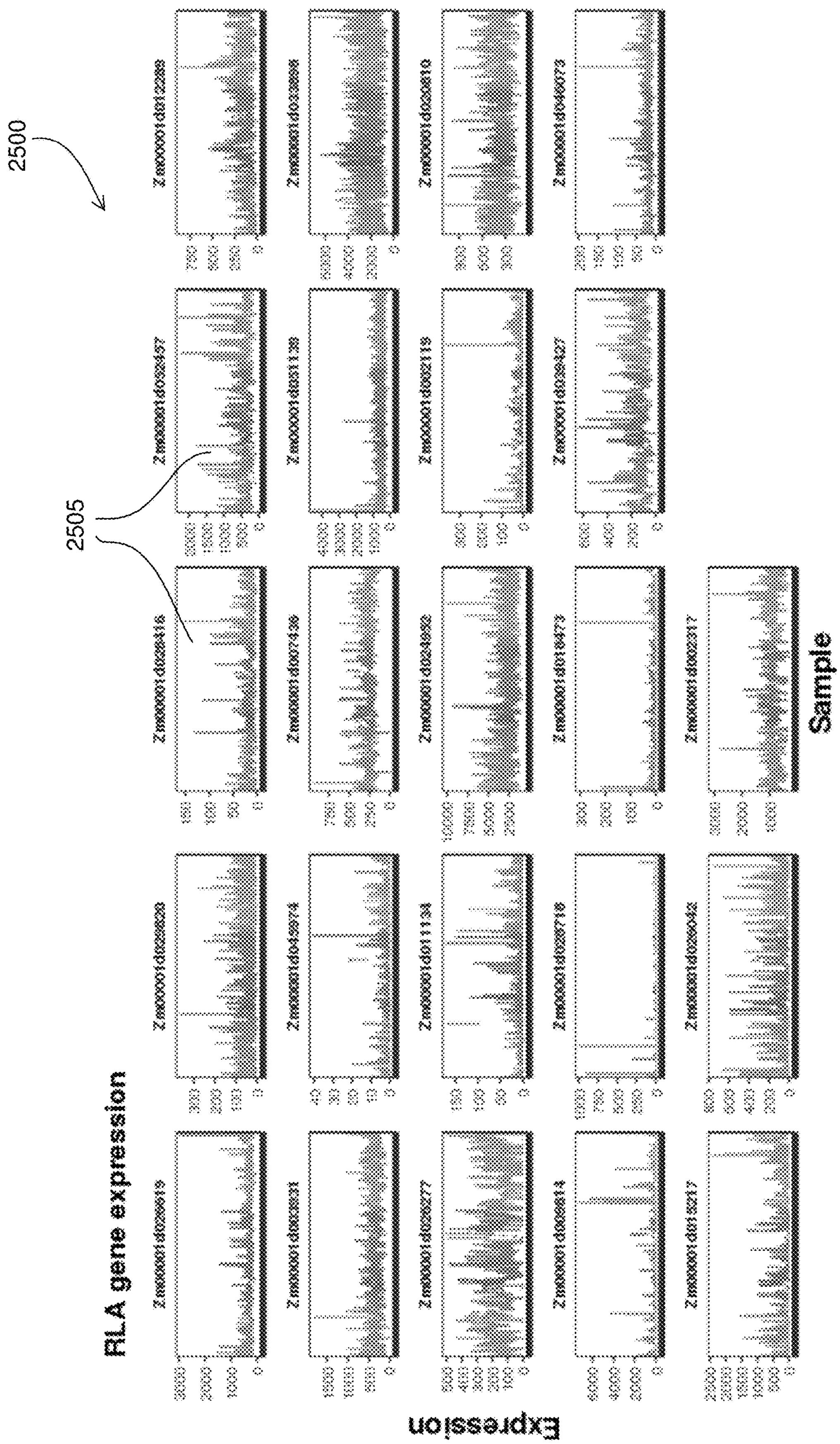
FIG. 25 depicts a plurality of example graphs that illustrate expression of genes associated with relative leaf area phenotypes in response to drought that contain TAGCTA-like motifs in their promoter sequence.

Turning to FIG. 25, a plurality 2500 of graphs 2505 illustrate expression of genes associated with relative leaf area phenotypes in response to drought that contain TAGCTA-like motifs in their promoter sequence. Each line may represent a different genotype. As illustrated in FIG. 25, expression of genes may vary by genotype.

Figure 26:
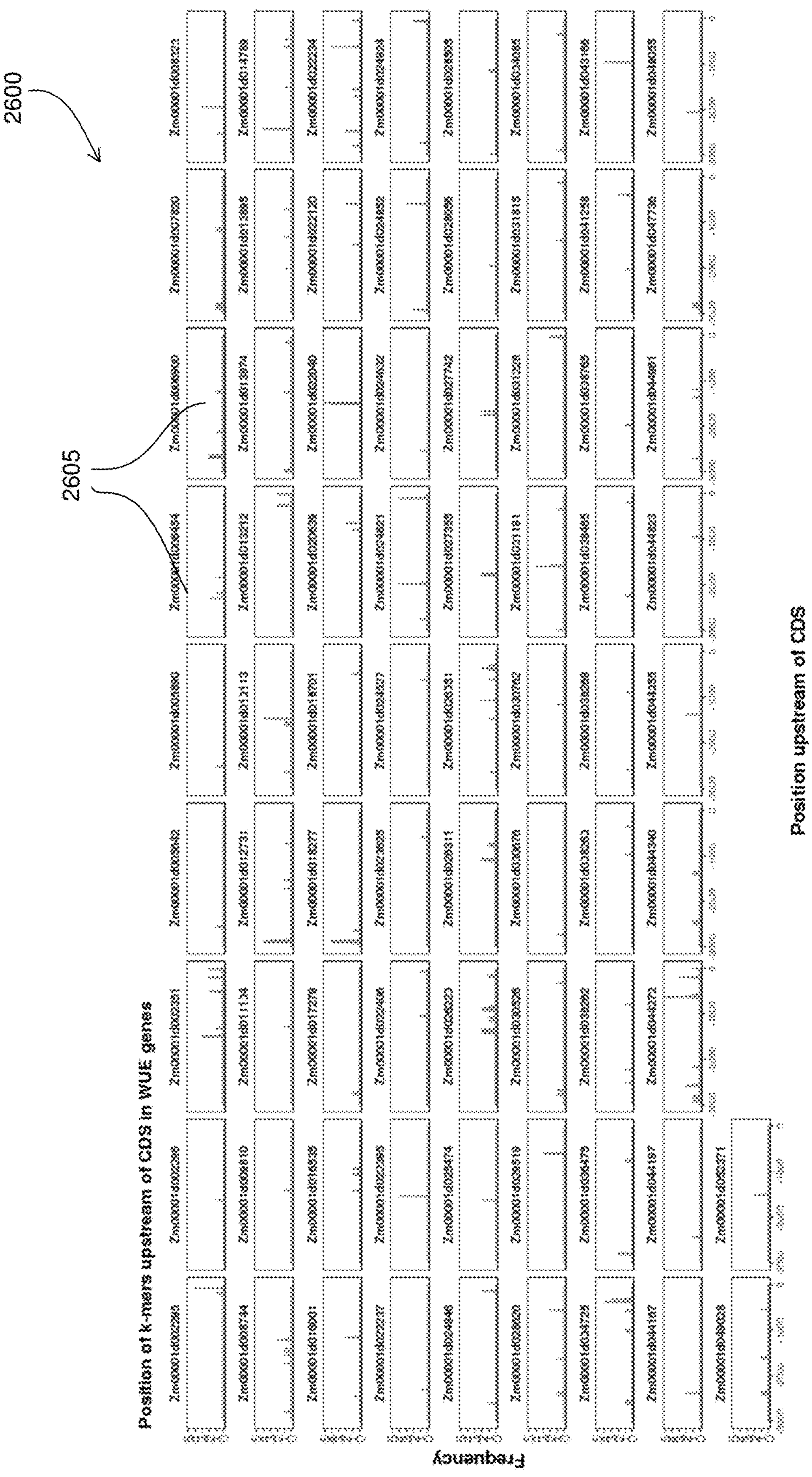
FIG. 26 depicts a plurality of example graphs that illustrate genes associated with water use efficiency phenotypes in response to drought that contain TAGCTA-like motifs in their promoter sequence.

With reference to FIG. 26, a plurality 2600 of graphs 2605 illustrate genes associated with water use efficiency phenotypes in response to drought that contain TAGCTA-like motifs in their promoter sequence. Each line may represent a different genotype. As illustrated in FIG. 26, genotype-specific distribution and frequency of TAGCTA-like motifs in promoter regions may be observed.

Figure 27:
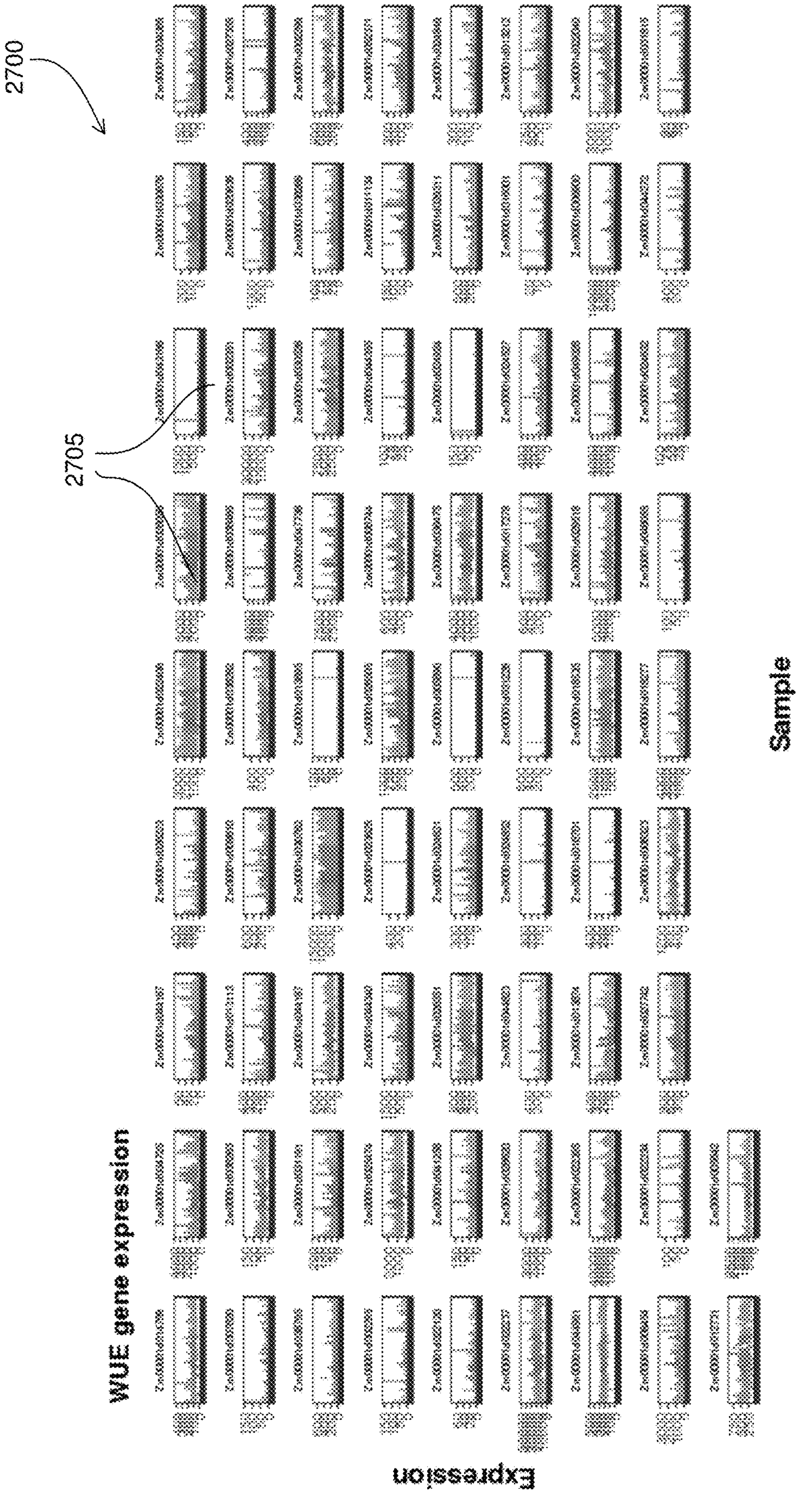
FIG. 27 depicts a plurality of example graphs that illustrate expression of genes associated with water use efficiency phenotypes in response to drought that contain TAGCTA-like motifs in their promoter sequence.

Turning to FIG. 27, a plurality 2700 of graphs 2705 illustrate expression of genes associated with water use efficiency phenotypes in response to drought that contain TAGCTA-like motifs in their promoter sequence. Each line may represent a different genotype. As illustrated in FIG. 27, expression of genes may vary by genotype.

As described herein, novel cis-regulatory elements may be identified using natural language processing (NLP), and upstream transcriptional regulators may be identified using NLP and expressive genome-wide association study data. Natural language processing (NLP) may be used to identify certain cis-regulatory elements in select genotypes. NLP may be used more broadly in other areas of biological trait research. The apparatuses, systems, and methods of the present disclosure may be used for: DNA sequencing, expression of gene(s) (or alleles, haplotypes, etc) across genotypes (or cell/tissue types), genome editing for breeding, protein translation, chromatin remodeling, identifying recombination sites, modifications of carbohydrates, etc.

ADDITIONAL CONSIDERATIONS

This detailed description is to be construed as exemplary only and does not describe every possible embodiment, as describing every possible embodiment would be impractical, if not impossible. One may implement numerous alternate embodiments, using either current technology or technology developed after the filing date of this application.

Furthermore, although the present disclosure sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims. Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In exemplary embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software), may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of some of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

The patent claims at the end of this patent application are not intended to be construed under 35 U.S.C. § 112(f) unless traditional means-plus-function language is expressly recited, such as "means for" or "step for" language being explicitly recited in the claim(s).

This detailed description is to be construed as exemplary only and does not describe every possible embodiment, as describing every possible embodiment would be impractical, if not impossible. One may be implement numerous alternate embodiments, using either current technology or technology developed after the filing date of this application.

What is claimed is:

1. An apparatus for identifying genetic elements, the apparatus comprising:

one or more hardware processors;

a deoxyribonucleic acid (DNA) sequence data receiving module stored on a memory that, when executed by the one or more hardware processors, causes the one or more hardware processors to receive DNA sequence data;

a first machine learning model module stored on the memory that, when executed by the one or more hardware processors, causes the one or more hardware processors to generate first machine learning model output data based on the DNA sequence data, wherein the first machine learning model output data includes word embeddings defining vector representations of k-mers, and wherein the first machine learning model module includes a first machine learning model selected from: a natural language processing (NLP) model, a Bayesian mixture model, a hidden Markov model, a dynamic Bayesian network model, a deep multilayer perceptron (MLP) model, a convolutional neural network (CNN) model, a recursive neural network model, recurrent neural network model, a long short-term memory (LSTM) model, a sequence-to-sequence model, or a shallow neural network model;

a second machine learning model module stored on the memory that, when executed by the one or more hardware processors, causes the one or more hardware processors to generate second machine learning model output data based on the DNA sequence data, wherein the second machine learning model module includes a second machine learning model selected from: a NLP model, a Bayesian mixture model, a hidden Markov model, a dynamic Bayesian network model, a MLP model, a CNN model, a recursive neural network model, a recurrent neural network model, a LSTM model, a sequence-to-sequence model, or a shallow neural network model, and wherein the first machine learning model is different than the second machine learning model; and an optimization model module stored on the memory that, when executed by the one or more hardware processors causes the one or more hardware processors to identify at least one genetic element by:

(i) inputting the first machine learning model output data and the second machine learning model output data into a NLP model to identify a plurality of genetic elements, and (ii) removing known genetic elements from the plurality of genetic elements.

2. The apparatus as in claim 1, wherein the first machine learning model module includes a first DNA sequence data preprocessing module, wherein the second machine learning model module includes a second DNA sequence data preprocessing module, and wherein the second DNA sequence data preprocessing module is different than the first DNA sequence data preprocessing module.

3. The apparatus as in claim 1, wherein at least one of the first machine learning model module or the second machine learning model module includes a natural language processing module that computes attention weights.

4. The apparatus as in claim 1, wherein at least one of the first machine learning model module or the second machine learning model module includes gradient-based methods to analyze an importance of whole k-mers.

5. The apparatus as in claim 1, wherein at least one of the first machine learning model module or the second machine learning model module includes a logistic regression model.

6. The apparatus as in claim 1, wherein the second machine learning model module includes a feed-forward neural network model with word embeddings.

7. A computer-implemented method for identifying genetic elements, the computer-implemented method comprising:

receiving, at one or more processors of a computing device, deoxyribonucleic acid (DNA) sequence data in response to the one or more processors executing a DNA sequence data receiving module;

generating, using the one or more processors, first machine learning model output data based on the DNA sequence data in response to the one or more processors executing a first machine learning model module, wherein the first machine learning model output data includes word embeddings defining vector representations of k-mers, wherein the first machine learning model module includes a first machine learning model selected from: a natural language processing (NLP) model, a Bayesian mixture model, a hidden Markov model, a dynamic Bayesian network model, a deep multilayer perceptron (MLP) model, a convolutional neural network (CNN) model, a recursive neural network model, recurrent neural network model, a long short-term memory (LSTM) model, a sequence-to-sequence model, or a shallow neural network model;

generating, using the one or more processors, second machine learning model output data based on the DNA sequence data in response to the one or more processors executing a second machine learning model module, wherein the second machine learning model module includes a second machine learning model selected from: a NLP model, a Bayesian mixture model, a hidden Markov model, a dynamic Bayesian network model, a MLP model, a CNN model, a recursive neural network model, a recurrent neural network model, a LSTM model, a sequence-to-sequence model, or a shallow neural network model, and wherein the first machine learning model is different than the second machine learning model; and identifying, using the one or more processors and by executing an optimization model module, at least one genetic element by:

(i) inputting the first machine learning model output data and the second machine learning model output data into a NLP model to identify a plurality of genetic elements, and (ii) removing known genetic elements from the plurality of genetic elements.

8. The computer-implemented method as in claim 7, wherein the first machine learning model module includes a first DNA sequence data preprocessing module, wherein the second machine learning model module includes a second DNA sequence data preprocessing module, and wherein the second DNA sequence data preprocessing module is different than the first DNA sequence data preprocessing module.

9. The computer-implemented method as in claim 8, wherein the first DNA sequence data preprocessing module generates at least one of: the word embeddings, feature-based representations, or contextual word embeddings.

10. The computer-implemented method as in claim 7, wherein at least one of the first machine learning model module or the second machine learning model module includes a logistic regression model.

11. The computer-implemented method as in claim 7, wherein the second machine learning model module includes a feed-forward neural network model with word embeddings.

12. A non-transitory computer-readable medium storing computer-readable instructions that, when executed by one or more processors cause the one or more processors to identify genetic elements, the non-transitory computer-readable medium comprising:

a deoxyribonucleic acid (DNA) sequence data receiving module that, when executed by the one or more processors, causes the one or more processors to receive DNA sequence data;

a first machine learning model module that, when executed by the one or more processors, causes the one or more processors to generate first machine learning model output data based on the DNA sequence data, wherein the first machine learning model output data includes word embeddings defining vector representations of k-mers, wherein the first machine learning model module includes a first machine learning model selected from: a natural language processing (NLP) model, a Bayesian mixture model, a hidden Markov model, a dynamic Bayesian network model, a deep multilayer perceptron (MLP) model, a convolutional neural network (CNN) model, a recursive neural network model, recurrent neural network model, a long short-term memory (LSTM) model, a sequence-to-sequence model, or a shallow neural network model;

a second machine learning model module that, when executed by the one or more processors, causes the one or more processors to generate second machine learning model output data based on the DNA sequence data, wherein the second machine learning model module includes a second machine learning model selected from: a NLP model, a Bayesian mixture model, a hidden Markov model, a dynamic Bayesian network model, a MLP model, a CNN model, a recursive neural network model, a recurrent neural network model, a LSTM model, a sequence-to-sequence model, or a shallow neural network model, and wherein the first machine learning model is different than the second machine learning model; and an optimization model module that, when executed by the one or more processors, causes the one or more processors to identify at least one genetic element by:

(i) inputting the first machine learning model output data and the second machine learning model output data into a NLP model to identify a plurality of genetic elements, and (ii) removing known genetic elements from the plurality of genetic elements.

13. The non-transitory computer-readable medium as in claim 12, wherein the first machine learning model module includes a first DNA sequence data preprocessing module, wherein the second machine learning model module includes a second DNA sequence data preprocessing module, and wherein the second DNA sequence data preprocessing module is different than the first DNA sequence data preprocessing module.

14. The non-transitory computer-readable medium as in claim 13, wherein the first DNA sequence data preprocessing module generates at least one of: the word embeddings, feature-based representations, or contextual word embeddings.

15. The non-transitory computer-readable medium as in claim 12, wherein at least one of the first machine learning model module or the second machine learning model module includes a natural language processing module that computes attention weights.

16. The non-transitory computer-readable medium as in claim 12, wherein at least one of the first machine learning model module or the second machine learning model module includes a logistic regression model.

17. The non-transitory computer-readable medium as in claim 12, wherein the first machine learning model module includes a feed-forward neural network model with the word embeddings.

18. The non-transitory computer-readable medium as in claim 12, wherein the identification is based on a score of the first machine learning model output data and a score of the second machine learning model output data.

19. The non-transitory computer-readable medium as in claim 12, wherein the at least one genetic element comprises a cis-regulatory element.

20. The non-transitory computer-readable medium as in claim 12, wherein the second machine learning model output data includes word embeddings defining vector representations of k-mers.

* * * * *

SEQUENCE LISTING

<160> NUMBER OF SEQ ID NOS: 22

<210> SEQ ID NO 1
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 1
agctagctag 10

<210> SEQ ID NO 2
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 2
aatctaatcc 10

<210> SEQ ID NO 3
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 3
tttcttctct 10

<210> SEQ ID NO 4
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 4
cagaaaagga 10

<210> SEQ ID NO 5
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 5
cagaaaagga 10

<210> SEQ ID NO 6
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 6
aaaaaatttc 10

<210> SEQ ID NO 7
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 7
gatgacatgg 10

<210> SEQ ID NO 8
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 8
attttcttca 10

<210> SEQ ID NO 9
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 9
gcaacgtgtc 10

<210> SEQ ID NO 10
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)..(7)
<223> OTHER INFORMATION: n is a, c, g, or t

<400> SEQUENCE: 10 caannnnatc 10

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
acataaaata aaaaaaggca 20

<210> SEQ ID NO 12
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 12
gccacgtggg 10

<210> SEQ ID NO 13
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 13
tccacgtctc 10

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
cgaaaccagc aacggtccag 20

<210> SEQ ID NO 15
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 15
agcaacggtc 10

<210> SEQ ID NO 16
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 16
taactsagtt a 11

<210> SEQ ID NO 17
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 17
gcaacgcaac 10

<210> SEQ ID NO 18
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 18
cacgagscck ccac 14

<210> SEQ ID NO 19
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 19
acgtaagcgc ttacgt 16

<210> SEQ ID NO 20
<211> LENGTH: 10

-continued

```
<212> TYPE: DNA
<213> ORGANISM: Artificial Sequence
<220> FEATURE:
<223> OTHER INFORMATION: Synthetic polynucleotide

<400> SEQUENCE: 20

gatgayrtgg                                                          10


<210> SEQ ID NO 21
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 21

tccatgcatg cac                                                      13


<210> SEQ ID NO 22
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 22

cgtccatgca t                                                        11
```